United States Patent [19]

Alitalo et al.

[11] Patent Number: 5,776,755

[45] Date of Patent: Jul. 7, 1998

[54] FLT4, A RECEPTOR TYROSINE KINASE

[75] Inventors: Kari Alitalo, Espoo; Olga Aprelikova, Helsinki; Katri Pajusola, Helsinki; Elina Armstrong, Helsinki; Jaana Korhonen, Helsinki; Arja Kaipainen, Helsinki, all of Finland

[73] Assignee: Helsinki University Licensing, Ltd., Helsinki, Finland

[21] Appl. No.: 340,011

[22] Filed: Nov. 14, 1994

Related U.S. Application Data

[63] Continuation-in-part of Ser. No. 959,951, Oct. 9, 1992, abandoned.

[51] Int. Cl.$^6$ .................. C12N 9/12; C12N 15/54; C12N 15/63; C12N 15/58
[52] U.S. Cl. .................. 435/194; 435/69.1; 435/252.3; 435/320.1; 536/23.2; 536/23.5; 536/24.31; 536/24.33; 935/14; 935/22; 935/66; 935/71
[58] Field of Search .................. 435/69.1, 194, 435/252.3, 320.1; 536/23.2, 23.5, 24.31, 24.33

[56] References Cited

U.S. PATENT DOCUMENTS

| | | | |
|---|---|---|---|
| 4,652,639 | 3/1987 | Stabinsky | 536/23.1 |
| 5,183,884 | 2/1993 | Kraus et al. | 536/23.5 |
| 5,185,438 | 2/1993 | Lemischka | 536/23.2 |
| 5,198,359 | 3/1993 | Taniguchi et al. | 435/252.3 |
| 5,231,001 | 7/1993 | Kaplan et al. | 435/7.21 |
| 5,270,458 | 12/1993 | Lemischka | 536/23.5 |
| 5,283,354 | 2/1994 | Lemischka | 536/23.5 |
| 5,367,057 | 11/1994 | Lemischka | 530/350 |

FOREIGN PATENT DOCUMENTS

| | | | |
|---|---|---|---|
| 0325224 | 7/1984 | European Pat. Off. | 536/23.5 |
| 9014425 | 11/1990 | WIPO | 536/23.5 |
| 9213867 | 2/1992 | WIPO | 536/23.5 |
| 9214748 | 3/1992 | WIPO | 536/23.5 |
| WO 93/14124 | 7/1993 | WIPO | |
| WO 94/10202 | 5/1994 | WIPO | |

OTHER PUBLICATIONS

Ulrich, A., and Schlessinger, J., 1990, *Cell*, 61(2):203–212.
Matthews, W., et al., 1991, *Cell*, 65(7): 1143–1152.
Partanen, J., et al., 1990, *Proceedings of the National Academy of Sciences, U.S.A.*, 87(22): 8913–8917.
Terman, B., I., et al., 1991, *Oncogene*, 6(9):1677–1683.
Rosnet, O., et al., 1991, *Oncogene*, 6(9): 1641–1650.
Matthews, W., et al., 1991, *Proceedings of The National Academy of Sciences, U.S.A.*, 88(20): 9026–9030.
Aprelikova, O., et al., 1992, *Cancer Research*, 52(3):746–748.
Pajusola, K., et al., 1992, *Cancer Research*, 52(20):5738–5743.
Terman, B. I., et al., 1992, *Biochemical and Biophysical Research Communications*, 187(3):1579–1586.
Oelrichs, R.B., et al., 1993, *Oncogene*, 8(1):11–18.
Galland, F., et al., 1992, *Genomics*, 13:475–478.
Galland, F., et al., 1993, *Oncogene*, 8(5):1233–1240.
Finnerty, H., et al., 1993, *Oncogene*, 8(11):2293–2298.
Bolen, J.B., 1993, *Oncogene*, 8:2025–2031.
West, A.P., and Cooke, B.A., 1991, *Journal of Endocrinology*, 131:Abstract 107.
Moroni, M.C., et al., 1992, *The Journal of Biological Chemistry*, 267(5):2714–2722.
Tortorra, G., et al., 1991, *Proceedings of the National Academy of Sciences, U.S.A.*, 88(5):2011–2015.
Perumor, N.D., et al., 1992, *Journal of Cellular Biochemistry, Supplement*, 16, Part B:285, Abstract J216.

(List continued on next page.)

*Primary Examiner*—Charles L. Patterson, Jr.
*Assistant Examiner*—William W. Moore
*Attorney, Agent, or Firm*—Marshall, O'Toole, Gerstein, Murray & Borun

[57] ABSTRACT

FLT4 gene, expression systems and proteins are provided for use in diagnosis and treatment of conditions related to the tyrosine kinase receptor encoded by the FLT4 gene.

45 Claims, 23 Drawing Sheets

OTHER PUBLICATIONS

Fortkamp, E., et al., 1986, DNA, 5(6):511–517.

Andersson et al., "Structural and Functional Markers During Induced Differentiation in Human Leukemia Cell Lines," In R. F. Revoltella (ed.), *Expression of Differentiated Functions in Cancer Cells*. 239–245, Raven Press, New York (1982).

Aneja et al., "Acyl–Chloro–Deoxyglycerophophorylcholines: Structure of the So–Called Cyclic Lysolecithins," *Biochim. Biophys. Acta*, 239:84–91 (1971).

Aprelikova et al., "FLT4, A Novel Class III Receptor Tyrosine Kinase in Chromosome 5Q33–qter," *Cancer Research*, 52(3):746–748 (Feb. 1, 1992).

Berridge et al., "Cell–Lineage Antigens of the Stem Cell–Megakaryocyte–Platelet Linkage are Associated with the Platelet Linkage are Associated with the Platelet IIb–IIIa Glycoprotein Complex," *Blood*, 66(1):76–85 (Jul., 1985).

Bolen, J.B., "Nonreceptor Tyrosine Protein Kinases," *Oncogene*, 8:2025–2031 (1993).

Bonthron et al., "Nucleotide Sequence of Pre–Pro–Von Willebrand Factor cDNA," *Nucleic Acids Res.*, 14(17):7125–7127 (1986).

Cantley et al., "Oncogenes and Signal Transduction," *Cell*, 64:281–302 (Jan. 25, 1991).

Catoretti et al., "Monoclonal Antibodies Against Recombinant Parts of the Ki–67 Antigen (MIB 1 and MIB 3) Detect Proliferating Cells in Microwave–Processed Formalin–Fixed Paraffin Section" *J. of Pathol.*, 168–357–363 (1992).

Cheng & Flanagan, "Identification and Cloning of ELF–1, a Developmentally Expressed Ligand for the Mek4 and Sek Receptor Tyrosine Kinases," *Cell*, 79:157–168 (Oct. 7, 1994).

Chomczynski et al., "Single–Step Method of RNA Isolation by Acid Guanidium Thiocynate–Phenol–Chloroform Extraction," *Anal. Biochem.*, 162:156–159 (1987).

Cole et al., "The EBV–Hybridoma Technique and Its Application to Human Lung Cancer," *Monoclonal Antibodies and Cancer Therapy*, Alan R Liss, Inc., pp. 77–96 (1985).

Collins et al., "Continuous Growth and Differentiation of Human Myeloid Leukaemic Cells in Suspension Culture," *Nature*, 270:347–349 (1977).

Devereux et al., "A Comprehensive Set of Sequence Analysis Programs for the VAX," *Nucleic Acids Res.*, 12(1):387–395 (1984).

Edgell et al., "Permanent Cell Line Expressing Human Factor VIII–Related Antigen Established by Hybridization," *Proc. Nat'l. Acad. Sci. USA*, 50:3734–3737 (Jun., 1983).

Finnerty et al., "Molecular Cloning g of Murine FLT and FLT4," *Oncogene*, 8(11):2293–2298 (1993).

Flanagan & Leder, "The kit Ligand: A Cell Surface Molecule Altered in Steel Mutant Fibroblasts," *Cell*, 63:185–194 (Oct. 5, 1990).

Fortkamp et al., "Cloning and Expression in *Escherichia coli* of a Synthetic DNA for Hirudin, the Blood Coagulation Inhibitor in the Leech," *DNA*, 5(6):511–517 (1986).

Gahmberg et al., "Membrane Glycolysation During Cell Differentiation," In L. C. Andersson, et al. (ed.), *Gene Expression During Normal and Malignant Differentiation*, 107–123, Academic Press, London (1985).

Galland et al., "Chromosomal Localization of FLT4, a Novel Receptor–Type Tyrosine Kimase Gene," *Genomics*, 13:475–478 (1992).

Galland et al., "The FLT4 Gene Encodes a Transmembrane Tyrosine Kinase Related to the Vascular Endothelial Growth Factor Receptor," *Oncogene*, 8(11):1233–1240 (1993).

Genbank Accession X60280 plasmid pLTRpoly, deposited by Maekelae et al., dated Oct. 8, 1991.

Greenberg et al., "Characterization of a New Megakaryocyte Cell Line: The Dami Cell," *Blood*, 72(6):1968–1977 (Dec., 1988).

Harlow et al., Antibodies: A Laboratory Manual, pp. 72–137, 141–157, 287 & 321–358 (1988).

Heldin et al., "Platelet–Derived Growth Factor: Mechanism of Action and Possible in Vivo Function," *Cell Regulation*, 1:555–566 (Jul., 1990).

Hemmila et al., "Europium as a Label in Time–Resolved Immunofluorometric Assays," *Annal. Biochem.*, 137:335–343 (1984).

Hirai et al., "A Novel Putative Tyrosine Kinase Receptor Encoded by the eph Gene," *Science*, 238:1717–1720 (1987).

Huang et al., "The Hematopoietic Growth Factor KL is Encoded by the SI Locus and is the Ligand of the c–kit Receptor, the Gene Product of the W Locus," *Cell*, 63:225–33 (Oct. 5, 1990).

Kaipainen et al., "Expression of the FMS–Like Tyrosine Kinase 4 Gene Becomes Restricted to Lymphatic Endothelium During Development," *Proc. Nat'l Acad. Sci, USA*, 92:3566–3570 (Apr. 1995).

Kaipainen et al., "The Related FLT4, FLT1, and KDR Receptor Tyrosine Kinases Show Distinct Expression Patterns in Human Fetal Endothelial Cells," *J. Exp. Med.*, 178:2077–2088 (Dec., 1993).

Kieffer et al., "Uncoupling in the Expression of Platelet GP IIb/IIIa in Human Endothelial Cells and K562 Cells: Absence of Immunologic Crossreactivity Between Platelet GP IIb and the Vitronectin Receptor Alpha Chain," *Blood*, 72(4):1209–1215 (Oct., 1988).

Koeffler et al., "Acute Myelogenous Leukemia: A Human Cell Line Responsive to Colony–Stimulating Activity," *Science*, 200:1153–1154 (1978).

Köhler et al., "Continuous Cultures of Fused Cells Secreting Antibody of Predefined Specificity," *Nature*, 256:495–497 (Aug. 7, 1975).

Korhonen et al., "The Mouse Tie Receptor Tyrosine Kinase Gene: Expression During Embryonic Angiogenesis," *Oncogene (England)*, 9(2):395–403 (Feb., 1994).

Kozak, "An Analysis of 5'–Noncoding Sequences from 699 Vertebrate messenger RNAs," *Nucl. Acids Res.*, 15(20):8125–8148 (1987).

Kozak, "Complilation and Analysis of Sequences Upstream From the Transitional Start Site in Eukaryotic mRNAs," *Nucleic Acids Res.*, 12(2):857–872 (1984).

Kozbor et al., "The Production of Monoclonal Antibodies From Human Lymphocytes," *Immunology Today*, 4(3):72–79 (1983).

Lhotak et al., "Characterization of Elk, a Brain–Specific Receptor Tyrosine Kinase," *Mol. Cell. Biol.*, 11:2496–2502 (May, 1991).

Lindberg et al. "cDNA Cloning and Characterization of eck, an Epithelial Cell Receptor Protein–Tyrosine Kinase in the eph/elk Family of Protein Kinases," *Mol. Cell. Biol.* 10:6316–6324 (Dec., 1990).

Lovgren et al., "Time–Resolved Fluorometry in Immunoassay," In: Collins W.P. (Ed.) *Alternative Immunoassays*, John Wiley & Sons Ltd., pp. 203–217 (1985).

Lozzio et al., "Human Chronic Myelogenous Leukemia Cell–Line With Positive Philadelphia Chromosome," *Blood*, 45(3):321–334 (Mar., 1975).

Lyman et al., "Molecular Cloning of a Ligand for the flt3/flk–2 Tyrosine Kinase Receptor: A Proliferative Factor for Primitive Hematopoietic Cells," *Cell*, 75:1157–1167 (Dec. 17, 1993).

Makela et al., "Plasmid pLTRpoly: a Versatile High–Efficiency Mammalian Expression Vector," *Gene*, 118:293–294 (1992).

Martin et al., "HEL Cells: A New Human Erythroleukemia Cell Line With Spontaneous Induced Globin Expression," *Science*, 216:1233–1235 (1982).

Matthews et al., "A Receptor Tyrosine Kinase cDNA Isolated From a Population of Enriched Primitive Hematopoietic Cells and Exhibiting Close Genetic Linkage to c–kit," *Proc. Natl. Acad. Sci. USA*, 88(20):9026–9030 (Oct., 1991).

Matthews et al., "A Receptor Tyrosine Kinase Specific to Hematopoietic Stem and Progenitor Cell–Enriched Populations," *Cell*, 65(7):1143–1152 (Jun. 28, 1991).

McCutchan et al., "Enhancement of the Infectivity of Simian Virus 40 Deoxyribonucleic Acid with Diethylaminoethyl–Dectran," *J. Natl. Cancer Inst.*, 41:351–357 (1968).

Metzelaar et al., "CD63 Antigen: A Novel Lysosomal Membrane Glycoprotein Cloned by a Screening Procedure for Intracellular Antigens in Eukaryotic Cells," *J. Biol. Chem.*, 266(5):3239–3245 (Feb. 15, 1991).

Millauer et al., High Affinity VEGF Binding and Developmental Expression Suggest Flk–1 as a Major Regulator of Vasculogenesis and Angiogenesis, *Cell*, 72:835–846 (Mar. 26, 1993).

Minowada et al., "Brief Communication: Rosette–Forming Human Lymphoid Cell Lines: Establishment and Evidence for Origin of Thymus–Derived Lymphocytes;" *J. Natl. Cancer Inst.*, 49:891–895 (1972).

Mollinedo et al., "Early and Selective Induction of Apoptosis in Human Leukemic Cells By the Alkyl–Lyosophospholipid ET–18–OCH$_3$," *Biochem. & Biophys. Res. Comm.*, 192(2):603–609 (Apr. 30, 1993).

Moroni et al., "EGF–R Antisense RNA Blocks Expression of the Epidermal Growth Factor Receptor and Suppresses the Tranforming Phenotype of a Human Carcinoma Cell Line," *J. Biol. Chem.*, 267(5):2714–2744 (Feb. 5, 1992).

Mukkala et al., "The Synthesis and Use of Activated N–Benzyl Derivatives of Diethylenetriaminetetraacetic Acids: Alternative Regents for labeling of Antibodies with Metal Ions," *Annal. Biochem*, 176:319–325 (1989).

Nowell et al., "Chromosome Studies in Preleukemic States: Myeloproliferative versus Cytopenic Disorders," *Cancer*, 42:2254–2260 (1978).

Oelrichs et al., "NYK/FLK–1: A putative Receptor Protein Tyrosine Kinease Isolated From E10 Embryonic Neuropithelium is Expressed in Endothelial Cells of the Developing Embryo," *Oncogene*, 8(1):11–18 (Jan., 1993).

Pajusola et al., "FLT4 Receptor Tyrosine Kinase Contains Seven Immunoglobulin–Like Loops and is Expressed in Multiple Human Tissues and Cell Lines," *Cancer Research*, 52(20):5738–5743 (Oct. 15, 1992).

Pajusola et al., "Two Human FLT4 Receptor Tyrosine Kinase Isoforms With Distinct Carboxy Terminal Tails are Produced by Alternative Processing of Primary Transcripts," *Oncogene*, 8:2931–2937 (1993).

Partanen et al., "A Novel Endothelial Cell Surface Receptor Tyrosine Kinase with Extracellular Epidermal Growth Factor Homology Domains," *Mol. Cell. Biol.*, 12(4):1698–1707 (Apr., 1992).

Partanen et al., "Putative Tyrosine Kinases Expressed in K–562 Human Leukemia Cells," *Proc. Nat'l Acad. Sci., USA*, 87(22):8913–8917 (Nov., 1990).

Perumov et al., "Influence of Antisense RNA's of Interleukin–β and Interleukin–1 Receptor Anatagonist on Interleukin–1β Production," *J. Cell. Biochem., Supplement*, 16 pt B:285 (Abstract J216) (1992).

Peters et al., "Vascular Endothelial Growth Factor Receptor Expression During Embryogenesis and Tissue Repair Suggests a Role in Endothelial Differentiation and Blood Vessel Growth," *Proc. Nat'l Acad. Sci., USA*, 90:8915–8919 (Oct., 1993).

Poncz et al., "Cloning and Characterization of Platelet Factor 4 cDNA Derived From a Human Erythroleukemic Cell Line," *Blood*, 69(1):219–223 (Jan., 1987).

Reedijik et al., "Tyr721 Regulates Specific Binding of the CSF–1 Receptor Kinase Insert to P1 3'–Kinase SH2 Domains: a Model for SH2–Mediated for SH2–Mediated Receptor–Target Interactions," *EMBO J.*, 11(4):1365–1372 (1992).

Roitt, M., "Essential Immunology," Blackwell Scientific Pub., Oxford, pp. 65–68 & 74 (1991).

Rosnet et al., "Isolation and Chromosomal Localization of a Novel FMS–Like Tyrosine Kinase Gene," *Oncogene*, 6(9):1641–1650 (1990).

Rosnet et al., "Murine Flt3, a Gene Encoding a Novel Tyrosine Kinase Receptor of the PDFR/CS1R Family," *Genomics*, 9:380–385 (1991).

Sabin, F.R., "The Lymphatic System in Human Embryos, with Consideration of the Morphology of the System as a Whole," *Am. J. Anat.*, 9(1):43–91 (1909).

Sambrook et al., *Molecular Cloning: A Laboratory Manual*, Cold Spring Harbor Laboratory Press, (1989) pp. 2.60–2.70, 4.21–4.32, 7.3–7.36.

Satoh et al., "Regional Localization of the HUman c–ros–1 on 6q22 and flt on 13q12," *Jpn. J. Cancer Res.*, 78:772–775 (1987).

Schneider et al, "A One–Step Purification of Membrane Proteins Using a High Efficiency Immnuomatrix," *J. Biol. Chem.*, 257(18):10766–10769 (Sep. 25, 1982).

Schwenk et al., "Cell Cycle Dependency of a T–Cell Marker on Lymphoblasts," *Blut*, 31:299–306 (1975).

Sherr et al., "The c–fms Proto–Oncogene Product is Related to the Receptor for the Mononuclear Phagocyte Growth Factor, CSF–1," *Cell*, 41:665–676 (Jul., 1985).

Shi et al., "16–Kilodalton Heparin Binding (Fibroblasts) Growth Factor Type One Appears in a Stable 40–Kilodation Complex After Receptor–Dependent Internalization," *J. Biol. Chem.*, 266(9):5774–5779 (Mar. 25, 1991).

Shibuya et al., "Nucleotide Sequence and Expression of a Novel Human Receptor–Type Tyrosine Kinase Gene (flt) Closely Related to the fms Family," *Oncogene*, 5:519–524 (1990).

Southern & Berg, "Transformation of Mammalian Cells to Antibiotic Resistance with a Bacterial Gene Under Control of the SV40 Early Region Promoter," *J. Mol. Appl. Genet.*, 1:327–341 (1982).

Stacey et al., "SVpoly: a Versatile Mammalian Expression Vector," *Nucl. Acids Res.*, 18(9):2829 (1990).

Staszewski, R., "Cloning by Limiting Dilution: An Improved Estimate That an Interesting Culture Is Monoclonal," *Yale J. Biol. & Med.*, 57:865–868 (1984).

Staunton et al., "The Arrangement of the Immunoglobulin-Like Domains of ICAM–1 and the Binding Sites for LFA–1 and Rhinovirus," *Cell*, 61:243–254 (Apr. 20, 1990).

Stenman et al., "Human PDGFA Receptor Gene Maps to the Same Region on Chromosome 4 as the KIT Oncogene," *Genes, Chromosomes, Cancer*, 1:155–158 (1989).

Sundström et al., "Establishment and Characterization of a Human Histiocytic Lymphoma Cell Line (U–937)," *Int. J. Cancer*, 17:565–577 (1976).

Swolin et al., "On the 5q–Deletion: Clinical and Cytogenic Observation in Ten Patients and Review of the Literature," *Blood*, 58:986–993 (1981).

Terman et al., "Identification of a New Endothelial Cell growth Factor Receptor Tyrosine Kinase," *Oncogene*, 6(9):1677–1683 (1991).

Terman et al., "Identification of the KDR Tyrosine Kinase as a Receptor for Vascular Endothelial Cell Growth Factor," *Biochem & Biophys. Res. Comm.*, 187(3):1579–1586 (Sep. 30, 1992).

Tessier et al., "Enhanced Secretion From Insect Cells of a Foreign Protein Fused to the Honeybee Melittin Signal Peptide," *Gene*, 98:177–183 (1991).

Thompson et al., "Cloned Human Teratoma Cells Differentiate into Neuron–Like Cells and Other Cell Types in Retinoic Acid," *J. Cell Sci.*, 72:37–64 (1984).

Tokunaga et al., "Nucleotide Sequence of a Full–Length cDNA for Mouse Cytoskeletal Beta–Acting mRNA," *Nucleic Acid. Res.*, 14(6):2829 (1986).

Tomiyasu et al., "Long Arm Deletion of Chromosome No. 5 in a Case of Philadelphia Chromosome–Postive Chronic Myelocytic Leukemia," *Cancer Genet. Cytogenet.*, 2:309–315 (1980).

Tortora et al., "Differentiation of HL–60 Leukemia By Type I Regulatory Subunit Antisense Oligodeoxynucleotide of a cAMP–Dependent Protein Kinase," *Proc. Nat'l Acad. Sci., USA*, 88(5):2011–2015 (Mar., 1991).

Traunecker et al., "Myeloma Based Expression System for Production of LArge Mammalian Proteins," *Tibtech*, 9:109–113 (Apr., 1991).

Ullrich et al., "Signal Transduction By Receptors with Tyrosine Kinase Activity," *Cell*, 61:203–212 (Apr. 20, 1990).

van der Putte, S.CJ., "The Development of the Lymphatic System in Man," *Adv. Anat. Embryol. Cell Biol.*, 51:3 (1975).

Van Den Berghe et al., "Distinct Haematological Disorder with Deletion of Long Arm of No. 5 Chromosome," *Nature*, 251:437–439 (1974).

Van Den Berghe et al., "Transformation of Polycythemia Vera to Myelofibrosis and Late Appearance of a 5q–Chromosome Anomaly," *Cancer Genet. Cytogenet.*, 1:157–162 (1979).

Van Hinsberg et al., "Effect of Thrombin on the Production of Plasminogen Activators and PA Inhibitor–1 by Human Foreskin Microvascular Endothelial Cells," *Thromb. Haemostas.*, 57(2):148–153 (1987).

Van Hinsberg et al., "Production of Plasminogen Activators and Inhibitoes by Serially Propagated Endothlial Cells from Adult Human Blood Vessels," *Arteriosclerosis*, 7:389–400 (Jul./Aug., 1987).

Warrington et al., "Radiation of Hybrid Map of 13 Loci on the Long Arm of Chromosome 5," *Genomics*, 11:701–708 (1991).

West et al., "A Novel Method to Modulate Desensitization and Truncation of LH Receptors Using Antisense Oligodeoxynucleotides," *J. Endocrin.*, 131:(1991) (Abstracts 107).

Whang–Peng et al., "Cytogenic Studies in Patients With Myelofibrosis and Myeloid Metaplasia," *Leuk. Res.*, 2:41–48 (1978).

Wilkinson et al., "A Molecular Analysis of Mouse Development From 8 to 10 Days post coitum Detects Changes Only in Embryonic Globin Expression," *Development*, 99:493–500 )1987).

Wilkinson et al., "Expression of the Proto–Oncogene int–1 is Restricted to Specific Neural Cells in the Development Mouse Embryo," *Cell*, 50:79–88 (1987).

Williams et al., "The Immunoglobin Superfamily–Domains for Cell Surface Recognition," *Ann. Rev. Immunol.*, 381–405 (1988).

Yamaguchi et al., "Flk–1, an Flt–Related Tyrosine Kinase is an Early Marker for Edothelial Cell Precursors," *Development.*, 118:489–498 (1993).

Yarden et al., "Human Proto–Oncogene c–kit: A New Cell Surface Recetor Tyrosine Kinase for an Unidentified Ligand," *EMBO J.*, 6(11):3341–3351 (1987).

Ylänne et al., "Platelet Glycoprotein IIb/IIIa Complex in Cultured Cells: Localization in Focal Adhesion Sites in Spreading HEL Cells," *Blood*, 72:1478–1486 (1988).

```
                                                                        SS
FLT4    1    MQ..RGAALCLRLWLCLGLLDG LVSGYSMTPPTLNITEESHVIDTGDSLS       48
             :::.|::|:||:||:|:|||  |.:|.|.:.|.|:|.|::.|:|.:
FLT1    1    MVSYWDTGVLLCALLSCLLLTG SSGSKLKDPELSLKGTQHIMQAGQTLH       50

IgI
FLT4    49   IS C RGQHPLEWAWPGAQEAPATGKDSEDTGVVRDCEGTDARPYCKVLL       98
             :. | |||..:|.:|. . .:|:  .::|:|.|:| .:.| : :||.|
FLT1    51   LQ C RGEAAHKWSLPE.......MVSKESERLSITKSACGRNGKQFCSTLTL    94

FLT4    99   HEVHAND TGSYV C YKYIKARIEGTTAASSYVFVRDFEQPFINK....PD    144
             :::|.|: |:.|. | ||.:.|:.:|:.:|..:|:|:.|:.|.:|    ::
FLT1    95   NTAQANHTGFYS C KYLAVPTSKKKETESAIYIFISDTGRPFVEMYSEIPE   144

IgII
FLT4    145  TLLVNRKDAMWVP C LVSIPGLNVTLRS.QSSVLWPDGQEVVWDDRRGMLV  193
             .: .::  ||::| | |.|:|:|..::: :|.|.|.|:..:.::.:.:::
FLT1    145  IIHMTEGRELVIP C RVTSPNITVTLKKFPLDTLIPDGKRIIWDSRKGFII   194

FLT4    194  STPLLHDALYLQ C ETTWGDQDFLSNPFLVHITGNELYDIQLLPRKSLELL  243
             |.:..:..:|.| | |.|.|:::.|:.|.:|..::|..::::.::||.:|
FLT1    195  SNATYKEIGLLT C EATVNGHLYKTN.YLTHRQTNTIIDVQISTPRPVKLL  243
```

FIG. 2A

```
                                                                Ig III
                                                    ┌─────────────────────────┐
FLT4  244  VGEKLVLNCTVWAEFNSGVTFDWDYPGKQAERGKWVPERR....SQQTHT  289
           ..:||||.  ..:  ||  .:  ||  . :..  ||
FLT1  244  RGHTLVLNCTATTPLNTRVQMTWSYPD...EKNKRASVRRRIDQSNSHAN   290

FLT4  290  ELSSILTIHNVSQHDLGSYVCKANNGIQRFRESTEVIVHENPFISVEWLK   339
           : :::||.||. . . ||  ||  . :| ||. ||. |  . ||.|.  |
FLT1  291  IFYSVLTIDKMQNKDKGLYTCRVRSGPSFKSVNTSVHIYDKAFITVKHRK   340

Ig IV
                                                    ┌·························
FLT4  340  GPILEATAGDELVKLPVKLAAYPPPEFQWYKDGKALSGRHS.....PHAL   384
           . :||.||      ||  . :    ||.    |   ::
FLT1  341  QQVLETVAGKRSYRLSMKVKAFPSPEVVWLKDGLPATEKSARYLTRGYSL   390

FLT4  385  VLKEVTEASTGTYTLALWNSAAGLRRNISLELVVNVPPQIHEKEASS...   431
           ::.:::||..|| . :|.|.:|.. .||. |.| ||.|.||: | ..|| . ||
FLT1  391  IIKDVTEEDAGNYTILLSIKQSNVFKNLTATLIVNVKPQIYEKAVSSFPD   440
```

FIG. 2B

```
                                                                        Ig V
FLT4  432  PSIYSRHSRQALT C TAYGVPLPLSIQWHRPWTPCKMFAQRSLRRRQQQD  481
           |::|. ||| ||| | |||||||  |.|   .:.  .  |:
FLT1  441  PALYPLGSRQILT C TAYGIPQP.TIKWFWHPCNHNHSEARCDFCSNNEES  489

FLT4  482  LMPQCRDWRAVTTQDAVNPIESLDTWTEFVEGKNKTVSKLVIQNANVSAM   531
            :      ::..    ..  .|||||  |.  |:.|||||.:.:|||
FLT1  490  FILD.......ADSNMGNRIESITQRMAIIEGKNKMASTLVVADSRISGI   532

Ig VI
FLT4  532  YK C VSNKVGQDERLIYFYVTTIPDGFTIESKPSEELLEGQPVLLS C QAD    581
           |: | :|||||| .| ::|:  ||   .:    ::    |       |  |
FLT1  533  YI C TASNKVGTVGRNISFYITDVPNGFHVNLEKMPT..EGEDLKLS C TVN    580

FLT4  582  SYKYEHLRWYRLNLSTLHDAHGNPLLLDCKNVHLFATPLAASLEEVAPGA   631
            :  : |: |:|                 .:    |   |
FLT1  581  KFLYRDVTWILL.........................RTVNNRTMHYSISKQKMAITK   613

FLT4  632  RHA.TLSLSIPRVAPEHEGHYV C EVQDRRSHDKHCHKKYLSVQALEAPRL    680
           .|   :|  :|  .|. ||:  | | :   |     |     ::
FLT1  614  EHSITLNLTIMNVSLQDSGTYA C RARNVYTGEELLQKKEITIRDQEAPYL    663
```

| | | | Ig VII | TM | TK 1 | KI |

```
FLT4  681 TQNLTDLLVNVSDSLEMQCLVAGAHAPSIVWYKDERLLEEKSGVDLADSN 730
FLT1  664 LRNLSDHTVAISSSTTLDCHANGVPEPQITWFKNNHKIQQEPGIILGPGS 713
FLT4  731 QKLSIQRVREEDAGRYLCSVCNAKGCVNSSASVAVEGSEDKGSMEIVILV 780
FLT1  714 STLFIERVTEEDEGVYHCKATNQKGSVESSAYLTVQGTSDKSNLELITLT 763
FLT4  781 GTGVIAVFFWVLLLIFCNMRRPAHADIKTGYLSIIMDPGEVPLEEQCEY 830
FLT1  764 CTCVAATLFWLLLTLLIRKMKRSS.SEIKTDYLSIIMDPDEVPLDEQCER 812
FLT4  831 LSYDASQWEFPRERLHLGRVLGYGAFGKVVEASAFGIHKGSSCDTVAVKM 880
FLT1  813 LPYDASKWEFARERLKLGKSLGRGAFGKVVQASAFGIKKSPTCRTVAVKM 862
FLT4  881 LKEGATASEHRALMSELKILIHIGNHLNVVNLLGACTKPQGPLMVIVEFC 930
FLT1  863 LKEGATASEYKALMTELKILTHIGHHLNVVNLLGACTKQGGPLMVIVEYC 912
FLT4  931 KYGNLSNFLRAKRDAF...SPCAEKSPEQRGRFRAMVELARLDRRRPGSS 977
FLT1  913 KYGNLSNYLKSKRDLFFLNKDAALHMEPKKEKMEPGLEQGKKPRLDSVTS 962
```

```
                                                                    ┐
FLT4   978 DRVLFARFSKTEGGARRASPDQEAEDLWLSPLTMEDLVCYSFQVARGMEF 1027   │
               . .   :  :  .  :.  ::   ::     :: ::: ::::::         │
FLT1   963 SESFASSGFQEDKSLSDVEEEDSDGFYKEPITMEDLISYSFQVARGMEF 1012    │
                                                       □             │
FLT4  1028 LASRKCIHRDLAARNILLSESDVVKICDFGLARDIYKDPDYVRKGSARLP 1077    │ TK 2
           |.:| |||||||||||||||||| | ||||||||||||:|||||||..||        │
FLT1  1013 LSSRKCIHRDLAARNILLSENNVVKICDFGLARDIYKNPDYVRKGDTRLP 1062    │
                                                                     │
FLT4  1078 LKWMAPESIFDKVYTTQSDVWSFGVLLWEIFSLGASPYPGVQINEEFCQR 1127     │
           |||||||||||.|..|.|||| ||||||||||||.|||||||.|:||| |          │
FLT1  1063 LKWMAPESIFDKIYSTKSDVWSYGVLLWEIFSLGGSPYPGVQMDEDFCSR 1112    ┘

FLT4  1128 LRDGTRMRAPELATPAIRRIMLNCWSGDPKARPAFSELVEILGDLLQGRG 1177     ┐
           ||.| ||||||:.||.||.|||  |:||||||||| ||||:||||||||..          │ CT
FLT1  1113 LREGMRMRAPEYSTPEIYQIMLDCWHRDPKERPRFAELVEKLGDLLQANV 1162     ┘
```

FIG. 2E

```
FLT4 1178 LQEEEVCMAPRSSQSSEEGSFSQVSTMALHIAQADAEDSPPSLQRHSLA 1227
FLT1 1163 QQDGKDYIPINAILTGNSGFTYSTPAFSEDFFKESISAPKFNSGSSDDVR 1212
FLT4 1228 ARYYNWVSFPGCLARGAETRGSSRMKTFEEFPMTPTTYKGSVDNQTDSGM 1277
FLT1 1213 YVNAFKFMSLERIKTFEELLPNATSMFDDYQGDSSTLLASPMLKRFTWTD 1262
FLT4 1278 VLASEEFEQIESRHRQESGFR 1298
FLT1 1263 SKPKASLKIEV 1273
```

FIG. 2F

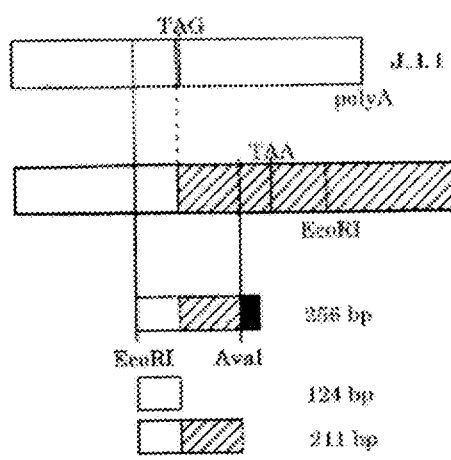
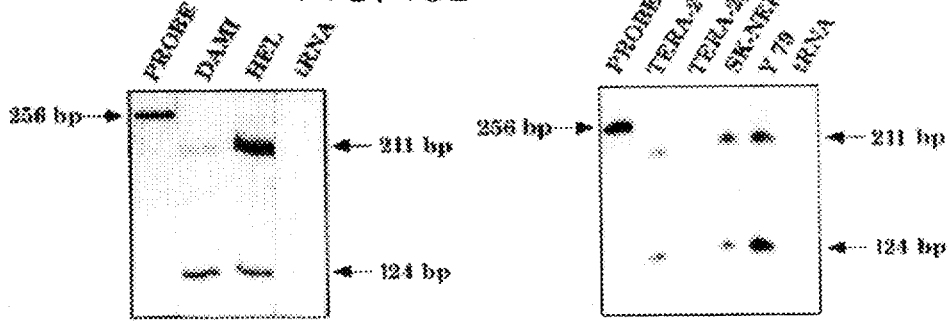
FIG. 10A
FIG. 10B
FIG. 10C

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 4195 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 20..3916

( x i ) SEQUENCE DESCRIPTION: SEQ ID NO:1:

```
CCACGCGCAG  CGGCCGGAG  ATG  CAG  CGG  GGC  GCC  GCG  CTG  TGC  CTG  CGA  CTG        52
                       Met  Gln  Arg  Gly  Ala  Ala  Leu  Cys  Leu  Arg  Leu
                        1                  5                       10

TGG  CTC  TGC  CTG  GGA  CTC  CTG  GAC  GGC  CTG  GTG  AGT  GGC  TAC  TCC  ATG     100
Trp  Leu  Cys  Leu  Gly  Leu  Leu  Asp  Gly  Leu  Val  Ser  Gly  Tyr  Ser  Met
               15                       20                       25

ACC  CCC  CCG  ACC  TTG  AAC  ATC  ACG  GAG  GAG  TCA  CAC  GTC  ATC  GAC  ACC     148
Thr  Pro  Pro  Thr  Leu  Asn  Ile  Thr  Glu  Glu  Ser  His  Val  Ile  Asp  Thr
                30                       35                       40
```

-continued

| | | | | | | | | | | | | | | | | |
|---|---|---|---|---|---|---|---|---|---|---|---|---|---|---|---|---|
| GGT | GAC | AGC | CTG | TCC | ATC | TCC | TGC | AGG | GGA | CAG | CAC | CCC | CTC | GAG | TGG | 196 |
| Gly | Asp | Ser | Leu | Ser | Ile | Ser | Cys | Arg | Gly | Gln | His | Pro | Leu | Glu | Trp | |
| 45 | | | | 50 | | | | | | | 55 | | | | | |
| GCT | TGG | CCA | GGA | GCT | CAG | GAG | GCG | CCA | GCC | ACC | GGA | GAC | AAG | GAC | AGC | 244 |
| Ala | Trp | Pro | Gly | Ala | Gln | Glu | Ala | Pro | Ala | Thr | Gly | Asp | Lys | Asp | Ser | |
| 60 | | | | | 65 | | | | | 70 | | | | | 75 | |
| GAG | GAC | ACG | GGG | GTG | GTG | CGA | GAC | TGC | GAG | GGC | ACA | GAC | GCC | AGG | CCC | 292 |
| Glu | Asp | Thr | Gly | Val | Val | Arg | Asp | Cys | Glu | Gly | Thr | Asp | Ala | Arg | Pro | |
| | | | | 80 | | | | | 85 | | | | | 90 | | |
| TAC | TGC | AAG | GTG | TTG | CTG | CTG | CAC | GAG | GTA | CAT | GCC | AAC | GAC | ACA | GGC | 340 |
| Tyr | Cys | Lys | Val | Leu | Leu | Leu | His | Glu | Val | His | Ala | Asn | Asp | Thr | Gly | |
| | | | 95 | | | | | 100 | | | | | 105 | | | |
| AGC | TAC | GTC | TGC | TAC | TAC | AAG | TAC | ATC | AAG | GCA | CGC | ATC | GAG | GGC | ACC | 388 |
| Ser | Tyr | Val | Cys | Tyr | Tyr | Lys | Tyr | Ile | Lys | Ala | Arg | Ile | Glu | Gly | Thr | |
| | | 110 | | | | | 115 | | | | | 120 | | | | |
| ACG | GCC | GCC | AGC | TCC | TAC | GTG | TTC | GTG | AGA | GAC | TTT | GAG | CAG | CCA | TTC | 436 |
| Thr | Ala | Ala | Ser | Ser | Tyr | Val | Phe | Val | Arg | Asp | Phe | Glu | Gln | Pro | Phe | |
| 125 | | | | | 130 | | | | | 135 | | | | | | |
| ATC | AAC | AAG | CCT | GAC | ACG | CTC | TTG | GTC | AAC | AGG | AAG | GAC | GCC | ATG | TGG | 484 |
| Ile | Asn | Lys | Pro | Asp | Thr | Leu | Leu | Val | Asn | Arg | Lys | Asp | Ala | Met | Trp | |
| 140 | | | | | 145 | | | | | 150 | | | | | 155 | |
| GTG | CCC | TGT | CTG | GTG | TCC | ATC | CCC | GGC | CTC | AAT | GTC | ACG | CTG | CGC | TCG | 532 |
| Val | Pro | Cys | Leu | Val | Ser | Ile | Pro | Gly | Leu | Asn | Val | Thr | Leu | Arg | Ser | |
| | | | | 160 | | | | | 165 | | | | | 170 | | |
| CAA | AGC | TCG | GTG | CTG | TGG | CCA | GAC | GGG | CAG | GAG | GTG | GTG | TGG | GAT | GAC | 580 |
| Gln | Ser | Ser | Val | Leu | Trp | Pro | Asp | Gly | Gln | Glu | Val | Val | Trp | Asp | Asp | |
| | | | 175 | | | | | 180 | | | | | 185 | | | |
| CGG | CGG | GGC | ATG | CTC | GTG | TCC | ACG | CCA | CTG | CTG | CAC | GAT | GCC | CTG | TAC | 628 |
| Arg | Arg | Gly | Met | Leu | Val | Ser | Thr | Pro | Leu | Leu | His | Asp | Ala | Leu | Tyr | |
| | | 190 | | | | | 195 | | | | | 200 | | | | |
| CTG | CAG | TGC | GAG | ACC | ACC | TGG | GGA | GAC | CAG | GAC | TTC | CTT | TCC | AAC | CCC | 676 |
| Leu | Gln | Cys | Glu | Thr | Thr | Trp | Gly | Asp | Gln | Asp | Phe | Leu | Ser | Asn | Pro | |
| | 205 | | | | | 210 | | | | | 215 | | | | | |
| TTC | CTG | GTG | CAC | ATC | ACA | GGC | AAC | GAG | CTC | TAT | GAC | ATC | CAG | CTG | TTG | 724 |
| Phe | Leu | Val | His | Ile | Thr | Gly | Asn | Glu | Leu | Tyr | Asp | Ile | Gln | Leu | Leu | |
| 220 | | | | | 225 | | | | | 230 | | | | | 235 | |
| CCC | AGG | AAG | TCG | CTG | GAG | CTG | CTG | GTA | GGG | GAG | AAG | CTG | GTC | CTG | AAC | 772 |
| Pro | Arg | Lys | Ser | Leu | Glu | Leu | Leu | Val | Gly | Glu | Lys | Leu | Val | Leu | Asn | |
| | | | | 240 | | | | | 245 | | | | | 250 | | |
| TGC | ACC | GTG | TGG | GCT | GAG | TTT | AAC | TCA | GGT | GTC | ACC | TTT | GAC | TGG | GAC | 820 |
| Cys | Thr | Val | Trp | Ala | Glu | Phe | Asn | Ser | Gly | Val | Thr | Phe | Asp | Trp | Asp | |
| | | | 255 | | | | | 260 | | | | | 265 | | | |
| TAC | CCA | GGG | AAG | CAG | GCA | GAG | CGG | GGT | AAG | TGG | GTG | CCC | GAG | CGA | CGC | 868 |
| Tyr | Pro | Gly | Lys | Gln | Ala | Glu | Arg | Gly | Lys | Trp | Val | Pro | Glu | Arg | Arg | |
| | | 270 | | | | | 275 | | | | | 280 | | | | |
| TCC | CAG | CAG | ACC | CAC | ACA | GAA | CTC | TCC | AGC | ATC | CTG | ACC | ATC | CAC | AAC | 916 |
| Ser | Gln | Gln | Thr | His | Thr | Glu | Leu | Ser | Ser | Ile | Leu | Thr | Ile | His | Asn | |
| | 285 | | | | | 290 | | | | | 295 | | | | | |
| GTC | AGC | CAG | CAC | GAC | CTG | GGC | TCG | TAT | GTG | TGC | AAG | GCC | AAC | AAC | GGC | 964 |
| Val | Ser | Gln | His | Asp | Leu | Gly | Ser | Tyr | Val | Cys | Lys | Ala | Asn | Asn | Gly | |
| 300 | | | | | 305 | | | | | 310 | | | | | 315 | |
| ATC | CAG | CGA | TTT | CGG | GAG | AGC | ACC | GAG | GTC | ATT | GTG | CAT | GAA | AAT | CCC | 1012 |
| Ile | Gln | Arg | Phe | Arg | Glu | Ser | Thr | Glu | Val | Ile | Val | His | Glu | Asn | Pro | |
| | | | | 320 | | | | | 325 | | | | | 330 | | |
| TTC | ATC | AGC | GTC | GAG | TGG | CTC | AAA | GGA | CCC | ATC | CTG | GAG | GCC | ACG | GCA | 1060 |
| Phe | Ile | Ser | Val | Glu | Trp | Leu | Lys | Gly | Pro | Ile | Leu | Glu | Ala | Thr | Ala | |
| | | | 335 | | | | | 340 | | | | | 345 | | | |
| GGA | GAC | GAG | CTG | GTG | AAG | CTG | CCC | GTG | AAG | CTG | GCA | GCG | TAC | CCC | CCG | 1108 |
| Gly | Asp | Glu | Leu | Val | Lys | Leu | Pro | Val | Lys | Leu | Ala | Ala | Tyr | Pro | Pro | |
| | | 350 | | | | | 355 | | | | | 360 | | | | |

```
CCC GAG TTC CAG TGG TAC AAG GAT GGA AAG GCA CTG TCC GGG CGC CAC      1156
Pro Glu Phe Gln Trp Tyr Lys Asp Gly Lys Ala Leu Ser Gly Arg His
365                     370                 375

AGT CCA CAT GCC CTG GTG CTC AAG GAG GTG ACA GAG GCC AGC ACA GGC      1204
Ser Pro His Ala Leu Val Leu Lys Glu Val Thr Glu Ala Ser Thr Gly
380                     385                 390                 395

ACC TAC ACC CTC GCC CTG TGG AAC TCC GCT GCT GGC CTG AGG CGC AAC      1252
Thr Tyr Thr Leu Ala Leu Trp Asn Ser Ala Ala Gly Leu Arg Arg Asn
                400                 405                 410

ATC AGC CTG GAG CTG GTG GTG AAT GTG CCC CCC CAG ATA CAT GAG AAG      1300
Ile Ser Leu Glu Leu Val Val Asn Val Pro Pro Gln Ile His Glu Lys
415                     420                 425

GAG GCC TCC TCC CCC AGC ATC TAC TCG CGT CAC AGC CGC CAG GCC CTC      1348
Glu Ala Ser Ser Pro Ser Ile Tyr Ser Arg His Ser Arg Gln Ala Leu
430                     435                 440

ACC TGC ACG GCC TAC GGG GTG CCC CTG CCT CTC AGC ATC CAG TGG CAC      1396
Thr Cys Thr Ala Tyr Gly Val Pro Leu Pro Leu Ser Ile Gln Trp His
445                     450                 455

TGG CGG CCC TGG ACA CCC TGC AAG ATG TTT GCC CAG CGT AGT CTC CGG      1444
Trp Arg Pro Trp Thr Pro Cys Lys Met Phe Ala Gln Arg Ser Leu Arg
460                     465                 470                 475

CGG CGG CAG CAG CAA GAC CTC ATG CCA CAG TGC CGT GAC TGG AGG GCG      1492
Arg Arg Gln Gln Gln Asp Leu Met Pro Gln Cys Arg Asp Trp Arg Ala
                480                 485                 490

GTG ACC ACG CAG GAT GCC GTG AAC CCC ATC GAG AGC CTG GAC ACC TGG      1540
Val Thr Thr Gln Asp Ala Val Asn Pro Ile Glu Ser Leu Asp Thr Trp
495                     500                 505

ACC GAG TTT GTG GAG GGA AAG AAT AAG ACT GTG AGC AAG CTG GTG ATC      1588
Thr Glu Phe Val Glu Gly Lys Asn Lys Thr Val Ser Lys Leu Val Ile
510                     515                 520

CAG AAT GCC AAC GTG TCT GCC ATG TAC AAG TGT GTG GTC TCC AAC AAG      1636
Gln Asn Ala Asn Val Ser Ala Met Tyr Lys Cys Val Val Ser Asn Lys
525                     530                 535

GTG GGC CAG GAT GAG CGG CTC ATC TAC TTC TAT GTG ACC ACC ATC CCC      1684
Val Gly Gln Asp Glu Arg Leu Ile Tyr Phe Tyr Val Thr Thr Ile Pro
540                     545                 550                 555

GAC GGC TTC ACC ATC GAA TCC AAG CCA TCC GAG GAG CTA CTA GAG GGC      1732
Asp Gly Phe Thr Ile Glu Ser Lys Pro Ser Glu Glu Leu Leu Glu Gly
                560                 565                 570

CAG CCG GTG CTC CTG AGC TGC CAA GCC GAC AGC TAC AAG TAC GAG CAT      1780
Gln Pro Val Leu Leu Ser Cys Gln Ala Asp Ser Tyr Lys Tyr Glu His
575                     580                 585

CTG CGC TGG TAC CGC CTC AAC CTG TCC ACG CTG CAC GAT GCG CAC GGG      1828
Leu Arg Trp Tyr Arg Leu Asn Leu Ser Thr Leu His Asp Ala His Gly
590                     595                 600

AAC CCG CTT CTG CTC GAC TGC AAG AAC GTG CAT CTG TTC GCC ACC CCT      1876
Asn Pro Leu Leu Leu Asp Cys Lys Asn Val His Leu Phe Ala Thr Pro
605                     610                 615

CTG GCC GCC AGC CTG GAG GAG GTG GCA CCT GGG GCG CGC CAC GCC ACG      1924
Leu Ala Ala Ser Leu Glu Glu Val Ala Pro Gly Ala Arg His Ala Thr
620                     625                 630                 635

CTC AGC CTG AGT ATC CCC CGC GTC GCG CCC GAG CAC GAG GGC CAC TAT      1972
Leu Ser Leu Ser Ile Pro Arg Val Ala Pro Glu His Glu Gly His Tyr
                640                 645                 650

GTG TGC GAA GTG CAA GAC CGG CGC AGC CAT GAC AAG CAC TGC CAC AAG      2020
Val Cys Glu Val Gln Asp Arg Arg Ser His Asp Lys His Cys His Lys
655                     660                 665

AAG TAC CTG TCG GTG CAG GCC CTG GAA GCC CCT CGG CTC ACG CAG AAC      2068
Lys Tyr Leu Ser Val Gln Ala Leu Glu Ala Pro Arg Leu Thr Gln Asn
670                     675                 680
```

-continued

| | | | | | | | | | | | | | | | | |
|---|---|---|---|---|---|---|---|---|---|---|---|---|---|---|---|---|
| TTG | ACC | GAC | CTC | CTG | GTG | AAC | GTG | AGC | GAC | TCG | CTG | GAG | ATG | CAG | TGC | 2116 |
| Leu | Thr | Asp | Leu | Leu | Val | Asn | Val | Ser | Asp | Ser | Leu | Glu | Met | Gln | Cys | |
| 685 | | | | | 690 | | | | | 695 | | | | | | |
| TTG | GTG | GCC | GGA | GCG | CAC | GCG | CCC | AGC | ATC | GTG | TGG | TAC | AAA | GAC | GAG | 2164 |
| Leu | Val | Ala | Gly | Ala | His | Ala | Pro | Ser | Ile | Val | Trp | Tyr | Lys | Asp | Glu | |
| 700 | | | | | 705 | | | | | 710 | | | | | 715 | |
| AGG | CTG | CTG | GAG | GAA | AAG | TCT | GGA | GTC | GAC | TTG | GCG | GAC | TCC | AAC | CAG | 2212 |
| Arg | Leu | Leu | Glu | Glu | Lys | Ser | Gly | Val | Asp | Leu | Ala | Asp | Ser | Asn | Gln | |
| | | | | 720 | | | | | 725 | | | | | 730 | | |
| AAG | CTG | AGC | ATC | CAG | CGC | GTG | CGC | GAG | GAG | GAT | GCG | GGA | CGC | TAT | CTG | 2260 |
| Lys | Leu | Ser | Ile | Gln | Arg | Val | Arg | Glu | Glu | Asp | Ala | Gly | Arg | Tyr | Leu | |
| | | | 735 | | | | | 740 | | | | | 745 | | | |
| TGC | AGC | GTG | TGC | AAC | GCC | AAG | GGC | TGC | GTC | AAC | TCC | TCC | GCC | AGC | GTG | 2308 |
| Cys | Ser | Val | Cys | Asn | Ala | Lys | Gly | Cys | Val | Asn | Ser | Ser | Ala | Ser | Val | |
| | | 750 | | | | | 755 | | | | | 760 | | | | |
| GCC | GTG | GAA | GGC | TCC | GAG | GAT | AAG | GGC | AGC | ATG | GAG | ATC | GTG | ATC | CTT | 2356 |
| Ala | Val | Glu | Gly | Ser | Glu | Asp | Lys | Gly | Ser | Met | Glu | Ile | Val | Ile | Leu | |
| 765 | | | | | 770 | | | | | 775 | | | | | | |
| GTC | GGT | ACC | GGC | GTC | ATC | GCT | GTC | TTC | TTC | TGG | GTC | CTC | CTC | CTC | CTC | 2404 |
| Val | Gly | Thr | Gly | Val | Ile | Ala | Val | Phe | Phe | Trp | Val | Leu | Leu | Leu | Leu | |
| 780 | | | | | 785 | | | | | 790 | | | | | 795 | |
| ATC | TTC | TGT | AAC | ATG | AGG | AGG | CCG | GCC | CAC | GCA | GAC | ATC | AAG | ACG | GGC | 2452 |
| Ile | Phe | Cys | Asn | Met | Arg | Arg | Pro | Ala | His | Ala | Asp | Ile | Lys | Thr | Gly | |
| | | | | 800 | | | | | 805 | | | | | 810 | | |
| TAC | CTG | TCC | ATC | ATC | ATG | GAC | CCC | GGG | GAG | GTG | CCT | CTG | GAG | GAG | CAA | 2500 |
| Tyr | Leu | Ser | Ile | Ile | Met | Asp | Pro | Gly | Glu | Val | Pro | Leu | Glu | Glu | Gln | |
| | | | 815 | | | | | 820 | | | | | 825 | | | |
| TGC | GAA | TAC | CTG | TCC | TAC | GAT | GCC | AGC | CAG | TGG | GAA | TTC | CCC | CGA | GAG | 2548 |
| Cys | Glu | Tyr | Leu | Ser | Tyr | Asp | Ala | Ser | Gln | Trp | Glu | Phe | Pro | Arg | Glu | |
| | | 830 | | | | | 835 | | | | | 840 | | | | |
| CGG | CTG | CAC | CTG | GGG | AGA | GTG | CTC | GGC | TAC | GGC | GCC | TTC | GGG | AAG | GTG | 2596 |
| Arg | Leu | His | Leu | Gly | Arg | Val | Leu | Gly | Tyr | Gly | Ala | Phe | Gly | Lys | Val | |
| 845 | | | | | 850 | | | | | 855 | | | | | | |
| GTG | GAA | GCC | TCC | GCT | TTC | GGC | ATC | CAC | AAG | GGC | AGC | AGC | TGT | GAC | ACC | 2644 |
| Val | Glu | Ala | Ser | Ala | Phe | Gly | Ile | His | Lys | Gly | Ser | Ser | Cys | Asp | Thr | |
| 860 | | | | | 865 | | | | | 870 | | | | | 875 | |
| GTG | GCC | GTG | AAA | ATG | CTG | AAA | GAG | GGC | GCC | ACG | GCC | AGC | GAG | CAC | CGC | 2692 |
| Val | Ala | Val | Lys | Met | Leu | Lys | Glu | Gly | Ala | Thr | Ala | Ser | Glu | His | Arg | |
| | | | | 880 | | | | | 885 | | | | | 890 | | |
| GCG | CTG | ATG | TCG | GAG | CTC | AAG | ATC | CTC | ATT | CAC | ATC | GGC | AAC | CAC | CTC | 2740 |
| Ala | Leu | Met | Ser | Glu | Leu | Lys | Ile | Leu | Ile | His | Ile | Gly | Asn | His | Leu | |
| | | | 895 | | | | | 900 | | | | | 905 | | | |
| AAC | GTG | GTC | AAC | CTC | CTC | GGG | GCG | TGC | ACC | AAG | CCG | CAG | GGC | CCC | CTC | 2788 |
| Asn | Val | Val | Asn | Leu | Leu | Gly | Ala | Cys | Thr | Lys | Pro | Gln | Gly | Pro | Leu | |
| | | 910 | | | | | 915 | | | | | 920 | | | | |
| ATG | GTG | ATC | GTG | GAG | TTC | TGC | AAG | TAC | GGC | AAC | CTC | TCC | AAC | TTC | CTG | 2836 |
| Met | Val | Ile | Val | Glu | Phe | Cys | Lys | Tyr | Gly | Asn | Leu | Ser | Asn | Phe | Leu | |
| 925 | | | | | 930 | | | | | 935 | | | | | | |
| CGC | GCC | AAG | CGG | GAC | GCC | TTC | AGC | CCC | TGC | GCG | GAG | AAG | TCT | CCC | GAG | 2884 |
| Arg | Ala | Lys | Arg | Asp | Ala | Phe | Ser | Pro | Cys | Ala | Glu | Lys | Ser | Pro | Glu | |
| 940 | | | | | 945 | | | | | 950 | | | | | 955 | |
| CAG | CGC | GGA | CGC | TTC | CGC | GCC | ATG | GTG | GAG | CTC | GCC | AGG | CTG | GAT | CGG | 2932 |
| Gln | Arg | Gly | Arg | Phe | Arg | Ala | Met | Val | Glu | Leu | Ala | Arg | Leu | Asp | Arg | |
| | | | | 960 | | | | | 965 | | | | | 970 | | |
| AGG | CGG | CCG | GGG | AGC | AGC | GAC | AGG | GTC | CTC | TTC | GCG | CGG | TTC | TCG | AAG | 2980 |
| Arg | Arg | Pro | Gly | Ser | Ser | Asp | Arg | Val | Leu | Phe | Ala | Arg | Phe | Ser | Lys | |
| | | | 975 | | | | | 980 | | | | | 985 | | | |
| ACC | GAG | GGC | GGA | GCG | AGG | CGG | GCT | TCT | CCA | GAC | CAA | GAA | GCT | GAG | GAC | 3028 |
| Thr | Glu | Gly | Gly | Ala | Arg | Arg | Ala | Ser | Pro | Asp | Gln | Glu | Ala | Glu | Asp | |
| | | 990 | | | | | 995 | | | | | 1000 | | | | |

| | |
|---|---|
| CTG TGG CTG AGC CCG CTG ACC ATG GAA GAT CTT GTC TGC TAC AGC TTC<br>Leu Trp Leu Ser Pro Leu Thr Met Glu Asp Leu Val Cys Tyr Ser Phe<br>1005               1010               1015 | 3076 |
| CAG GTG GCC AGA GGG ATG GAG TTC CTG GCT TCC CGA AAG TGC ATC CAC<br>Gln Val Ala Arg Gly Met Glu Phe Leu Ala Ser Arg Lys Cys Ile His<br>1020              1025           1030           1035 | 3124 |
| AGA GAC CTG GCT GCT CGG AAC ATT CTG CTG TCG GAA AGC GAC GTG GTG<br>Arg Asp Leu Ala Ala Arg Asn Ile Leu Leu Ser Glu Ser Asp Val Val<br>1040             1045            1050 | 3172 |
| AAG ATC TGT GAC TTT GGC CTT GCC CGG GAC ATC TAC AAA GAC CCT GAC<br>Lys Ile Cys Asp Phe Gly Leu Ala Arg Asp Ile Tyr Lys Asp Pro Asp<br>1055             1060            1065 | 3220 |
| TAC GTC CGC AAG GGC AGT GCC CGG CTG CCC CTG AAG TGG ATG GCC CCT<br>Tyr Val Arg Lys Gly Ser Ala Arg Leu Pro Leu Lys Trp Met Ala Pro<br>1070             1075            1080 | 3268 |
| GAA AGC ATC TTC GAC AAG GTG TAC ACC ACG CAG AGT GAC GTG TGG TCC<br>Glu Ser Ile Phe Asp Lys Val Tyr Thr Thr Gln Ser Asp Val Trp Ser<br>1085             1090            1095 | 3316 |
| TTT GGG GTG CTT CTC TGG GAG ATC TTC TCT CTG GGG GCC TCC CCG TAC<br>Phe Gly Val Leu Leu Trp Glu Ile Phe Ser Leu Gly Ala Ser Pro Tyr<br>1100             1105           1110           1115 | 3364 |
| CCT GGG GTG CAG ATC AAT GAG GAG TTC TGC CAG CGG CTG AGA GAC GGC<br>Pro Gly Val Gln Ile Asn Glu Glu Phe Cys Gln Arg Leu Arg Asp Gly<br>1120             1125            1130 | 3412 |
| ACA AGG ATG AGG GCC CCG GAG CTG GCC ACT CCC GCC ATA CGC CGC ATC<br>Thr Arg Met Arg Ala Pro Glu Leu Ala Thr Pro Ala Ile Arg Arg Ile<br>1135             1140            1145 | 3460 |
| ATG CTG AAC TGC TGG TCC GGA GAC CCC AAG GCG AGA CCT GCA TTC TCG<br>Met Leu Asn Cys Trp Ser Gly Asp Pro Lys Ala Arg Pro Ala Phe Ser<br>1150             1155            1160 | 3508 |
| GAG CTG GTG GAG ATC CTG GGG GAC CTG CTC CAG GGC AGG GGC CTG CAA<br>Glu Leu Val Glu Ile Leu Gly Asp Leu Leu Gln Gly Arg Gly Leu Gln<br>1165             1170            1175 | 3556 |
| GAG GAA GAG GAG GTC TGC ATG GCC CCG CGC AGC TCT CAG AGC TCA GAA<br>Glu Glu Glu Glu Val Cys Met Ala Pro Arg Ser Ser Gln Ser Ser Glu<br>1180             1185            1190           1195 | 3604 |
| GAG GGC AGC TTC TCG CAG GTG TCC ACC ATG GCC CTA CAC ATC GCC CAG<br>Glu Gly Ser Phe Ser Gln Val Ser Thr Met Ala Leu His Ile Ala Gln<br>1200             1205            1210 | 3652 |
| GCT GAC GCT GAG GAC AGC CCG CCA AGC CTG CAG CGC CAC AGC CTG GCC<br>Ala Asp Ala Glu Asp Ser Pro Pro Ser Leu Gln Arg His Ser Leu Ala<br>1215             1220            1225 | 3700 |
| GCC AGG TAT TAC AAC TGG GTG TCC TTT CCC GGG TGC CTG GCC AGA GGG<br>Ala Arg Tyr Tyr Asn Trp Val Ser Phe Pro Gly Cys Leu Ala Arg Gly<br>1230             1235            1240 | 3748 |
| GCT GAG ACC CGT GGT TCC TCC AGG ATG AAG ACA TTT GAG GAA TTC CCC<br>Ala Glu Thr Arg Gly Ser Ser Arg Met Lys Thr Phe Glu Glu Phe Pro<br>1245             1250            1255 | 3796 |
| ATG ACC CCA ACG ACC TAC AAA GGC TCT GTG GAC AAC CAG ACA GAC AGT<br>Met Thr Pro Thr Thr Tyr Lys Gly Ser Val Asp Asn Gln Thr Asp Ser<br>1260             1265            1270           1275 | 3844 |
| GGG ATG GTG CTG GCC TCG GAG GAG TTT GAG CAG ATA GAG AGC AGG CAT<br>Gly Met Val Leu Ala Ser Glu Glu Phe Glu Gln Ile Glu Ser Arg His<br>1280             1285            1290 | 3892 |
| AGA CAA GAA AGC GGC TTC AGG TAGCTGAAGC AGAGAGAGAG AAGGCAGCAT<br>Arg Gln Glu Ser Gly Phe Arg<br>1295 | 3943 |
| ACGTCAGCAT TTTCTTCTCT GCACTTATAA GAAAGATCAA AGACTTTAAG ACTTTCGCTA | 4003 |
| TTTCTTCTAC TGCTATCTAC TACAAACTTC AAAGAGGAAC CAGGAGGACA AGAGGAGCAT | 4063 |

```
GAAAGTGGAC AAGGAGTGTG ACCACTGAAG CACCACAGGG AAGGGGTTAG GCCTCCGGAT    4123

GACTGCGGGC AGGCCTGGAT AATATCCAGC CTCCCACAAG AAGCTGGTGG AGCAGAGTGT    4183

TCCCTGACTC CT                                                         4195
```

( 2 ) INFORMATION FOR SEQ ID NO:2:

( i ) SEQUENCE CHARACTERISTICS:
        ( A ) LENGTH: 1298 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Gln   Arg   Gly   Ala   Ala   Leu   Cys   Leu   Arg   Leu   Trp   Leu   Cys   Leu   Gly
 1                  5                            10                             15

Leu   Leu   Asp   Gly   Leu   Val   Ser   Gly   Tyr   Ser   Met   Thr   Pro   Pro   Thr   Leu
              20                            25                       30

Asn   Ile   Thr   Glu   Glu   Ser   His   Val   Ile   Asp   Thr   Gly   Asp   Ser   Leu   Ser
        35                            40                            45

Ile   Ser   Cys   Arg   Gly   Gln   His   Pro   Leu   Glu   Trp   Ala   Trp   Pro   Gly   Ala
      50                            55                            60

Gln   Glu   Ala   Pro   Ala   Thr   Gly   Asp   Lys   Asp   Ser   Glu   Asp   Thr   Gly   Val
65                            70                            75                             80

Val   Arg   Asp   Cys   Glu   Gly   Thr   Asp   Ala   Arg   Pro   Tyr   Cys   Lys   Val   Leu
                    85                            90                             95

Leu   Leu   His   Glu   Val   His   Ala   Asn   Asp   Thr   Gly   Ser   Tyr   Val   Cys   Tyr
              100                           105                           110

Tyr   Lys   Tyr   Ile   Lys   Ala   Arg   Ile   Glu   Gly   Thr   Thr   Ala   Ala   Ser   Ser
        115                           120                           125

Tyr   Val   Phe   Val   Arg   Asp   Phe   Glu   Gln   Pro   Phe   Ile   Asn   Lys   Pro   Asp
      130                           135                           140

Thr   Leu   Leu   Val   Asn   Arg   Lys   Asp   Ala   Met   Trp   Val   Pro   Cys   Leu   Val
145                           150                           155                            160

Ser   Ile   Pro   Gly   Leu   Asn   Val   Thr   Leu   Arg   Ser   Gln   Ser   Ser   Val   Leu
                    165                           170                           175

Trp   Pro   Asp   Gly   Gln   Glu   Val   Val   Trp   Asp   Asp   Arg   Arg   Gly   Met   Leu
              180                           185                           190

Val   Ser   Thr   Pro   Leu   Leu   His   Asp   Ala   Leu   Tyr   Leu   Gln   Cys   Glu   Thr
        195                           200                           205

Thr   Trp   Gly   Asp   Gln   Asp   Phe   Leu   Ser   Asn   Pro   Phe   Leu   Val   His   Ile
      210                           215                           220

Thr   Gly   Asn   Glu   Leu   Tyr   Asp   Ile   Gln   Leu   Leu   Pro   Arg   Lys   Ser   Leu
225                           230                           235                            240

Glu   Leu   Leu   Val   Gly   Glu   Lys   Leu   Val   Leu   Asn   Cys   Thr   Val   Trp   Ala
                    245                           250                           255

Glu   Phe   Asn   Ser   Gly   Val   Thr   Phe   Asp   Trp   Asp   Tyr   Pro   Gly   Lys   Gln
              260                           265                           270

Ala   Glu   Arg   Gly   Lys   Trp   Val   Pro   Glu   Arg   Arg   Ser   Gln   Gln   Thr   His
        275                           280                           285

Thr   Glu   Leu   Ser   Ser   Ile   Leu   Thr   Ile   His   Asn   Val   Ser   Gln   His   Asp
      290                           295                           300

Leu   Gly   Ser   Tyr   Val   Cys   Lys   Ala   Asn   Asn   Gly   Ile   Gln   Arg   Phe   Arg
305                           310                           315                            320

Glu   Ser   Thr   Glu   Val   Ile   Val   His   Glu   Asn   Pro   Phe   Ile   Ser   Val   Glu
```

-continued

```
                          325                       330                       335
Trp  Leu  Lys  Gly  Pro  Ile  Leu  Glu  Ala  Thr  Ala  Gly  Asp  Glu  Leu  Val
                    340                       345                       350
Lys  Leu  Pro  Val  Lys  Leu  Ala  Ala  Tyr  Pro  Pro  Pro  Glu  Phe  Gln  Trp
               355                       360                       365
Tyr  Lys  Asp  Gly  Lys  Ala  Leu  Ser  Gly  Arg  His  Ser  Pro  His  Ala  Leu
          370                       375                       380
Val  Leu  Lys  Glu  Val  Thr  Glu  Ala  Ser  Thr  Gly  Thr  Tyr  Thr  Leu  Ala
385                       390                       395                       400
Leu  Trp  Asn  Ser  Ala  Ala  Gly  Leu  Arg  Arg  Asn  Ile  Ser  Leu  Glu  Leu
                    405                       410                       415
Val  Val  Asn  Val  Pro  Pro  Gln  Ile  His  Glu  Lys  Glu  Ala  Ser  Ser  Pro
                    420                       425                       430
Ser  Ile  Tyr  Ser  Arg  His  Ser  Arg  Gln  Ala  Leu  Thr  Cys  Thr  Ala  Tyr
          435                       440                       445
Gly  Val  Pro  Leu  Pro  Leu  Ser  Ile  Gln  Trp  His  Trp  Arg  Pro  Trp  Thr
     450                       455                       460
Pro  Cys  Lys  Met  Phe  Ala  Gln  Arg  Ser  Leu  Arg  Arg  Arg  Gln  Gln  Gln
465                       470                       475                       480
Asp  Leu  Met  Pro  Gln  Cys  Arg  Asp  Trp  Arg  Ala  Val  Thr  Thr  Gln  Asp
                    485                       490                       495
Ala  Val  Asn  Pro  Ile  Glu  Ser  Leu  Asp  Thr  Trp  Thr  Glu  Phe  Val  Glu
                    500                       505                       510
Gly  Lys  Asn  Lys  Thr  Val  Ser  Lys  Leu  Val  Ile  Gln  Asn  Ala  Asn  Val
               515                       520                       525
Ser  Ala  Met  Tyr  Lys  Cys  Val  Val  Ser  Asn  Lys  Val  Gly  Gln  Asp  Glu
     530                       535                       540
Arg  Leu  Ile  Tyr  Phe  Tyr  Val  Thr  Thr  Ile  Pro  Asp  Gly  Phe  Thr  Ile
545                       550                       555                       560
Glu  Ser  Lys  Pro  Ser  Glu  Glu  Leu  Leu  Glu  Gly  Gln  Pro  Val  Leu  Leu
                    565                       570                       575
Ser  Cys  Gln  Ala  Asp  Ser  Tyr  Lys  Tyr  Glu  His  Leu  Arg  Trp  Tyr  Arg
                    580                       585                       590
Leu  Asn  Leu  Ser  Thr  Leu  His  Asp  Ala  His  Gly  Asn  Pro  Leu  Leu  Leu
          595                       600                       605
Asp  Cys  Lys  Asn  Val  His  Leu  Phe  Ala  Thr  Pro  Leu  Ala  Ala  Ser  Leu
     610                       615                       620
Glu  Glu  Val  Ala  Pro  Gly  Ala  Arg  His  Ala  Thr  Leu  Ser  Leu  Ser  Ile
625                       630                       635                       640
Pro  Arg  Val  Ala  Pro  Glu  His  Glu  Gly  His  Tyr  Val  Cys  Glu  Val  Gln
                    645                       650                       655
Asp  Arg  Arg  Ser  His  Asp  Lys  His  Cys  His  Lys  Lys  Tyr  Leu  Ser  Val
                    660                       665                       670
Gln  Ala  Leu  Glu  Ala  Pro  Arg  Leu  Thr  Gln  Asn  Leu  Thr  Asp  Leu  Leu
          675                       680                       685
Val  Asn  Val  Ser  Asp  Ser  Leu  Glu  Met  Gln  Cys  Leu  Val  Ala  Gly  Ala
     690                       695                       700
His  Ala  Pro  Ser  Ile  Val  Trp  Tyr  Lys  Asp  Glu  Arg  Leu  Leu  Glu  Glu
705                       710                       715                       720
Lys  Ser  Gly  Val  Asp  Leu  Ala  Asp  Ser  Asn  Gln  Lys  Leu  Ser  Ile  Gln
                    725                       730                       735
Arg  Val  Arg  Glu  Glu  Asp  Ala  Gly  Arg  Tyr  Leu  Cys  Ser  Val  Cys  Asn
                    740                       745                       750
```

| | | | | | | | | | | | | | |
|---|---|---|---|---|---|---|---|---|---|---|---|---|---|
|Ala|Lys|Gly|Cys|Val|Asn|Ser|Ser|Ala|Ser|Val|Ala|Val|Glu|Gly|Ser|
| |755| | | | |760| | | |765| | | | | |
|Glu|Asp|Lys|Gly|Ser|Met|Glu|Ile|Val|Ile|Leu|Val|Gly|Thr|Gly|Val|
| |770| | | |775| | | | |780| | | | | |
|Ile|Ala|Val|Phe|Phe|Trp|Val|Leu|Leu|Leu|Leu|Ile|Phe|Cys|Asn|Met|
|785| | | | |790| | | | |795| | | | |800|
|Arg|Arg|Pro|Ala|His|Ala|Asp|Ile|Lys|Thr|Gly|Tyr|Leu|Ser|Ile|Ile|
| | | | |805| | | | |810| | | | |815| |
|Met|Asp|Pro|Gly|Glu|Val|Pro|Leu|Glu|Glu|Gln|Cys|Glu|Tyr|Leu|Ser|
| | | |820| | | | |825| | | | |830| | |
|Tyr|Asp|Ala|Ser|Gln|Trp|Glu|Phe|Pro|Arg|Glu|Arg|Leu|His|Leu|Gly|
| | |835| | | | |840| | | | |845| | | |
|Arg|Val|Leu|Gly|Tyr|Gly|Ala|Phe|Gly|Lys|Val|Val|Glu|Ala|Ser|Ala|
| |850| | | | |855| | | | |860| | | | |
|Phe|Gly|Ile|His|Lys|Gly|Ser|Ser|Cys|Asp|Thr|Val|Ala|Val|Lys|Met|
|865| | | | |870| | | | |875| | | | |880|
|Leu|Lys|Glu|Gly|Ala|Thr|Ala|Ser|Glu|His|Arg|Ala|Leu|Met|Ser|Glu|
| | | | |885| | | | |890| | | | |895| |
|Leu|Lys|Ile|Leu|Ile|His|Ile|Gly|Asn|His|Leu|Asn|Val|Val|Asn|Leu|
| | | |900| | | | |905| | | | |910| | |
|Leu|Gly|Ala|Cys|Thr|Lys|Pro|Gln|Gly|Pro|Leu|Met|Val|Ile|Val|Glu|
| | |915| | | | |920| | | | |925| | | |
|Phe|Cys|Lys|Tyr|Gly|Asn|Leu|Ser|Asn|Phe|Leu|Arg|Ala|Lys|Arg|Asp|
| |930| | | | |935| | | | |940| | | | |
|Ala|Phe|Ser|Pro|Cys|Ala|Glu|Lys|Ser|Pro|Glu|Gln|Arg|Gly|Arg|Phe|
|945| | | | |950| | | | |955| | | | |960|
|Arg|Ala|Met|Val|Glu|Leu|Ala|Arg|Leu|Asp|Arg|Arg|Arg|Pro|Gly|Ser|
| | | | |965| | | | |970| | | | |975| |
|Ser|Asp|Arg|Val|Leu|Phe|Ala|Arg|Phe|Ser|Lys|Thr|Glu|Gly|Gly|Ala|
| | | |980| | | | |985| | | | |990| | |
|Arg|Arg|Ala|Ser|Pro|Asp|Gln|Glu|Ala|Glu|Asp|Leu|Trp|Leu|Ser|Pro|
| | |995| | | | |1000| | | | |1005| | | |
|Leu|Thr|Met|Glu|Asp|Leu|Val|Cys|Tyr|Ser|Phe|Gln|Val|Ala|Arg|Gly|
| |1010| | | | |1015| | | | |1020| | | | |
|Met|Glu|Phe|Leu|Ala|Ser|Arg|Lys|Cys|Ile|His|Arg|Asp|Leu|Ala|Ala|
|1025| | | | |1030| | | | |1035| | | | |1040|
|Arg|Asn|Ile|Leu|Leu|Ser|Glu|Ser|Asp|Val|Val|Lys|Ile|Cys|Asp|Phe|
| | | | |1045| | | | |1050| | | | |1055| |
|Gly|Leu|Ala|Arg|Asp|Ile|Tyr|Lys|Asp|Pro|Asp|Tyr|Val|Arg|Lys|Gly|
| | | |1060| | | | |1065| | | | |1070| | |
|Ser|Ala|Arg|Leu|Pro|Leu|Lys|Trp|Met|Ala|Pro|Glu|Ser|Ile|Phe|Asp|
| | |1075| | | | |1080| | | | |1085| | | |
|Lys|Val|Tyr|Thr|Thr|Gln|Ser|Asp|Val|Trp|Ser|Phe|Gly|Val|Leu|Leu|
| |1090| | | | |1095| | | | |1100| | | | |
|Trp|Glu|Ile|Phe|Ser|Leu|Gly|Ala|Ser|Pro|Tyr|Pro|Gly|Val|Gln|Ile|
|1105| | | | |1110| | | | |1115| | | | |1120|
|Asn|Glu|Glu|Phe|Cys|Gln|Arg|Leu|Arg|Asp|Gly|Thr|Arg|Met|Arg|Ala|
| | | | |1125| | | | |1130| | | | |1135| |
|Pro|Glu|Leu|Ala|Thr|Pro|Ala|Ile|Arg|Arg|Ile|Met|Leu|Asn|Cys|Trp|
| | | |1140| | | | |1145| | | | |1150| | |
|Ser|Gly|Asp|Pro|Lys|Ala|Arg|Pro|Ala|Phe|Ser|Glu|Leu|Val|Glu|Ile|
| | |1155| | | | |1160| | | | |1165| | | |
|Leu|Gly|Asp|Leu|Leu|Gln|Gly|Arg|Gly|Leu|Gln|Glu|Glu|Glu|Glu|Val|
| |1170| | | | |1175| | | | |1180| | | | |

```
Cys Met Ala Pro Arg Ser Ser Gln Ser Ser Glu Glu Gly Ser Phe Ser
1185                1190                1195                1200

Gln Val Ser Thr Met Ala Leu His Ile Ala Gln Ala Asp Ala Glu Asp
                1205                1210                1215

Ser Pro Pro Ser Leu Gln Arg His Ser Leu Ala Ala Arg Tyr Tyr Asn
            1220                1225                1230

Trp Val Ser Phe Pro Gly Cys Leu Ala Arg Gly Ala Glu Thr Arg Gly
            1235                1240                1245

Ser Ser Arg Met Lys Thr Phe Glu Glu Phe Pro Met Thr Pro Thr Thr
        1250                1255                1260

Tyr Lys Gly Ser Val Asp Asn Gln Thr Asp Ser Gly Met Val Leu Ala
1265                1270                1275                1280

Ser Glu Glu Phe Glu Gln Ile Glu Ser Arg His Arg Gln Glu Ser Gly
                1285                1290                1295

Phe Arg
```

( 2 ) INFORMATION FOR SEQ ID NO:3:

( i ) SEQUENCE CHARACTERISTICS:
        ( A ) LENGTH: 4795 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 20..4111

( x i ) SEQUENCE DESCRIPTION: SEQ ID NO:3:

```
CCACGCGCAG CGGCCGGAG ATG CAG CGG GGC GCC GCG CTG TGC CTG CGA CTG          52
                    Met Gln Arg Gly Ala Ala Leu Cys Leu Arg Leu
                     1           5                      10

TGG CTC TGC CTG GGA CTC CTG GAC GGC CTG GTG AGT GGC TAC TCC ATG         100
Trp Leu Cys Leu Gly Leu Leu Asp Gly Leu Val Ser Gly Tyr Ser Met
         15                  20                  25

ACC CCC CCG ACC TTG AAC ATC ACG GAG GAG TCA CAC GTC ATC GAC ACC         148
Thr Pro Pro Thr Leu Asn Ile Thr Glu Glu Ser His Val Ile Asp Thr
         30                  35                  40

GGT GAC AGC CTG TCC ATC TCC TGC AGG GGA CAG CAC CCC CTC GAG TGG         196
Gly Asp Ser Leu Ser Ile Ser Cys Arg Gly Gln His Pro Leu Glu Trp
     45                  50                  55

GCT TGG CCA GGA GCT CAG GAG GCG CCA GCC ACC GGA GAC AAG GAC AGC         244
Ala Trp Pro Gly Ala Gln Glu Ala Pro Ala Thr Gly Asp Lys Asp Ser
60                  65                  70                  75

GAG GAC ACG GGG GTG GTG CGA GAC TGC GAG GGC ACA GAC GCC AGG CCC         292
Glu Asp Thr Gly Val Val Arg Asp Cys Glu Gly Thr Asp Ala Arg Pro
             80                  85                  90

TAC TGC AAG GTG TTG CTG CTG CAC GAG GTA CAT GCC AAC GAC ACA GGC         340
Tyr Cys Lys Val Leu Leu Leu His Glu Val His Ala Asn Asp Thr Gly
         95                 100                 105

AGC TAC GTC TGC TAC TAC AAG TAC ATC AAG GCA CGC ATC GAG GGC ACC         388
Ser Tyr Val Cys Tyr Tyr Lys Tyr Ile Lys Ala Arg Ile Glu Gly Thr
         110                 115                 120

ACG GCC GCC AGC TCC TAC GTG TTC GTG AGA GAC TTT GAG CAG CCA TTC         436
Thr Ala Ala Ser Ser Tyr Val Phe Val Arg Asp Phe Glu Gln Pro Phe
     125                 130                 135

ATC AAC AAG CCT GAC ACG CTC TTG GTC AAC AGG AAG GAC GCC ATG TGG         484
Ile Asn Lys Pro Asp Thr Leu Leu Val Asn Arg Lys Asp Ala Met Trp
140                 145                 150                 155
```

| | | | | | | | | | | | | | | | | |
|---|---|---|---|---|---|---|---|---|---|---|---|---|---|---|---|---|
| GTG | CCC | TGT | CTG | GTG | TCC | ATC | CCC | GGC | CTC | AAT | GTC | ACG | CTG | CGC | TCG | 532 |
| Val | Pro | Cys | Leu | Val | Ser | Ile | Pro | Gly | Leu | Asn | Val | Thr | Leu | Arg | Ser | |
| | | | | 160 | | | | 165 | | | | | | 170 | | |
| CAA | AGC | TCG | GTG | CTG | TGG | CCA | GAC | GGG | CAG | GAG | GTG | GTG | TGG | GAT | GAC | 580 |
| Gln | Ser | Ser | Val | Leu | Trp | Pro | Asp | Gly | Gln | Glu | Val | Val | Trp | Asp | Asp | |
| | | | 175 | | | | | 180 | | | | | 185 | | | |
| CGG | CGG | GGC | ATG | CTC | GTG | TCC | ACG | CCA | CTG | CTG | CAC | GAT | GCC | CTG | TAC | 628 |
| Arg | Arg | Gly | Met | Leu | Val | Ser | Thr | Pro | Leu | Leu | His | Asp | Ala | Leu | Tyr | |
| | | 190 | | | | | 195 | | | | | 200 | | | | |
| CTG | CAG | TGC | GAG | ACC | ACC | TGG | GGA | GAC | CAG | GAC | TTC | CTT | TCC | AAC | CCC | 676 |
| Leu | Gln | Cys | Glu | Thr | Thr | Trp | Gly | Asp | Gln | Asp | Phe | Leu | Ser | Asn | Pro | |
| | 205 | | | | | 210 | | | | | 215 | | | | | |
| TTC | CTG | GTG | CAC | ATC | ACA | GGC | AAC | GAG | CTC | TAT | GAC | ATC | CAG | CTG | TTG | 724 |
| Phe | Leu | Val | His | Ile | Thr | Gly | Asn | Glu | Leu | Tyr | Asp | Ile | Gln | Leu | Leu | |
| 220 | | | | | 225 | | | | | 230 | | | | | 235 | |
| CCC | AGG | AAG | TCG | CTG | GAG | CTG | CTG | GTA | GGG | GAG | AAG | CTG | GTC | CTG | AAC | 772 |
| Pro | Arg | Lys | Ser | Leu | Glu | Leu | Leu | Val | Gly | Glu | Lys | Leu | Val | Leu | Asn | |
| | | | | 240 | | | | | 245 | | | | | 250 | | |
| TGC | ACC | GTG | TGG | GCT | GAG | TTT | AAC | TCA | GGT | GTC | ACC | TTT | GAC | TGG | GAC | 820 |
| Cys | Thr | Val | Trp | Ala | Glu | Phe | Asn | Ser | Gly | Val | Thr | Phe | Asp | Trp | Asp | |
| | | | 255 | | | | | 260 | | | | | 265 | | | |
| TAC | CCA | GGG | AAG | CAG | GCA | GAG | CGG | GGT | AAG | TGG | GTG | CCC | GAG | CGA | CGC | 868 |
| Tyr | Pro | Gly | Lys | Gln | Ala | Glu | Arg | Gly | Lys | Trp | Val | Pro | Glu | Arg | Arg | |
| | | 270 | | | | | 275 | | | | | 280 | | | | |
| TCC | CAG | CAG | ACC | CAC | ACA | GAA | CTC | TCC | AGC | ATC | CTG | ACC | ATC | CAC | AAC | 916 |
| Ser | Gln | Gln | Thr | His | Thr | Glu | Leu | Ser | Ser | Ile | Leu | Thr | Ile | His | Asn | |
| | 285 | | | | | 290 | | | | | 295 | | | | | |
| GTC | AGC | CAG | CAC | GAC | CTG | GGC | TCG | TAT | GTG | TGC | AAG | GCC | AAC | AAC | GGC | 964 |
| Val | Ser | Gln | His | Asp | Leu | Gly | Ser | Tyr | Val | Cys | Lys | Ala | Asn | Asn | Gly | |
| 300 | | | | | 305 | | | | | 310 | | | | | 315 | |
| ATC | CAG | CGA | TTT | CGG | GAG | AGC | ACC | GAG | GTC | ATT | GTG | CAT | GAA | AAT | CCC | 1012 |
| Ile | Gln | Arg | Phe | Arg | Glu | Ser | Thr | Glu | Val | Ile | Val | His | Glu | Asn | Pro | |
| | | | | 320 | | | | | 325 | | | | | 330 | | |
| TTC | ATC | AGC | GTC | GAG | TGG | CTC | AAA | GGA | CCC | ATC | CTG | GAG | GCC | ACG | GCA | 1060 |
| Phe | Ile | Ser | Val | Glu | Trp | Leu | Lys | Gly | Pro | Ile | Leu | Glu | Ala | Thr | Ala | |
| | | | 335 | | | | | 340 | | | | | 345 | | | |
| GGA | GAC | GAG | CTG | GTG | AAG | CTG | CCC | GTG | AAG | CTG | GCA | GCG | TAC | CCC | CCG | 1108 |
| Gly | Asp | Glu | Leu | Val | Lys | Leu | Pro | Val | Lys | Leu | Ala | Ala | Tyr | Pro | Pro | |
| | | 350 | | | | | 355 | | | | | 360 | | | | |
| CCC | GAG | TTC | CAG | TGG | TAC | AAG | GAT | GGA | AAG | GCA | CTG | TCC | GGG | CGC | CAC | 1156 |
| Pro | Glu | Phe | Gln | Trp | Tyr | Lys | Asp | Gly | Lys | Ala | Leu | Ser | Gly | Arg | His | |
| | 365 | | | | | 370 | | | | | 375 | | | | | |
| AGT | CCA | CAT | GCC | CTG | GTG | CTC | AAG | GAG | GTG | ACA | GAG | GCC | AGC | ACA | GGC | 1204 |
| Ser | Pro | His | Ala | Leu | Val | Leu | Lys | Glu | Val | Thr | Glu | Ala | Ser | Thr | Gly | |
| 380 | | | | | 385 | | | | | 390 | | | | | 395 | |
| ACC | TAC | ACC | CTC | GCC | CTG | TGG | AAC | TCC | GCT | GCT | GGC | CTG | AGG | CGC | AAC | 1252 |
| Thr | Tyr | Thr | Leu | Ala | Leu | Trp | Asn | Ser | Ala | Ala | Gly | Leu | Arg | Arg | Asn | |
| | | | | 400 | | | | | 405 | | | | | 410 | | |
| ATC | AGC | CTG | GAG | CTG | GTG | GTG | AAT | GTG | CCC | CCC | CAG | ATA | CAT | GAG | AAG | 1300 |
| Ile | Ser | Leu | Glu | Leu | Val | Val | Asn | Val | Pro | Pro | Gln | Ile | His | Glu | Lys | |
| | | | | 415 | | | | | 420 | | | | | 425 | | |
| GAG | GCC | TCC | TCC | CCC | AGC | ATC | TAC | TCG | CGT | CAC | AGC | CGC | CAG | GCC | CTC | 1348 |
| Glu | Ala | Ser | Ser | Pro | Ser | Ile | Tyr | Ser | Arg | His | Ser | Arg | Gln | Ala | Leu | |
| | | 430 | | | | | 435 | | | | | 440 | | | | |
| ACC | TGC | ACG | GCC | TAC | GGG | GTG | CCC | CTG | CCT | CTC | AGC | ATC | CAG | TGG | CAC | 1396 |
| Thr | Cys | Thr | Ala | Tyr | Gly | Val | Pro | Leu | Pro | Leu | Ser | Ile | Gln | Trp | His | |
| | | 445 | | | | | 450 | | | | | 455 | | | | |
| TGG | CGG | CCC | TGG | ACA | CCC | TGC | AAG | ATG | TTT | GCC | CAG | CGT | AGT | CTC | CGG | 1444 |
| Trp | Arg | Pro | Trp | Thr | Pro | Cys | Lys | Met | Phe | Ala | Gln | Arg | Ser | Leu | Arg | |
| 460 | | | | | 465 | | | | | 470 | | | | | 475 | |

| | | | | | | | | | | | | | | | | |
|---|---|---|---|---|---|---|---|---|---|---|---|---|---|---|---|---|
| CGG | CGG | CAG | CAG | CAA | GAC | CTC | ATG | CCA | CAG | TGC | CGT | GAC | TGG | AGG | GCG | 1492 |
| Arg | Arg | Gln | Gln | Gln | Asp | Leu | Met | Pro | Gln | Cys | Arg | Asp | Trp | Arg | Ala | |
| | | | 480 | | | | | 485 | | | | | 490 | | | |
| GTG | ACC | ACG | CAG | GAT | GCC | GTG | AAC | CCC | ATC | GAG | AGC | CTG | GAC | ACC | TGG | 1540 |
| Val | Thr | Thr | Gln | Asp | Ala | Val | Asn | Pro | Ile | Glu | Ser | Leu | Asp | Thr | Trp | |
| | | | 495 | | | | | 500 | | | | | 505 | | | |
| ACC | GAG | TTT | GTG | GAG | GGA | AAG | AAT | AAG | ACT | GTG | AGC | AAG | CTG | GTG | ATC | 1588 |
| Thr | Glu | Phe | Val | Glu | Gly | Lys | Asn | Lys | Thr | Val | Ser | Lys | Leu | Val | Ile | |
| | | 510 | | | | | 515 | | | | | 520 | | | | |
| CAG | AAT | GCC | AAC | GTG | TCT | GCC | ATG | TAC | AAG | TGT | GTG | GTC | TCC | AAC | AAG | 1636 |
| Gln | Asn | Ala | Asn | Val | Ser | Ala | Met | Tyr | Lys | Cys | Val | Val | Ser | Asn | Lys | |
| | 525 | | | | | 530 | | | | | 535 | | | | | |
| GTG | GGC | CAG | GAT | GAG | CGG | CTC | ATC | TAC | TTC | TAT | GTG | ACC | ACC | ATC | CCC | 1684 |
| Val | Gly | Gln | Asp | Glu | Arg | Leu | Ile | Tyr | Phe | Tyr | Val | Thr | Thr | Ile | Pro | |
| 540 | | | | | 545 | | | | | 550 | | | | | 555 | |
| GAC | GGC | TTC | ACC | ATC | GAA | TCC | AAG | CCA | TCC | GAG | GAG | CTA | CTA | GAG | GGC | 1732 |
| Asp | Gly | Phe | Thr | Ile | Glu | Ser | Lys | Pro | Ser | Glu | Glu | Leu | Leu | Glu | Gly | |
| | | | | 560 | | | | | 565 | | | | | 570 | | |
| CAG | CCG | GTG | CTC | CTG | AGC | TGC | CAA | GCC | GAC | AGC | TAC | AAG | TAC | GAG | CAT | 1780 |
| Gln | Pro | Val | Leu | Leu | Ser | Cys | Gln | Ala | Asp | Ser | Tyr | Lys | Tyr | Glu | His | |
| | | | 575 | | | | | 580 | | | | | 585 | | | |
| CTG | CGC | TGG | TAC | CGC | CTC | AAC | CTG | TCC | ACG | CTG | CAC | GAT | GCG | CAC | GGG | 1828 |
| Leu | Arg | Trp | Tyr | Arg | Leu | Asn | Leu | Ser | Thr | Leu | His | Asp | Ala | His | Gly | |
| | | 590 | | | | | 595 | | | | | 600 | | | | |
| AAC | CCG | CTT | CTG | CTC | GAC | TGC | AAG | AAC | GTG | CAT | CTG | TTC | GCC | ACC | CCT | 1876 |
| Asn | Pro | Leu | Leu | Leu | Asp | Cys | Lys | Asn | Val | His | Leu | Phe | Ala | Thr | Pro | |
| | 605 | | | | | 610 | | | | | 615 | | | | | |
| CTG | GCC | GCC | AGC | CTG | GAG | GAG | GTG | GCA | CCT | GGG | GCG | CGC | CAC | GCC | ACG | 1924 |
| Leu | Ala | Ala | Ser | Leu | Glu | Glu | Val | Ala | Pro | Gly | Ala | Arg | His | Ala | Thr | |
| 620 | | | | | 625 | | | | | 630 | | | | | 635 | |
| CTC | AGC | CTG | AGT | ATC | CCC | CGC | GTC | GCG | CCC | GAG | CAC | GAG | GGC | CAC | TAT | 1972 |
| Leu | Ser | Leu | Ser | Ile | Pro | Arg | Val | Ala | Pro | Glu | His | Glu | Gly | His | Tyr | |
| | | | | 640 | | | | | 645 | | | | | 650 | | |
| GTG | TGC | GAA | GTG | CAA | GAC | CGG | CGC | AGC | CAT | GAC | AAG | CAC | TGC | CAC | AAG | 2020 |
| Val | Cys | Glu | Val | Gln | Asp | Arg | Arg | Ser | His | Asp | Lys | His | Cys | His | Lys | |
| | | | 655 | | | | | 660 | | | | | 665 | | | |
| AAG | TAC | CTG | TCG | GTG | CAG | GCC | CTG | GAA | GCC | CCT | CGG | CTC | ACG | CAG | AAC | 2068 |
| Lys | Tyr | Leu | Ser | Val | Gln | Ala | Leu | Glu | Ala | Pro | Arg | Leu | Thr | Gln | Asn | |
| | | 670 | | | | | 675 | | | | | 680 | | | | |
| TTG | ACC | GAC | CTC | CTG | GTG | AAC | GTG | AGC | GAC | TCG | CTG | GAG | ATG | CAG | TGC | 2116 |
| Leu | Thr | Asp | Leu | Leu | Val | Asn | Val | Ser | Asp | Ser | Leu | Glu | Met | Gln | Cys | |
| | 685 | | | | | 690 | | | | | 695 | | | | | |
| TTG | GTG | GCC | GGA | GCG | CAC | GCG | CCC | AGC | ATC | GTG | TGG | TAC | AAA | GAC | GAG | 2164 |
| Leu | Val | Ala | Gly | Ala | His | Ala | Pro | Ser | Ile | Val | Trp | Tyr | Lys | Asp | Glu | |
| 700 | | | | | 705 | | | | | 710 | | | | | 715 | |
| AGG | CTG | CTG | GAG | GAA | AAG | TCT | GGA | GTC | GAC | TTG | GCG | GAC | TCC | AAC | CAG | 2212 |
| Arg | Leu | Leu | Glu | Glu | Lys | Ser | Gly | Val | Asp | Leu | Ala | Asp | Ser | Asn | Gln | |
| | | | | 720 | | | | | 725 | | | | | 730 | | |
| AAG | CTG | AGC | ATC | CAG | CGC | GTG | CGC | GAG | GAG | GAT | GCG | GGA | CGC | TAT | CTG | 2260 |
| Lys | Leu | Ser | Ile | Gln | Arg | Val | Arg | Glu | Glu | Asp | Ala | Gly | Arg | Tyr | Leu | |
| | | | 735 | | | | | 740 | | | | | 745 | | | |
| TGC | AGC | GTG | TGC | AAC | GCC | AAG | GGC | TGC | GTC | AAC | TCC | TCC | GCC | AGC | GTG | 2308 |
| Cys | Ser | Val | Cys | Asn | Ala | Lys | Gly | Cys | Val | Asn | Ser | Ser | Ala | Ser | Val | |
| | | 750 | | | | | 755 | | | | | 760 | | | | |
| GCC | GTG | GAA | GGC | TCC | GAG | GAT | AAG | GGC | AGC | ATG | GAG | ATC | GTG | ATC | CTT | 2356 |
| Ala | Val | Glu | Gly | Ser | Glu | Asp | Lys | Gly | Ser | Met | Glu | Ile | Val | Ile | Leu | |
| | 765 | | | | | 770 | | | | | 775 | | | | | |
| GTC | GGT | ACC | GGC | GTC | ATC | GCT | GTC | TTC | TTC | TGG | GTC | CTC | CTC | CTC | CTC | 2404 |
| Val | Gly | Thr | Gly | Val | Ile | Ala | Val | Phe | Phe | Trp | Val | Leu | Leu | Leu | Leu | |
| 780 | | | | | 785 | | | | | 790 | | | | | 795 | |

| | | | | | | | | | | | | | | | | |
|---|---|---|---|---|---|---|---|---|---|---|---|---|---|---|---|---|
| ATC | TTC | TGT | AAC | ATG | AGG | AGG | CCG | GCC | CAC | GCA | GAC | ATC | AAG | ACG | GGC | 2452 |
| Ile | Phe | Cys | Asn | Met 800 | Arg | Arg | Pro | Ala | His 805 | Ala | Asp | Ile | Lys | Thr 810 | Gly | |
| TAC | CTG | TCC | ATC | ATC | ATG | GAC | CCC | GGG | GAG | GTG | CCT | CTG | GAG | GAG | CAA | 2500 |
| Tyr | Leu | Ser | Ile 815 | Ile | Met | Asp | Pro | Gly 820 | Glu | Val | Pro | Leu | Glu 825 | Glu | Gln | |
| TGC | GAA | TAC | CTG | TCC | TAC | GAT | GCC | AGC | CAG | TGG | GAA | TTC | CCC | CGA | GAG | 2548 |
| Cys | Glu | Tyr 830 | Leu | Ser | Tyr | Asp | Ala | Ser 835 | Gln | Trp | Glu | Phe | Pro 840 | Arg | Glu | |
| CGG | CTG | CAC | CTG | GGG | AGA | GTG | CTC | GGC | TAC | GGC | GCC | TTC | GGG | AAG | GTG | 2596 |
| Arg | Leu | His | Leu 845 | Gly | Arg | Val | Leu | Gly 850 | Tyr | Gly | Ala | Phe 855 | Gly | Lys | Val | |
| GTG | GAA | GCC | TCC | GCT | TTC | GGC | ATC | CAC | AAG | GGC | AGC | AGC | TGT | GAC | ACC | 2644 |
| Val 860 | Glu | Ala | Ser | Ala | Phe 865 | Gly | Ile | His | Lys | Gly 870 | Ser | Ser | Cys | Asp | Thr 875 | |
| GTG | GCC | GTG | AAA | ATG | CTG | AAA | GAG | GGC | GCC | ACG | GCC | AGC | GAG | CAC | CGC | 2692 |
| Val | Ala | Val | Lys | Met 880 | Leu | Lys | Glu | Gly | Ala 885 | Thr | Ala | Ser | Glu | His 890 | Arg | |
| GCG | CTG | ATG | TCG | GAG | CTC | AAG | ATC | CTC | ATT | CAC | ATC | GGC | AAC | CAC | CTC | 2740 |
| Ala | Leu | Met | Ser 895 | Glu | Leu | Lys | Ile | Leu 900 | Ile | His | Ile | Gly | Asn 905 | His | Leu | |
| AAC | GTG | GTC | AAC | CTC | CTC | GGG | GCG | TGC | ACC | AAG | CCG | CAG | GGC | CCC | CTC | 2788 |
| Asn | Val | Val 910 | Asn | Leu | Leu | Gly | Ala 915 | Cys | Thr | Lys | Pro | Gln 920 | Gly | Pro | Leu | |
| ATG | GTG | ATC | GTG | GAG | TTC | TGC | AAG | TAC | GGC | AAC | CTC | TCC | AAC | TTC | CTG | 2836 |
| Met | Val 925 | Ile | Val | Glu | Phe | Cys 930 | Lys | Tyr | Gly | Asn | Leu 935 | Ser | Asn | Phe | Leu | |
| CGC | GCC | AAG | CGG | GAC | GCC | TTC | AGC | CCC | TGC | GCG | GAG | AAG | TCT | CCC | GAG | 2884 |
| Arg | Ala | Lys | Arg 940 | Asp | Ala | Phe | Ser | Pro 945 | Cys | Ala | Glu | Lys | Ser 950 | Pro | Glu 955 | |
| CAG | CGC | GGA | CGC | TTC | CGC | GCC | ATG | GTG | GAG | CTC | GCC | AGG | CTG | GAT | CGG | 2932 |
| Gln | Arg | Gly | Arg | Phe 960 | Arg | Ala | Met | Val 965 | Glu | Leu | Ala | Arg | Leu 970 | Asp | Arg | |
| AGG | CGG | CCG | GGG | AGC | AGC | GAC | AGG | GTC | CTC | TTC | GCG | CGG | TTC | TCG | AAG | 2980 |
| Arg | Arg | Pro | Gly 975 | Ser | Ser | Asp | Arg | Val 980 | Leu | Phe | Ala | Arg | Phe 985 | Ser | Lys | |
| ACC | GAG | GGC | GGA | GCG | AGG | CGG | GCT | TCT | CCA | GAC | CAA | GAA | GCT | GAG | GAC | 3028 |
| Thr | Glu | Gly 990 | Gly | Ala | Arg | Arg | Ala 995 | Ser | Pro | Asp | Gln | Glu 1000 | Ala | Glu | Asp | |
| CTG | TGG | CTG | AGC | CCG | CTG | ACC | ATG | GAA | GAT | CTT | GTC | TGC | TAC | AGC | TTC | 3076 |
| Leu | Trp | Leu | Ser 1005 | Pro | Leu | Thr | Met | Glu 1010 | Asp | Leu | Val | Cys | Tyr 1015 | Ser | Phe | |
| CAG | GTG | GCC | AGA | GGG | ATG | GAG | TTC | CTG | GCT | TCC | CGA | AAG | TGC | ATC | CAC | 3124 |
| Gln | Val | Ala | Arg 1020 | Gly | Met | Glu | Phe 1025 | Leu | Ala | Ser | Arg | Lys 1030 | Cys | Ile | His 1035 | |
| AGA | GAC | CTG | GCT | GCT | CGG | AAC | ATT | CTG | CTG | TCG | GAA | AGC | GAC | GTG | GTG | 3172 |
| Arg | Asp | Leu | Ala | Ala 1040 | Arg | Asn | Ile | Leu | Leu 1045 | Ser | Glu | Ser | Asp | Val 1050 | Val | |
| AAG | ATC | TGT | GAC | TTT | GGC | CTT | GCC | CGG | GAC | ATC | TAC | AAA | GAC | CCT | GAC | 3220 |
| Lys | Ile | Cys | Asp | Phe 1055 | Gly | Leu | Ala | Arg | Asp 1060 | Ile | Tyr | Lys | Asp 1065 | Pro | Asp | |
| TAC | GTC | CGC | AAG | GGC | AGT | GCC | CGG | CTG | CCC | CTG | AAG | TGG | ATG | GCC | CCT | 3268 |
| Tyr | Val | Arg | Lys 1070 | Gly | Ser | Ala | Arg | Leu 1075 | Pro | Leu | Lys | Trp | Met 1080 | Ala | Pro | |
| GAA | AGC | ATC | TTC | GAC | AAG | GTG | TAC | ACC | ACG | CAG | AGT | GAC | GTG | TGG | TCC | 3316 |
| Glu | Ser | Ile 1085 | Phe | Asp | Lys | Val | Tyr 1090 | Thr | Thr | Gln | Ser | Asp 1095 | Val | Trp | Ser | |
| TTT | GGG | GTG | CTT | CTC | TGG | GAG | ATC | TTC | TCT | CTG | GGG | GCC | TCC | CCG | TAC | 3364 |
| Phe | Gly 1100 | Val | Leu | Leu | Trp | Glu 1105 | Ile | Phe | Ser | Leu | Gly 1110 | Ala | Ser | Pro | Tyr 1115 | |

```
CCT GGG GTG CAG ATC AAT GAG GAG TTC TGC CAG CGG CTG AGA GAC GGC     3412
Pro Gly Val Gln Ile Asn Glu Glu Phe Cys Gln Arg Leu Arg Asp Gly
            1120                1125                1130

ACA AGG ATG AGG GCC CCG GAG CTG GCC ACT CCC GCC ATA CGC CGC ATC     3460
Thr Arg Met Arg Ala Pro Glu Leu Ala Thr Pro Ala Ile Arg Arg Ile
        1135                1140                1145

ATG CTG AAC TGC TGG TCC GGA GAC CCC AAG GCG AGA CCT GCA TTC TCG     3508
Met Leu Asn Cys Trp Ser Gly Asp Pro Lys Ala Arg Pro Ala Phe Ser
        1150                1155                1160

GAG CTG GTG GAG ATC CTG GGG GAC CTG CTC CAG GGC AGG GGC CTG CAA     3556
Glu Leu Val Glu Ile Leu Gly Asp Leu Leu Gln Gly Arg Gly Leu Gln
        1165                1170                1175

GAG GAA GAG GAG GTC TGC ATG GCC CCG CGC AGC TCT CAG AGC TCA GAA     3604
Glu Glu Glu Glu Val Cys Met Ala Pro Arg Ser Ser Gln Ser Ser Glu
1180                1185                1190                1195

GAG GGC AGC TTC TCG CAG GTG TCC ACC ATG GCC CTA CAC ATC GCC CAG     3652
Glu Gly Ser Phe Ser Gln Val Ser Thr Met Ala Leu His Ile Ala Gln
            1200                1205                1210

GCT GAC GCT GAG GAC AGC CCG CCA AGC CTG CAG CGC CAC AGC CTG GCC     3700
Ala Asp Ala Glu Asp Ser Pro Pro Ser Leu Gln Arg His Ser Leu Ala
        1215                1220                1225

GCC AGG TAT TAC AAC TGG GTG TCC TTT CCC GGG TGC CTG GCC AGA GGG     3748
Ala Arg Tyr Tyr Asn Trp Val Ser Phe Pro Gly Cys Leu Ala Arg Gly
        1230                1235                1240

GCT GAG ACC CGT GGT TCC TCC AGG ATG AAG ACA TTT GAG GAA TTC CCC     3796
Ala Glu Thr Arg Gly Ser Ser Arg Met Lys Thr Phe Glu Glu Phe Pro
        1245                1250                1255

ATG ACC CCA ACG ACC TAC AAA GGC TCT GTG GAC AAC CAG ACA GAC AGT     3844
Met Thr Pro Thr Thr Tyr Lys Gly Ser Val Asp Asn Gln Thr Asp Ser
1260                1265                1270                1275

GGG ATG GTG CTG GCC TCG GAG GAG TTT GAG CAG ATA GAG AGC AGG CAT     3892
Gly Met Val Leu Ala Ser Glu Glu Phe Glu Gln Ile Glu Ser Arg His
            1280                1285                1290

AGA CAA GAA AGC GGC TTC AGC TGT AAA GGA CCT GGC CAG AAT GTG GCT     3940
Arg Gln Glu Ser Gly Phe Ser Cys Lys Gly Pro Gly Gln Asn Val Ala
        1295                1300                1305

GTG ACC AGG GCA CAC CCT GAC TCC CAA GGG AGG CGG CGG CGG CCT GAG     3988
Val Thr Arg Ala His Pro Asp Ser Gln Gly Arg Arg Arg Arg Pro Glu
        1310                1315                1320

CGG GGG GCC CGA GGA GGC CAG GTG TTT TAC AAC AGC GAG TAT GGG GAG     4036
Arg Gly Ala Arg Gly Gly Gln Val Phe Tyr Asn Ser Glu Tyr Gly Glu
        1325                1330                1335

CTG TCG GAG CCA AGC GAG GAG GAC CAC TGC TCC CCG TCT GCC CGC GTG     4084
Leu Ser Glu Pro Ser Glu Glu Asp His Cys Ser Pro Ser Ala Arg Val
1340                1345                1350                1355

ACT TTC TTC ACA GAC AAC AGC TAC TAAGCAGCAT CGGACAAGAC CCCCAGCACT    4138
Thr Phe Phe Thr Asp Asn Ser Tyr
        1360

TGGGGGTTCA GGCCCGGCAG GGCGGGCAGA GGGCTGGAGG CCCAGGCTGG GAACTCATCT    4198

GGTTGAACTC TGGTGGCACA GGAGTGTCCT CTTCCCTCTC TGCAGACTTC CAGCTAGGA    4258

AGAGCAGGAC TCCAGGCCCA AGGCTCCCGG AATTCCGTCA CCACGACTGG CCAGGGCACG    4318

CTCCAGCTGC CCCGGCCCCT CCCCCTGAGA TTCAGATGTC ATTTAGTTCA GCATCCGCAG    4378

GTGCTGGTCC CGGGGCCAGC ACTTCCATGG GAATGTCTCT TTGGCGACCT CCTTTCATCA    4438

CACTGGGTGG TGGCCTGGTC CCTGTTTTCC CACGAGGAAT CTGTGGGTCT GGGAGTCACA    4498

CAGTGTTGGA GGTTAAGGCA TACGAGAGCA GAGGTCTCCC AAACGCCCTT TCCTCCTCAG    4558

GCACACAGCT ACTCTCCCCA CGAGGGCTGG CTGGCCTCAC CCACCCCTGC ACAGTTGAAG    4618
```

```
GGAGGGGCTG TGTTTCCATC TCAAAGAAGG CATTTGCAGG GTCCTCTTCT GGGCCTGACC        4678

AAACAGCCAA CTAGCCCCTG GGGTGGCCAC CAGTATGACA GTATTATACG CTGGCAACAC        4738

AGAGGCAGCC CGCACACCTG CGCCTGGGTG TTGAGAGCCA TCCTGCAAGT CTTTTTC          4795
```

(2) INFORMATION FOR SEQ ID NO:4:

(i) SEQUENCE CHARACTERISTICS:
        (A) LENGTH: 1363 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gln Arg Gly Ala Ala Leu Cys Leu Arg Leu Trp Leu Cys Leu Gly
 1               5                  10                  15

Leu Leu Asp Gly Leu Val Ser Gly Tyr Ser Met Thr Pro Pro Thr Leu
             20                  25                  30

Asn Ile Thr Glu Glu Ser His Val Ile Asp Thr Gly Asp Ser Leu Ser
             35                  40                  45

Ile Ser Cys Arg Gly Gln His Pro Leu Glu Trp Ala Trp Pro Gly Ala
     50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                 85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
```

-continued

|     |     |     | 325 |     |     |     |     | 330 |     |     |     |     | 335 |     |     |
|---|---|---|---|---|---|---|---|---|---|---|---|---|---|---|---|

Trp Leu Lys Gly Pro Ile Leu Glu Ala Thr Ala Gly Asp Glu Leu Val
                340                     345                 350

Lys Leu Pro Val Lys Leu Ala Ala Tyr Pro Pro Pro Glu Phe Gln Trp
            355                 360                 365

Tyr Lys Asp Gly Lys Ala Leu Ser Gly Arg His Ser Pro His Ala Leu
    370                     375                 380

Val Leu Lys Glu Val Thr Glu Ala Ser Thr Gly Thr Tyr Thr Leu Ala
385                 390                 395                     400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

| | | | | | | | | | | | | |
|---|---|---|---|---|---|---|---|---|---|---|---|---|
|Ala|Lys|Gly 755|Cys|Val|Asn|Ser|Ser 760|Ala|Ser|Val|Ala 765|Val|Glu|Gly|Ser|
|Glu|Asp 770|Lys|Gly|Ser|Met|Glu 775|Ile|Val|Ile|Leu|Val 780|Gly|Thr|Gly|Val|
|Ile 785|Ala|Val|Phe|Phe|Trp 790|Val|Leu|Leu|Leu|Leu 795|Ile|Phe|Cys|Asn|Met 800|
|Arg|Arg|Pro|Ala|His 805|Ala|Asp|Ile|Lys|Thr 810|Gly|Tyr|Leu|Ser|Ile 815|Ile|
|Met|Asp|Pro|Gly 820|Glu|Val|Pro|Leu|Glu 825|Glu|Gln|Cys|Glu 830|Tyr|Leu|Ser|
|Tyr|Asp|Ala 835|Ser|Gln|Trp|Glu|Phe 840|Pro|Arg|Glu|Arg|Leu 845|His|Leu|Gly|
|Arg|Val 850|Leu|Gly|Tyr|Gly|Ala 855|Phe|Gly|Lys|Val|Val 860|Glu|Ala|Ser|Ala|
|Phe 865|Gly|Ile|His|Lys|Gly 870|Ser|Ser|Cys|Asp|Thr 875|Val|Ala|Val|Lys|Met 880|
|Leu|Lys|Glu|Gly|Ala 885|Thr|Ala|Ser|Glu|His 890|Arg|Ala|Leu|Met|Ser 895|Glu|
|Leu|Lys|Ile|Leu 900|Ile|His|Ile|Gly|Asn 905|His|Leu|Asn|Val|Val 910|Asn|Leu|
|Leu|Gly|Ala|Cys 915|Thr|Lys|Pro|Gln|Gly 920|Pro|Leu|Met|Val 925|Ile|Val|Glu|
|Phe|Cys 930|Lys|Tyr|Gly|Asn|Leu 935|Ser|Asn|Phe|Leu|Arg 940|Ala|Lys|Arg|Asp|
|Ala 945|Phe|Ser|Pro|Cys|Ala 950|Glu|Lys|Ser|Pro|Glu 955|Gln|Arg|Gly|Arg|Phe 960|
|Arg|Ala|Met|Val|Glu 965|Leu|Ala|Arg|Leu|Asp 970|Arg|Arg|Arg|Pro 975|Gly|Ser|
|Ser|Asp|Arg|Val 980|Leu|Phe|Ala|Arg|Phe 985|Ser|Lys|Thr|Glu|Gly 990|Gly|Ala|
|Arg|Arg|Ala 995|Ser|Pro|Asp|Gln|Glu 1000|Ala|Glu|Asp|Leu 1005|Trp|Leu|Ser|Pro|
|Leu|Thr|Met 1010|Glu|Asp|Leu|Val 1015|Cys|Tyr|Ser|Phe|Gln 1020|Val|Ala|Arg|Gly|
|Met 1025|Glu|Phe|Leu|Ala|Ser 1030|Arg|Lys|Cys|Ile|His 1035|Arg|Asp|Leu|Ala|Ala 1040|
|Arg|Asn|Ile|Leu|Leu 1045|Ser|Glu|Ser|Asp|Val 1050|Val|Lys|Ile|Cys|Asp 1055|Phe|
|Gly|Leu|Ala|Arg 1060|Asp|Ile|Tyr|Lys|Asp 1065|Pro|Asp|Tyr|Val|Arg 1070|Lys|Gly|
|Ser|Ala|Arg|Leu 1075|Pro|Leu|Lys|Trp|Met 1080|Ala|Pro|Glu|Ser 1085|Ile|Phe|Asp|
|Lys|Val|Tyr 1090|Thr|Thr|Gln|Ser|Asp 1095|Val|Trp|Ser|Phe 1100|Gly|Val|Leu|Leu|
|Trp|Glu|Ile|Phe 1105|Ser|Leu|Gly|Ala|Ser 1110|Pro|Tyr|Pro|Gly 1115|Val|Gln|Ile 1120|
|Asn|Glu|Glu|Phe|Cys 1125|Gln|Arg|Leu|Arg|Asp 1130|Gly|Thr|Arg|Met 1135|Arg|Ala|
|Pro|Glu|Leu|Ala|Thr 1140|Pro|Ala|Ile|Arg|Arg 1145|Ile|Met|Leu|Asn|Cys 1150|Trp|
|Ser|Gly|Asp|Pro 1155|Lys|Ala|Arg|Pro|Ala 1160|Phe|Ser|Glu|Leu 1165|Val|Glu|Ile|
|Leu|Gly|Asp|Leu 1170|Leu|Gln|Gly|Arg|Gly 1175|Leu|Gln|Glu|Glu|Glu 1180|Val|

Cys Met Ala Pro Arg Ser Ser Gln Ser Ser Glu Glu Gly Ser Phe Ser
1185                1190                1195                1200

Gln Val Ser Thr Met Ala Leu His Ile Ala Gln Ala Asp Ala Glu Asp
            1205                1210                1215

Ser Pro Pro Ser Leu Gln Arg His Ser Leu Ala Ala Arg Tyr Tyr Asn
            1220                1225                1230

Trp Val Ser Phe Pro Gly Cys Leu Ala Arg Gly Ala Glu Thr Arg Gly
            1235                1240                1245

Ser Ser Arg Met Lys Thr Phe Glu Glu Phe Pro Met Thr Pro Thr Thr
            1250                1255                1260

Tyr Lys Gly Ser Val Asp Asn Gln Thr Asp Ser Gly Met Val Leu Ala
1265                1270                1275                1280

Ser Glu Glu Phe Glu Gln Ile Glu Ser Arg His Arg Gln Glu Ser Gly
                1285                1290                1295

Phe Ser Cys Lys Gly Pro Gly Gln Asn Val Ala Val Thr Arg Ala His
                1300                1305                1310

Pro Asp Ser Gln Gly Arg Arg Arg Arg Pro Glu Arg Gly Ala Arg Gly
            1315                1320                1325

Gly Gln Val Phe Tyr Asn Ser Glu Tyr Gly Glu Leu Ser Glu Pro Ser
1330                1335                1340

Glu Glu Asp His Cys Ser Pro Ser Ala Arg Val Thr Phe Phe Thr Asp
1345                1350                1355                1360

Asn Ser Tyr ( 2 ) INFORMATION FOR SEQ ID NO:5:

( i ) SEQUENCE CHARACTERISTICS:
( A ) LENGTH: 1311 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Asn Asn Asn Asn Asn Asn Met Val Ser Lys Glu Ser Glu Arg Leu
65                  70                  75                  80

Ser Ile Thr Lys Ser Ala Cys Gly Arg Asn Gly Lys Gln Phe Cys Ser
                85                  90                  95

Thr Leu Thr Leu Asn Thr Ala Gln Ala Asn His Thr Gly Phe Tyr Ser
                100                 105                 110

Cys Lys Tyr Leu Ala Val Pro Thr Ser Lys Lys Lys Glu Thr Glu Ser
            115                 120                 125

Ala Ile Tyr Ile Phe Ile Ser Asp Thr Gly Arg Pro Phe Val Glu Met
        130                 135                 140

Tyr Ser Glu Ile Pro Glu Ile Ile His Met Thr Glu Gly Arg Glu Leu
145                 150                 155                 160

Val Ile Pro Cys Arg Val Thr Ser Pro Asn Ile Thr Val Thr Leu Lys

-continued

|     |     |     | 165 |     |     |     |     | 170 |     |     |     |     | 175 |     |     |
|-----|-----|-----|-----|-----|-----|-----|-----|-----|-----|-----|-----|-----|-----|-----|-----|
| Lys | Phe | Pro | Leu | Asp | Thr | Leu | Ile | Pro | Asp | Gly | Lys | Arg | Ile | Ile | Trp |
|     |     |     | 180 |     |     |     |     | 185 |     |     |     |     | 190 |     |     |
| Asp | Ser | Arg | Lys | Gly | Phe | Ile | Ile | Ser | Asn | Ala | Thr | Tyr | Lys | Glu | Ile |
|     |     |     | 195 |     |     |     |     | 200 |     |     |     |     | 205 |     |     |
| Gly | Leu | Leu | Thr | Cys | Glu | Ala | Thr | Val | Asn | Gly | His | Leu | Tyr | Lys | Thr |
|     |     |     | 210 |     |     |     |     | 215 |     |     |     |     | 220 |     |     |
| Asn | Asn | Tyr | Leu | Thr | His | Arg | Gln | Thr | Asn | Thr | Ile | Ile | Asp | Val | Gln |
| 225 |     |     |     |     | 230 |     |     |     |     | 235 |     |     |     |     | 240 |
| Ile | Ser | Thr | Pro | Arg | Pro | Val | Lys | Leu | Leu | Arg | Gly | His | Thr | Leu | Val |
|     |     |     |     | 245 |     |     |     |     | 250 |     |     |     |     | 255 |     |
| Leu | Asn | Cys | Thr | Ala | Thr | Thr | Pro | Leu | Asn | Thr | Arg | Val | Gln | Met | Thr |
|     |     |     | 260 |     |     |     |     | 265 |     |     |     |     | 270 |     |     |
| Trp | Ser | Tyr | Pro | Asp | Asn | Asn | Asn | Glu | Lys | Asn | Lys | Arg | Ala | Ser | Val |
|     |     | 275 |     |     |     |     |     | 280 |     |     |     |     | 285 |     |     |
| Arg | Arg | Arg | Ile | Asp | Gln | Ser | Asn | Ser | His | Ala | Asn | Ile | Phe | Tyr | Ser |
|     | 290 |     |     |     |     | 295 |     |     |     |     | 300 |     |     |     |     |
| Val | Leu | Thr | Ile | Asp | Lys | Met | Gln | Asn | Lys | Asp | Lys | Gly | Leu | Tyr | Thr |
| 305 |     |     |     |     | 310 |     |     |     |     | 315 |     |     |     |     | 320 |
| Cys | Arg | Val | Arg | Ser | Gly | Pro | Ser | Phe | Lys | Ser | Val | Asn | Thr | Ser | Val |
|     |     |     |     | 325 |     |     |     |     | 330 |     |     |     |     | 335 |     |
| His | Ile | Tyr | Asp | Lys | Ala | Phe | Ile | Thr | Val | Lys | His | Arg | Lys | Gln | Gln |
|     |     |     | 340 |     |     |     |     | 345 |     |     |     |     | 350 |     |     |
| Val | Leu | Glu | Thr | Val | Ala | Gly | Lys | Arg | Ser | Tyr | Arg | Leu | Ser | Met | Lys |
|     |     | 355 |     |     |     |     |     | 360 |     |     |     |     | 365 |     |     |
| Val | Lys | Ala | Phe | Pro | Ser | Pro | Glu | Val | Val | Trp | Leu | Lys | Asp | Gly | Leu |
|     | 370 |     |     |     |     | 375 |     |     |     |     | 380 |     |     |     |     |
| Pro | Ala | Thr | Glu | Lys | Ser | Ala | Arg | Tyr | Leu | Thr | Arg | Gly | Tyr | Ser | Leu |
| 385 |     |     |     |     | 390 |     |     |     |     | 395 |     |     |     |     | 400 |
| Ile | Ile | Lys | Asp | Val | Thr | Glu | Glu | Asp | Ala | Gly | Asn | Tyr | Thr | Ile | Leu |
|     |     |     |     | 405 |     |     |     |     | 410 |     |     |     |     | 415 |     |
| Leu | Ser | Ile | Lys | Gln | Ser | Asn | Val | Phe | Lys | Asn | Leu | Thr | Ala | Thr | Leu |
|     |     |     | 420 |     |     |     |     | 425 |     |     |     |     | 430 |     |     |
| Ile | Val | Asn | Val | Lys | Pro | Gln | Ile | Tyr | Glu | Lys | Ala | Val | Ser | Ser | Phe |
|     |     | 435 |     |     |     |     |     | 440 |     |     |     |     | 445 |     |     |
| Pro | Asp | Pro | Ala | Leu | Tyr | Pro | Leu | Gly | Ser | Arg | Gln | Ile | Leu | Thr | Cys |
|     | 450 |     |     |     |     | 455 |     |     |     |     | 460 |     |     |     |     |
| Thr | Ala | Tyr | Gly | Ile | Pro | Gln | Pro | Asn | Thr | Ile | Lys | Trp | Phe | Trp | His |
| 465 |     |     |     |     | 470 |     |     |     |     | 475 |     |     |     |     | 480 |
| Pro | Cys | Asn | His | Asn | His | Ser | Glu | Ala | Arg | Cys | Asp | Phe | Cys | Ser | Asn |
|     |     |     | 485 |     |     |     |     | 490 |     |     |     |     | 495 |     |     |
| Asn | Glu | Glu | Ser | Phe | Ile | Leu | Asp | Asn | Asn | Asn | Asn | Asn | Asn | Asn | Ala |
|     |     |     | 500 |     |     |     |     | 505 |     |     |     |     | 510 |     |     |
| Asp | Ser | Asn | Met | Gly | Asn | Arg | Ile | Glu | Ser | Ile | Thr | Gln | Arg | Met | Ala |
|     |     | 515 |     |     |     |     |     | 520 |     |     |     |     | 525 |     |     |
| Ile | Ile | Glu | Gly | Lys | Asn | Lys | Met | Ala | Ser | Thr | Leu | Val | Val | Ala | Asp |
|     |     | 530 |     |     |     |     | 535 |     |     |     |     | 540 |     |     |     |
| Ser | Arg | Ile | Ser | Gly | Ile | Tyr | Ile | Cys | Ile | Ala | Ser | Asn | Lys | Val | Gly |
| 545 |     |     |     |     | 550 |     |     |     |     | 555 |     |     |     |     | 560 |
| Thr | Val | Gly | Arg | Asn | Ile | Ser | Phe | Tyr | Ile | Thr | Asp | Val | Pro | Asn | Gly |
|     |     |     |     | 565 |     |     |     |     | 570 |     |     |     |     | 575 |     |
| Phe | His | Val | Asn | Leu | Glu | Lys | Met | Pro | Thr | Asn | Asn | Glu | Gly | Glu | Asp |
|     |     |     | 580 |     |     |     |     | 585 |     |     |     |     | 590 |     |     |

```
Leu  Lys  Leu  Ser  Cys  Thr  Val  Asn  Lys  Phe  Leu  Tyr  Arg  Asp  Val  Thr
          595                      600                     605
Trp  Ile  Leu  Leu  Asn  Asn  Asn  Asn  Asn  Asn  Asn  Asn  Asn  Asn  Asn  Asn
610                           615                               620
Asn  Asn  Asn  Asn  Asn  Arg  Thr  Val  Asn  Asn  Arg  Thr  Met  His  Tyr  Ser
625                      630                      635                          640
Ile  Ser  Lys  Gln  Lys  Met  Ala  Ile  Thr  Lys  Glu  His  Ser  Ile  Thr  Leu
               645                      650                           655
Asn  Leu  Thr  Ile  Met  Asn  Val  Ser  Leu  Gln  Asp  Ser  Gly  Thr  Tyr  Ala
               660                      665                     670
Cys  Arg  Ala  Arg  Asn  Val  Tyr  Thr  Gly  Glu  Glu  Ile  Leu  Gln  Lys  Lys
          675                     680                          685
Glu  Ile  Thr  Ile  Arg  Asp  Gln  Glu  Ala  Pro  Tyr  Leu  Leu  Arg  Asn  Leu
690                          695                     700
Ser  Asp  His  Thr  Val  Ala  Ile  Ser  Ser  Ser  Thr  Thr  Leu  Asp  Cys  His
705                     710                     715                          720
Ala  Asn  Gly  Val  Pro  Glu  Pro  Gln  Ile  Thr  Trp  Phe  Lys  Asn  Asn  His
                    725                     730                          735
Lys  Ile  Gln  Gln  Glu  Pro  Gly  Ile  Ile  Leu  Gly  Pro  Gly  Ser  Ser  Thr
               740                     745                          750
Leu  Phe  Ile  Glu  Arg  Val  Thr  Glu  Glu  Asp  Glu  Gly  Val  Tyr  His  Cys
          755                     760                          765
Lys  Ala  Thr  Asn  Gln  Lys  Gly  Ser  Val  Glu  Ser  Ser  Ala  Tyr  Leu  Thr
770                          775                     780
Val  Gln  Gly  Thr  Ser  Asp  Lys  Ser  Asn  Leu  Glu  Leu  Ile  Thr  Leu  Thr
785                     790                     795                          800
Cys  Thr  Cys  Val  Ala  Ala  Thr  Leu  Phe  Trp  Leu  Leu  Leu  Thr  Leu  Leu
                    805                     810                          815
Ile  Arg  Lys  Met  Lys  Arg  Ser  Ser  Asn  Ser  Glu  Ile  Lys  Thr  Asp  Tyr
               820                     825                     830
Leu  Ser  Ile  Ile  Met  Asp  Pro  Asp  Glu  Val  Pro  Leu  Asp  Glu  Gln  Cys
          835                     840                     845
Glu  Arg  Leu  Pro  Tyr  Asp  Ala  Ser  Lys  Trp  Glu  Phe  Ala  Arg  Glu  Arg
850                          855                     860
Leu  Lys  Leu  Gly  Lys  Ser  Leu  Gly  Arg  Gly  Ala  Phe  Gly  Lys  Val  Val
865                     870                     875                          880
Gln  Ala  Ser  Ala  Phe  Gly  Ile  Lys  Lys  Ser  Pro  Thr  Cys  Arg  Thr  Val
                    885                     890                     895
Ala  Val  Lys  Met  Leu  Lys  Glu  Gly  Ala  Thr  Ala  Ser  Glu  Tyr  Lys  Ala
               900                     905                     910
Leu  Met  Thr  Glu  Leu  Lys  Ile  Leu  Thr  His  Ile  Gly  His  His  Leu  Asn
          915                     920                     925
Val  Val  Asn  Leu  Leu  Gly  Ala  Cys  Thr  Lys  Gln  Gly  Gly  Pro  Leu  Met
930                          935                     940
Val  Ile  Val  Glu  Tyr  Cys  Lys  Tyr  Gly  Asn  Leu  Ser  Asn  Tyr  Leu  Lys
945                     950                     955                          960
Ser  Lys  Arg  Asp  Leu  Phe  Phe  Leu  Asn  Lys  Asp  Ala  Ala  Leu  His  Met
                    965                     970                          975
Glu  Pro  Lys  Lys  Glu  Lys  Met  Glu  Pro  Gly  Leu  Glu  Gln  Gly  Lys  Lys
               980                     985                     990
Pro  Arg  Leu  Asp  Ser  Val  Thr  Ser  Ser  Glu  Ser  Phe  Ala  Ser  Ser  Gly
          995                     1000                    1005
Phe  Gln  Glu  Asp  Lys  Ser  Leu  Ser  Asp  Val  Glu  Glu  Glu  Glu  Asp  Ser
1010                         1015                         1020
```

```
Asp Gly Phe Tyr Lys Glu Pro Ile Thr Met Glu Asp Leu Ile Ser Tyr
1025                1030                1035                1040

Ser Phe Gln Val Ala Arg Gly Met Glu Phe Leu Ser Ser Arg Lys Cys
            1045                1050                1055

Ile His Arg Asp Leu Ala Ala Arg Asn Ile Leu Leu Ser Glu Asn Asn
            1060                1065                1070

Val Val Lys Ile Cys Asp Phe Gly Leu Ala Arg Asp Ile Tyr Lys Asn
            1075                1080                1085

Pro Asp Tyr Val Arg Lys Gly Asp Thr Arg Leu Pro Leu Lys Trp Met
            1090                1095                1100

Ala Pro Glu Ser Ile Phe Asp Lys Ile Tyr Ser Thr Lys Ser Asp Val
1105                1110                1115                1120

Trp Ser Tyr Gly Val Leu Leu Trp Glu Ile Phe Ser Leu Gly Gly Ser
                1125                1130                1135

Pro Tyr Pro Gly Val Gln Met Asp Glu Asp Phe Cys Ser Arg Leu Arg
                1140                1145                1150

Glu Gly Met Arg Met Arg Ala Pro Glu Tyr Ser Thr Pro Glu Ile Tyr
            1155                1160                1165

Gln Ile Met Leu Asp Cys Trp His Arg Asp Pro Lys Glu Arg Pro Arg
1170                1175                1180

Phe Ala Glu Leu Val Glu Lys Leu Gly Asp Leu Leu Gln Ala Asn Val
1185                1190                1195                1200

Gln Gln Asp Gly Lys Asp Tyr Ile Pro Ile Asn Ala Ile Leu Thr Gly
                1205                1210                1215

Asn Ser Gly Phe Thr Tyr Ser Thr Pro Ala Phe Ser Glu Asp Phe Phe
            1220                1225                1230

Lys Glu Ser Ile Ser Ala Pro Lys Phe Asn Ser Gly Ser Ser Asp Asp
            1235                1240                1245

Val Arg Tyr Val Asn Ala Phe Lys Phe Met Ser Leu Glu Arg Ile Lys
    1250                1255                1260

Thr Phe Glu Glu Leu Leu Pro Asn Ala Thr Ser Met Phe Asp Asp Tyr
1265                1270                1275                1280

Gln Gly Asp Ser Ser Thr Leu Leu Ala Ser Pro Met Leu Lys Arg Phe
                1285                1290                1295

Thr Trp Thr Asp Ser Lys Pro Lys Ala Ser Leu Lys Ile Glu Val
            1300                1305                1310
```

( 2 ) INFORMATION FOR SEQ ID NO:6:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:6:

```
Ala Ser Pro Gly Leu Ala Ser Pro Gly Leu Thr Tyr Arg Met Glu Thr
1               5                   10                  15

Val Ala Leu Pro Arg Ala Ser Pro Gly Leu Met Glu Thr
            20                  25
```

( 2 ) INFORMATION FOR SEQ ID NO:7:

( i ) SEQUENCE CHARACTERISTICS:
      ( A ) LENGTH: 70 base pairs
      ( B ) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:7:

ACATGCATGC CACCATGCAG CGGGGCGCCG CGCTGTGCCT GCGACTGTGG CTCTGCCTGG    60

GACTCCTGGA    70

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACATGCATGC CCCGCCGGTC ATCC    24

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGGAATTCCC CATGACCCCA AC    22

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCATCGATGG ATCCTACCTG AAGCCGCTTT CTT    33

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCCAAGCTTG GATCCAAGTG GCTACTCCAT GACC    34

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (  i  i  ) MOLECULE TYPE: cDNA (  x  i  ) SEQUENCE DESCRIPTION: SEQ ID NO:12:

GTTGCCTGTG ATGTGCACCA  20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CTGGAGTCGA CTTGGCGGAC T  21

( 2 ) INFORMATION FOR SEQ ID NO:14:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGCGGATCCC TAGTGATGGT GATGGTGATG TCTACCTTCG ATCATGCTGC CCTTATCCTC  60

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CTGGAGTCGA CTTGGCGGAC T  21

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CGGGATCCCT CCATGCTGCC CTTATCCT  28

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGCAAGCTTG AATTCGCCAC CATGCAGCGG GGCGCC  36

( 2 ) INFORMATION FOR SEQ ID NO:18:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:18:

GTTGCCTGTG ATGTGCACCA       20

( 2 ) INFORMATION FOR SEQ ID NO:19:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:19:

CTGGAGTCGA CTTGGCGGAC T      21

( 2 ) INFORMATION FOR SEQ ID NO:20:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:20:

CGCGGATCCA AGCTTACTTA CCTTCCATGC TGCCCTTATC CTCG      44

FLT4, A RECEPTOR TYROSINE KINASE

This is a Continuation-In-Part of U.S. application Ser. No. 07/959,951, filed Oct. 9, 1992, now abandoned.

FIELD OF THE INVENTION

The present invention relates generally to genes for receptors, specifically receptors for tyrosine kinases, their insertion into recombinant DNA vectors, and the production of the resulting proteins in host strains of micro-organisms and host eukaryotic cells. More specifically the present invention is directed to FLT4, a receptor for tyrosine kinase, to nucleotide sequences encoding FLT4, and to methods for the generation of DNAs encoding FLT4 and their gene products.

BACKGROUND

The cellular behavior responsible for the development, maintenance and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long term readjustment of cellular gene expression. Several receptors associated with various cell surfaces can bind specific growth factors.

Tyrosine phosphorylation is one of the key modes of signal transduction across the plasma membrane. Several tyrosine kinase genes encode transmembrane receptors for polypeptide growth factors and hormones, such as epidermal growth factor (EGF), insulin, insulin-like growth factor-I (IGF-I), platelet derived growth factors (PDGF-A and -B) and fibroblast growth factors (FGFs) [Heldin et al., Cell Regulation, 1, 555–566 (1990); Ullrich et al., Cell, 61, 243–54 (1990)]. The receptors of several hematopoietic growth factors are tyrosine kinases; these include c-fms, which is the colony stimulating factor 1 receptor [Sherr et al., Cell, 41, 665–676 (1985)] and c-kit, a primitive hematopoietic growth factor receptor [Huang et al., Cell, 63, 225–33 (1990)].

On the basis of structure, receptors for tyrosine kinases may be divided into evolutionary subfamilies [Ullrich et al., Cell, 61, 243–54 (1990)] EGF receptor-like (subclass I) and insulin receptor-like (subclass II) kinases contain repeated homologous cysteine-rich sequences in their extracellular domains. A single cysteine-rich region is found also in the extracellular domains of the eph-like kinases [Hirai et al., Science, 238, 1717–1720 (1987), Lindberg et al. Mol. Cell. Biol., 10, 6316–24 (1990), Lhotak et al., Mol. Cell. Biol., 11, 2496–2502 (1991)]. PDGF receptors as well as c-fms and c-kit receptors for CSF-1 and SCF may be grouped in subclass III, while the FGF receptors form subclass IV. Typical for the members of both of these subclasses are extracellular folding units stabilized by intrachain disulfide bonds. These so-called immunoglobulin ("Ig") like folds are found in the proteins of the immunoglobulin superfamily, which family contains a wide variety of other cell surface receptors having either cell-bound or soluble ligands [Williams et al., Ann. Rev. Immunol., 6, 381–405 (1988)].

These receptors differ in their specificity and affinity. In general, receptors for tyrosine kinases are glycoproteins, which consist of an extracellular domain capable of binding a specific growth factor(s), a transmembrane domain which is usually an alpha-helical portion of the protein, a juxtamembrane domain (where the receptor may be regulated by e.g., protein phosphorylation), a tyrosine kinase domain (which is the enzymatic component of the receptor), and a carboxy terminal tail, which in many receptors is involved in recognition and binding of the substrates for the tyrosine kinase.

In several receptors for tyrosine kinases, the processes called alternative splicing and alternative polyadenylation are capable of producing several distinct polypeptides from the same gene. These may or may not contain the various domains listed above. As a consequence, some extracellular domains may be expressed as separate proteins secreted by the cells and some forms of the receptors may lack the tyrosine kinase domain and contain only the extracellular domain inserted to the plasma membrane via the transmembrane domain plus a short carboxy terminal tail.

A number of growth factors, growth factor receptors and other loci with known or possible relevance to growth, differentiation, or maturation within the myeloid/erythroid lineage, map in the long arm ("5q") of chromosome 5. They include IL3-5, CSF1, FGFA as well as CSF1R, PDGFRB, FGFR4 and FLT4 [Aprelikova et al., Cancer Res. 52, 746–748, (1992); Warrington et al., Genomics, 11, 701–708 (1991)]. Acquired partial deletion of the chromosome 5q arm occurs in myeloproliferative disorders and acute myeloid leukemias.

Among ligands for receptor tyrosine kinases, the Platelet Derived Growth Factor (PDGF) has been shown to be angiogenic, albeit weakly, in the chick chorioallantoic membrane. Transforming Growth Factor α (TGFα) is an angiogenic factor secreted by several tumor cell types and by macrophages. Hepatocyte Growth Factor (HGF), the ligand of the c-met proto-oncogene-encoded receptor, is also strongly angiogenic, inducing similar responses to those of TGFa in cultured endothelial cells.

Striking new evidence shows that there are endothelial cell specific growth factors and receptors that may be primarily responsible for the stimulation of endothelial cell growth, differentiation, as well as certain of differentiated functions. The most-widely studied growth factor is Vascular Endothelial Growth Factor (VEGF), a member of the PDGF family. Vascular endothelial growth factor is a dimeric glycoprotein of disulfide-linked 23 kDa subunits, discovered because of its mitogenic activity toward endothelial cells and its ability to induce vessel permeability (hence its alternative name vascular permeability factor). Other reported effects of VEGF include the mobilization of intracellular $Ca^{2+}$, the induction of plasminogen activator and plasminogen activator inhibitor-1 synthesis, stimulation of hexose transport in endothelial cells, and promotion of monocyte migration in vitro. Four VEGF isoforms encoded by distinct mRNA splicing variants appear to be equally capable of stimulating mitogenesis of endothelial cells. The 121 and 165 amino acid isoforms of VEGF are secreted in a soluble form, whereas the isoforms of 189 and 206 amino acid residues remain associated with the cell surface and have a strong affinity for heparin. Soluble non-heparin binding and heparin binding forms have also been described for the related placenta growth factor (PIGF; 131 and 152 amino acids, respectively), which is expressed in placenta, trophoblastic tumors, and cultured human endothelial cells.

The pattern of VEGF expression suggest its involvement in the development and maintenance of the normal vascular system and in tumor angiogenesis. During murine development, the entire 7.5 day post-coital endoderm expresses VEGF and the ventricular neuroectoderm produces VEGF at the capillary ingrowth stage. On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized, VEGFR-1/FLT-1 (fms-like tyrosine kinase-1) and VEGFR-2/Kdr/Flk-1 (kinase insert domain containing receptor/fetal liver kinase-1). These receptors are classified in the PDGF-receptor family. However, the VEGF receptors have seven immunoglobulin-like loops in their extracellular domains as opposed to five in other members of the PDGF family and a longer kinase insert. The expression of VEGF receptors occurs mainly in vascular endothelial cells although some may also be present on monocytes and on melanoma cell lines. Only endothelial cells have been reported to proliferate in response to VEGF and endothelial cells from different sources show different responses. Thus, the signals mediated through VEGFR-1 and VEGFR-2 appear to be cell type specific.

VEGFR-1 and VEGFR-2 bind VEGF165 with affinity (Kd about 20 pM and 200 pM, respectively. Flk-1 receptor has also been shown to undergo autophosphorylation in response to VEGF, but phosphorylation of FLT-1 was barely detectable. VEGFR-2 mediated signals cause striking changes in the morphology, actin reorganization and membrane ruffling of porcine aortic endothelial cells overexpressing this receptor. In these cells, VEGFR-2 also mediated ligand-induced chemotaxis and mitogenicity; whereas VEGFR-1 transfected cells lacked mitogenic responses to VEGF. In contrast, VEGF had a strong growth stimulatory effect on rat sinusoidal endothelial cells expressing VEGFR-1. Phosphoproteins coprecipitating with VEGFR-1 and VEGFR-2 are distinct, suggesting that different signalling molecules interact with receptor specific intracellular sequences.

There is also evidence that PlGF131 and PlGF152 bind to VEGFR-1 (Kd about 200 pM) but not to VEGFR-2. Although PlGF is not a major mitogen for most endothelial cells, it potentiates the mitogenic activity of low concentrations of VEGF. At concentrations where VEGF would be expected to occupy both VEGFR-1 and VEGFR-2, PlGF had no effect. This suggests that FLT-1 functions as a "decoy" receptor having little or no signal transducing activity alone and that PlGF increases the bioavailability of low concentrations of VEGF for the signal transducing Flk-1 receptor by displacement from the FLT-1 receptor.

In in situ hybridization studies mouse VEGFR-2 mRNA expression was found in yolk sac and intraembryonic mesoderm (E7.5), from which the endothelium is derived, and later in presumptive angioblasts, endocardium and large and small vessel endothelium (E12.5). Abundant VEGFR-2 mRNA in proliferating endothelial cells of vascular sprouts and branching vessels of embryonic and early postnatal brain and decreased expression in adult brain suggested that VEGFR-2 is a major regulator of vasculogenesis and angiogenesis. VEGFR-1 expression was similarly associated with early vascular development in mouse embryos and with neovascularization in healing skin wounds. However, high levels of VEGFR-1 expression were detected in adult organs, suggesting that VEGFR-1 has a function in quiescent endothelium of mature vessels not related to cell growth. The avian homologue of VEGFR-2 was observed in the mesoderm from the onset of gastrulation, whereas the VEGFR-1 homologue was first found in cells coexpressing endothelial markers. In in vitro quail epiblast cultures FGF-2, which is required for vasculogenic differentiation of these cells, upregulated VEGFR-2 expression. The expression of both VEGF receptors was found to become more restricted later in development. In human fetal tissues VEGFR-1 and VEGFR-2 showed overlapping, but slightly different expression patterns. These data suggest that VEGF and its receptors act in a paracrine manner to regulate the differentiation of endothelial cells and neovascularization of tissues.

FLT4 is a receptor tyrosine kinase closely related in structure to the products of the VEGFR-1 and VEGFR-2 genes. Despite the similarity, the mature form of FLT4 differs from the VEGFRs in that it is proteolytically cleaved in the extracellular domain into two disulfide-linked polypeptides of 4.5 and 5.8 kb. The FLT4 gene encodes mRNAs which exhibit alternative 3' exons.

Further evidence of a distinction is that VEGF does not show specific binding to FLT4 and doesn't induce its autophosphorylation.

FLT4 gene expression appears to be more restricted than the expression of VEGFR-1 or VEGFR-2. The expression of FLT-4 first becomes detectable by in situ hybridization in the angioblasts of head mesenchyme, the cardinal vein and extraembryonically in the allantois of 8.5 day post-coital mouse embryos. In 12.5 day post-coital embryos the FLT4 signal is observed on developing venous and presumptive lymphatic endothelia, but arterial endothelia appear to be negative. During later stages of development, FLT4 mRNA becomes restricted to developing lymphatic vessels. Only the lymphatic endothelia and some high endothelial venules express FLT4 mRNA in adult human tissues and increased expression occurs in lymphatic sinuses in metastatic lymph nodes and in lymphangioma. The results support the theory of the venous origin of lymphatic vessels.

The present invention addresses a gene for a novel receptor for tyrosine kinase located on chromosome 5, identified as an unknown tyrosine kinase-homologous PCR-cDNA fragment from human leukemia cells [Aprelikova et al., Cancer Res., 52, 746–748 1992)]. This gene and its encoded protein are called FLT4. This abbreviation comes from the words fms-like tyrosine kinase 4.

SUMMARY OF THE INVENTION

The present invention provides isolated polynucleotides (e.g., DNA or RNA segments of defined structure) encoding an FLT4 receptor tyrosine kinase useful in the production of FLT4 protein and peptide fragments thereof and in recovery of related genes from other sources.

The present invention provides a recombinant DNA vector containing a heterologous segment encoding the FLT4 receptor tyrosine kinase or a related protein that is capable of being inserted into a microorganism or eukaryotic cell and that is capable of expressing the encoded protein.

The present invention provides eukaryotic cells capable of producing useful quantities of the FLT4 receptor tyrosine kinase and proteins of similar function from many species.

The present invention provides peptides that may be produced synthetically in a laboratory or by microorganisms, which peptides mimic the activity of the natural FLT4 receptor tyrosine kinase protein.

Particularly preferred are peptides selected from the group consisting of:

(a) a FLT4-short form, the nucleotide and deduced amino acid sequence of which appear in SEQ. ID NO. 1; and (b) a second formula with different nucleotide and corresponding amino acid residues at its carboxyl terminal, i.e., an FLT4-long form, the nucleotide and deduced amino acid sequence of which appears in SEQ. ID NO. 3 and having a length of 1363 amino acid residues.

DNA and RNA molecules, recombinant DNA vectors, and modified microorganisms or eukaryotic cells comprising a nucleotide sequence that encodes any of the proteins or peptides indicated above are also part of the present invention. In particular, sequences comprising all or part of the following two DNA sequences, a complementary DNA or RNA sequence, or a corresponding RNA sequence are especially preferred:

(a) the DNA sequence for FLT4-short form [SEQ ID NO 2], and (b) a second two DNA sequences for a FLT4 for where nucleotide residues 3913–4416 are changed: FLT4-long form [SEQ ID NO. 4].

DNA and RNA molecules containing segments of the larger sequence are also provided for use in carrying out preferred aspects of the invention relating to the production of such peptides by the techniques of genetic engineering and the production of oligonucleotide probes.

Because the DNA sequence encoding the FLT4 protein is identified herein, DNA encoding the FTL4 protein may be produced by, e.g., polymerase chain reaction or by synthetic chemistry using commercially available equipment, after which the gene may be inserted into any of the many available DNA vectors using known techniques of recombinant DNA technology. Furthermore, automated equipment is also available that makes direct synthesis of any of the peptides disclosed herein readily available.

Thus, the present invention may be carried out using reagents, plasmids, and microorganisms which are freely available and available to the public.

The present invention also provides a cell line source for the ligand of the FLT4 receptor tyrosine kinase. Using the conditioned medium from these cells the FLT4 ligand may be purified and cloned by using methods standard in the art. Using this conditioned medium an assay system for FLT4 ligand and dimerization inhibitors as well as inhibitors of FLT4 signal transduction are obtained, which allow for identification and preparation of such inhibitors.

In a preferred embodiment of the invention, conditioned medium from the PC-3 cell line comprises a protein or a fragment thereof, which is capable of stimulating the FLT4 receptor and regulating the growth and differentiation as well as the differentiated functions of certain endothelial cells. The FLT4 ligand or its peptides or derivatives are useful in the regulation of endothelial cell growth, differentiation and their differentiated functions and in the generation of agonists and antagonists for the ligand. Particularly, the FLT4 ligand is useful in regulating lymphatic endothelia. However, the FLT4 ligand, when purified, or produced from a recombinant source, may also stimulate related FLT1 and KDR/Flk-1 receptors.

The identification of FLT4 stimulating ligand makes it directly possible to assay for inhibitors of this ligand or inhibitors of FLT4 function. Such inhibitors are simply added to the conditioned media containing the FLT4 ligand and if they inhibit autophosphorylation, they act as FLT4 signalling inhibitors. For example, synthetic peptides may be assayed for inhibition of FLT4-ligand interaction or FLT4 dimerization. Such putative inhibitors of FLT4 and, in addition, antibodies against the FLT4 ligand, peptides or other compounds blocking FLT4 receptor-ligand interaction, as well as antisense oligonucleotides complementary to the sequence of mRNA encoding the FLT4 ligand are useful in the regulation of endothelial cells and in the treatment of diseases associated with endothelial cell function.

BRIEF DESCRIPTION OF THE FIGURES

FIGS. 2A–2F is a schematic depiction of structural features of FLT4 and a comparison with the FLT1 tyrosine kinase sequence;

FIG. 10A is a schematic depiction of cDNA inserts of clones;

FIG. 10B is a photographic reproduction of autoradiograms of hybridizations with anti-sense RNA probe and the long and short forms of FLT4 RNA;

FIG. 10C is a photographic reproduction of autoradiograms of hybridizations with anti-sense RNA probe and the long and short forms of FLT4 RNA;

DETAILED DESCRIPTION

Figure 1A:
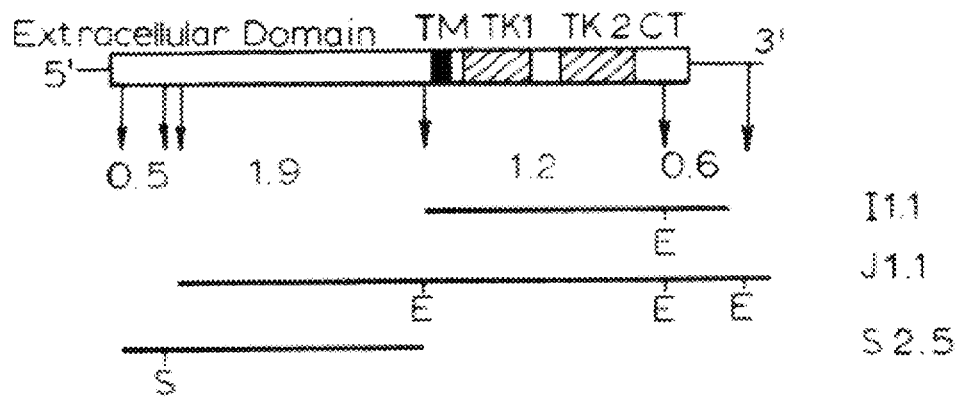
FIG. 1A is a schematic depiction of the structure of FLT4 cDNA clones.

The cloning, sequencing and expression of a novel receptor tyrosine kinase, termed FLT4, is described below. The FLT4 gene maps to chromosomal region 5q35 where many growth factors and growth factor receptors are located. The extracellular domain of FLT4 consists of seven immunoglobulin-like loops including twelve potential glycosylation sites. On the basis of structural similarities FLT4 and the previously known FLT1 and KDR/FLK1 receptors may constitute a subfamily of class III tyrosine kinases. the FLT4 gene is expressed as 5.8 kb and 4.5 kb mRNAs which were found to differ in their 3' sequences and to be differentially expressed in HEL and DAMI leukemia cells.

A Wilm's tumor cell line, a retinoblastoma cell line and a nondifferentiated teratocarcinoma cell line expressed FLT4; whereas differentiated teratocarcinoma cells were negative. Most fetal tissues also expressed the FLT4 mRNA, with spleen, brain intermediate zone and lung showing the highest levels. In human adult tissues the highest expression level was found in placenta,lung, kidney, heart and liver in decreasing order of expression. In in situ hybridization the FLT4 autoradiographic grains decorated bronchial epithelial cells of fetal lung. Immunohistochemical staining of FLT4 in fetal tissues confirmed staining of the bronchial epithelial cells. Some immunostaining was also seen in smooth muscle cells of the larger bronchi and aorta of the fetus. Expression vectors containing the FLT4 cDNA have been produced and expressed in COS and NIH3T3 cells as described in Examples 4 and 11 and in FIG. 11. Tyrosine phosphorylation of FLT4 was shown to be stimulated by fetal calf serum as well as by human serum and by human amniotic fluid in these cells. Thus, foregoing sera contain FLT4 ligand.

The FLT4 DNAs and polypeptides of the invention may be useful in the purification of the FLT4 ligand, and in the regulation of growth and differentiation of epithelial cells in various organs. They may also prove valuable in the diagnosis/treatment of certain diseases.

In the description that follows, a number of terms used in recombinant DNA (rDNA) technology are extensively utilized. In order to provide a clear and consistent understanding of the specification and claims, including the scope to be given to such terms, the following definitions are provided.

Gene. A DNA sequence containing a template for a RNA polymerase. The RNA transcribed from a gene may or may not code for a protein. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA lacking intervening sequences (introns).

Cloning vehicle. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression vector. A vehicle or vector similar to a cloning vehicle but which is capable of expressing a gene which has been cloned into it, after transformation into a host. The cloned gene is usually placed under the control of (i.e., operably linked to) certain control sequences such as promoter sequences. Expression control sequences vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites. The present invention pertains to both expression of recombinant FLT4 proteins (short and long forms), and to the functional derivatives of these proteins.

Functional Derivative. A "functional derivative" of FLT4 proteins is a protein which possesses a biological activity (either functional or structural) that is substantially similar to a biological activity of non-recombinant FLT4 proteins. A functional derivative of the FLT4 protein may or may not contain post-translational modifications such as covalently linked carbohydrate, depending on the necessity of such modifications for the performance of a specific function. The term "functional derivative" is intended to include the "fragments," "variants," "analogues," and "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art.

Fragment. A "fragment" of a molecule such as FLT4 protein is meant to refer to any variant of the molecule, such as the peptide core, or a variant of the peptide core.

Variant. A "variant" of a molecule such as FLT4 protein is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

Analogue. An "analogue", of FLT4 protein or genetic sequences is meant to refer to a protein or genetic sequence substantially similar in function to the FLT4 protein or genetic sequence herein.

DESCRIPTION OF THE PREFERRED EMBODIMENTS

The present invention is directed to what applicants have termed "FLT4", a receptor for tyrosine kinase, FLT4-encoding nucleic acid molecules (e.g. cDNAs, genomic DNAs, RNAs, anti-sense RNAs, etc.), production of FLT4 peptides or FLT4 protein from a FLT4 gene sequence and its product, recombinant FLT4 expression vectors, FLT4 analogues and derivatives, and diagnostic and/or therapeutic uses of FLT4 and related proteins, FLT4 ligands, FLT4 antagonists and anti-FLT4 antibodies.

PRODUCTION OF RECOMBINANT FLT4

Biologically active FLT4 may be produced by the cloning and expression of the FLT4-encoding sequence or its functional equivalent in a suitable host cell.

Production of FLT4 using recombinant DNA technology may be divided into a step-wise process for the purpose of description: (1) isolating or generating the coding sequence (gene) for the desired FLT4; (2) constructing an expression vector capable of directing the synthesis of the desired FLT4; (3) transfecting or transforming appropriate host cells capable of replicating and expressing the FLT4 gene and/or processing the gene product to produce the desired FLT4; and (4) identifying and purifying the desired FLT4 product.

ISOLATION OR GENERATION OF THE FLT4 GENE

The nucleotide coding sequence of FLT4 or functional equivalents thereof, may be used to construct recombinant expression vectors which will direct the expression of the desired FLT4 product. In the practice of the method of the invention, the nucleotide sequence depicted therein, or fragments or functional equivalents thereof, may be used to generate the recombinant molecules which will direct the expression of the recombinant FLT4 product in appropriate host cells. FLT4-encoding nucleotide sequences may be obtained from a variety of cell sources which produce FLT4-like activities and/or which express FLT4 encoding mRNA. Applicants have identified a number of suitable human cell sources for FLT4 including human placenta, leukemia cells and some tumor cell lines.

The FLT4 coding sequence may be obtained by cDNA cloning from RNA isolated and purified from such cell sources or by genomic cloning. The FLT4 sequence may be for example amplified by polymerase chain reaction from cDNA or genomic DNA material using techniques well known in the art. Either cDNA or genomic libraries of clones may be prepared using techniques well known in the art and may be screened for particular FLT4 DNAs with nucleotide probes which are substantially complementary to any portion of the FLT4 gene. Full length clones, i.e., those containing the entire coding region of the desired FLT4 may be selected for constructing expression vectors. Alternatively, FLT4 encoding DNAs may be synthesized in whole or in part by chemical synthesis using techniques standard in the art. Due to the inherent degeneracy of nucleotide coding sequences, other DNA sequences which encode substantially the same or a functionally equivalent amino acid sequence may be used in the practice of the method of the invention. Such alterations of FLT4 nucleotide sequences include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

CONSTRUCTION OF FLT4 EXPRESSION VECTORS

Using this information a variety of recombinant DNA vectors capable of providing the FLT4 receptor tyrosine kinase in reasonable quantities are provided. Additional recombinant DNA vectors of related structure that code for synthetic proteins having the key structural features identified herein as well as for proteins of the same family from other sources can be produced from the FLT4 receptor tyrosine kinase cDNA using standard techniques of recombinant DNA technology. A transformant expressing the FLT4 receptor tyrosine kinase has been produced as an example of this technology (see EXAMPLES 3 and 4). The newly discovered sequence and structure information can be used, through transfection of eukaryotic cells, to prepare the FLT4 receptor tyrosine kinase and its various domains for biological purposes.

IDENTIFICATION OF TRANSFECTANTS OR TRANSFORMANTS EXPRESSING FLT4 GENE PRODUCTS

The host cells which contain the recombinant coding sequence and which express the biologically active, mature product may be identified by at least four general approaches (a) DNA-DNA, DNA-RNA or RNA-antisense RNA hybridization; (b) the presence or absence of "marker" gene functions; (c) assessing the level of transcription as measured by the expression of FLT4 mRNA transcripts in the host cell; and (d) detection of the mature gene product as measured by immunoassay and, ultimately, by its biological activities.

In the first approach, the presence of FLT4 coding sequences inserted into expression vectors may be detected by DNA-DNA hybridization using probes comprising nucleotide sequences that are homologous to the FLT4 coding sequence.

In the second approach, the recombinant expression vector/host system may be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the FLT4 coding sequence is inserted within a marker gene sequence of the vector, recombinants containing that coding sequence can be identified by the absence of the marker gene function. Alternatively, a marker gene can be placed in tandem with the FLT4 sequence under the control of the same or different promoter used to control the expression of the FLT4 coding sequence. Expression of the marker in response to induction or selection indicates expression of the FLT4 coding sequence.

In the third approach, transcriptional activity for the FLT4 coding region may be assessed by hybridization assays. For example, polyadenylated RNA can be isolated and analyzed by Northern blotting using a probe homologous to the FLT4 coding sequence or particular portions thereof. Alternatively, total nucleic acids of the host cell may be extracted and assayed for hybridization to such probes.

In the fourth approach, the expression of FLT4 can be assessed immunologically, for example by Western blots, immunoassays such as radioimmunoprecipitation, enzyme-linked immunoassays and the like. The ultimate test of the success of the expression system, however, involves the detection of the biologically active FLT4 gene product. Where the host cell secretes the gene product the cell free media obtained from the cultured transfectant host cell may be assayed for FLT4 activity. Where the gene product is not secreted, cell lysates may be assayed for such activity. In either case, assays which measure ligand binding to FLT4 or other bioactivities of FLT4 may be used.

FLT4 DERIVATIVES, ANALOGUES AND PEPTIDES

The production and use of derivatives, analogues, and peptides related to FLT4 are also envisioned and are within the scope of the invention. Such derivatives, analogues, or peptides may have enhanced or diminished biological activities in comparison to native FLT4, depending on the particular application. FLT4 related derivatives, analogues, and peptides of the invention may be produced by a variety of means known in the art. Procedures and manipulations at the genetic and protein levels are within the scope of the invention. Peptide synthesis, which is standard in the art may be used to obtain FLT4 peptides. At the protein level, numerous chemical modifications may used to produce FLT4 like derivatives, analogues, or peptides by techniques known in the art, including but not limited to specific chemical cleavage by endopeptidases (e.g. cyanogen bromides, trypsin, chymotrypsin, V8 protease, and the like) or exopeptidases, acetylation, formylation, oxidation, etc.

ANTI- FLT4 ANTIBODIES

Also within the scope of the invention is the production of polyclonal and monoclonal antibodies which recognize FLT4 or related proteins.

Various procedures known in the art may be used for the production of polyclonal antibodies to epitopes of FLT4. For the production of antibodies, various host animals can be immunized by injection with FLT4, or a synthetic FLT4 peptide, including but not limited to rabbits, mice, rats, etc. Various adjuvants may be used to increase the immunological response, depending on the host species, including but not limited to Freund's (complete and incomplete) adjuvant, mineral gels such as aluminium hydroxide, surface active substances such as lysolecithin, pluronic polyols, polyanions, oil emulsions, keyhole limpet hemocyanins, dinitrophenol, and potentially useful human adjuvants such as BCG (Bacillus Calmette-Guerin) and *Corynebacterium parvum*.

A monoclonal antibody to an epitope of FLT4 may be prepared by using any technique which provides for the production of antibody molecules by continuous cell lines in culture. These include but are not limited to the hybridoma technique originally described by Köhler et al., *Nature*, 256, 495–497 (1975), and the more recent human B-cell hybridoma technique [Kosbor et al., *Immunology Today*, 4, 72 (1983)] and the EBV-hybridoma technique [Cole et al., *Monoclonal Antibodies and Cancer Therapy*, Alan R Liss, Inc., pp. 77–96 (1985)]. Antibodies against FLT4 may also be produced in bacteria from cloned immunoglobulin cDNAs. With the use of the recombinant phage antibody system it may be possible to quickly produce and select antibodies in bacterial cultures and to genetically manipulate their structure.

Antibody fragments which contain the idiotype of the molecule may be generated by known techniques. For example, such fragments include but are not limited to: the F(ab')$_2$ fragment which may be produced by pepsin digestion of the antibody molecule; the Fab' fragments which may be generated by reducing the disulfide bridges of the F(ab')$_2$ fragment, and the two Fab fragments which may be generated by treating the antibody molecule with papain and a reducing agent.

Antibodies to FLT4 may be used in the qualitative and quantitative detection of mature FLT4 and their precursor and subcomponent forms, in the affinity purification of FLT4 polypeptides, and in the elucidation of FLT4 biosynthesis, metabolism and function. Detection of FLT4 tyrosine kinase activity may be used as an enzymatic means of generating and amplifying a FLT4 specific signal in such assays. Antibodies to FLT4 may also be useful as diagnostic and therapeutic agents.

USES OF FLT4, FLT4-ENCODING NUCLEIC ACID MOLECULES AND ANTI-FLT4 ANTIBODIES

Applicants envision a wide variety of uses for the compositions of the present invention, including diagnostic and/or therapeutic uses of FLT4, FLT4 analogues and derivatives, FLT4-encoding nucleic acid molecules, anti-sense nucleic acid molecules and anti-FLT4 antibodies.

FLT4-encoding nucleic acid molecules or fragments thereof may be used as probes to detect and quantify mRNAs encoding FLT4. Assays which utilize nucleic acid probes to detect sequences comprising all or part of a known gene sequence are well known in the art. FLT4 mRNA levels may indicate emerging and/or exiting neoplasias as well as the onset and/or progression of other human diseases. Therefore, assays which can detect and quantify FLT4 mRNA may provide a valuable diagnostic tool.

Anti-sense FLT4 RNA molecules are useful therapeutically to inhibit the translation of FLT4-encoding mRNAs where the therapeutic objective involves a desire to eliminate the presence of FLT4 or to downregulate its levels. FLT4 anti-sense RNA, for example, could be useful as a FLT4 antagonizing agent in the treatment of diseases in which FLT4 is involved as a causative agent, for example due to its overexpression.

Additionally, FLT4 anti-sense RNAs are useful in elucidating FLT4 functional mechanisms. FLT4-encoding nucleic acid molecules may be used for the production of recombinant FLT4 proteins and related molecules as separately discussed in this application.

Anti-FLT4 antibodies may be used to diagnose and quantify FLT4 in various contexts. For example, antibodies against various domains of FLT4 may be used as a basis for FLT4 immunoassays or immunohistochemical assessment of FLT4. Tyrosine kinase activity of FLT4 may be useful in these assays as an enzymatic amplification reaction for the generation of a FLT4 signal. Anti-FLT4 antibodies may also be useful in studying the amount of FLT4 on cell surfaces.

Antibodies may be produced which function as FLT4 ligand agonists or antagonists whereby the regulation of FLT4 activity becomes possible. Also, random peptides may be produced by synthetic means or by recombinant means from random oligonucleotides and the ones showing specific binding to the FLT4 receptor may be selected with the aid of the FLT4 extracellular domain. Such peptides may have agonistic or antagonistic activity. FLT4 antibodies may also provide valuable diagnostic tools after conjugation to various compounds for in vivo imaging of FLT4 expressing cells and tissues or tumors.

Monoclonal antibodies against FLT4 may be coupled either covalently or noncovalently to a suitable supramagnetic, paramagnetic, electron-dense, echogenic or radioactive agent to produce a targeted imaging agent. Antibody fragments generated by proteolysis or chemical treatments or molecules produced by using the epitope binding domains of the monoclonal antibodies could be substituted for the intact antibody. This imaging agent would then serve as a contrast reagent for X-ray, magnetic resonance, sonographic or scintigraphic imaging of the human body for diagnostic purposes.

MOLECULAR BIOLOGY OF FLT4

The complete sequence of the FLT4 cDNA clones extends for 4194 or 4794 nucleotides and contains an open reading frame of 1298 or 1363 amino acids, depending on alternative splicing. The nucleotide and deduced FLT4 amino acid sequence (short form) is shown in SEQ. ID NO. 1 and No. 2. [compare to the FLT1 tyrosine kinase sequence (Shibuya et al., Oncogene, 5, 519–524 (1990).

A putative signal peptide sequence of mostly hydrophobic amino acids (boxed in FIG. 2A) follows the initiator methionine. The sequence surrounding the corresponding ATG is in agreement with the consensus translation initiation sequence [Kozak, Nucl. Acids Res., 15, 8125–8135 (1987)]. The predicted extracellular portion of both FLT4 polypeptides is 775 amino acids long and contains twelve potential sites for asparagine-linked glycosylation (NXS/T). (Underlined in FIGS. 2A–2F) It also contains several amino acid residues exhibiting a pattern of spacing described for members of the immunoglobulin superfamily of proteins [Williams et al., Annu. Rev. Immunol., 6, 381–405 (1988)], indicated in FIGS. 2A–2F with solid circles (●). It has 12 cysteine residues (FIGS 2A–2F, boxed) and it can be organized in seven immunoglobulin-like domains (Ig I–VII in FIGS. 2A–2F). The predicted Ig-like domain IV lacks cysteine residues. FIGS. 2A–2F also shows the extracellular domain of FLT1 (SEQ. ID No. 5), which is the closest human homologue of FLT4. From this figure one can see the alignment of the cysteine residues and the very similar composition of the Ig-like regions.

The cytoplasmic domain of FLT4 is separated from the extracellular part by a putative transmembrane region of 23 hydrophobic amino acid residues (FIG. 2D, boxed). This sequence is flanked on the cytoplasmic side by a basic region suggesting the junction between the transmembrane and cytoplasmic domains. The tyrosine kinase homologous domain (FIG. 2D, marked with arrows) begins at residue 843 and includes an ATP-binding pocket and a putative autophosphorylation site (FIG. 2E, marked with an open square ☐) homologous to Y416 of c-src at Y1068 (FIGS. 2A–2F). The tyrosine kinase catalytic domain of FLT4 is divided into two subdomains by a 65 amino acid sequence (aa 944–1008) which is mostly hydrophilic and does not show homology to FLT1. Unlike FLT1, FLT4 does not contain tyrosine residues in its kinase insert.

A second species of FLT4 mRNA has an alternative 3' end which encodes a longer form of the FLT4 protein.

In FIGS. 10A–C, production of short and long forms of the FLT4 mRNA by alternative splicing is illustrated. FIG. 10A shows the schematic structure of the cDNA inserts of clones J.1.1 and L1.1. The TAG stop codon of clone J.1.1 as well as the polyadenylation site (polyA) are indicated. Clone L1.1 differs from clone J.1.1 in the shaded segment (the long and short forms of FLT4 mRNA, respectively). TAA and polyA indicate the stop codon and polyadenylation site of clone L1.1. In addition, the restriction endonuclease cleavage sites for EcoRI and AvaI have been indicated. Shown below is the 256 bp EcoRI-AvaI insert of clone L1.1. used for cRNA protection analysis. The black segment indicates sequences from the polylinker in the linearized sense RNA template for transcription of the antisense strand in vitro. Shown are also the schematic structures of the protected fragments after RNAse protection analysis. FIGS. 10B and 10C, show autoradiograms of the 256 bp $^{35}$S-labeled antisense RNA probe and the 211 and 124 bp digested fragments representing the long and short forms of FLT4 RNA when protected by polyadenylated RNA from the indicated cell lines (Tera-2 is a teratocarcinoma cell line, which has been analyzed here with or without retinoic acid treatment for 10 days. The (negative) control lane shows results of protection with transfer RNA. Note the downregulation of FLT4 mRNAs during the differentiation of the Tera-2 cells. Tera-2 cells of clone 13 were provided by Dr. C. F. Graham (Department of Zoology, University of Oxford, UK). Cells between passages 18–40 were used in this study. The cells were maintained in Eagle's minimum essential medium (MEM) supplemented with 10% fetal calf serum and antibiotics. To induce differentiation, the cells were plated on gelatin-coated tissue-culture grade dishes at a density of $1.5 \times 10^3$ cells/cm$^2$. On the following day, $2 \times 10^{-6}$M RA was added to the medium. The cells were cultured in the presence of RA for up to 10 days.

Results shown in FIG. 10A–C illustrate the generation of carboxy termini of these two FLT4 (short and long) forms generated by alternative splicing.

According to the deduced amino acid sequence FLT4 belongs to class III RTKs. More specifically, FLT4 belongs to a subfamily of RTKs, which contain seven Ig-loops in their extracellular part and thus it differs from other members of class III RTKs which contain five Ig-loops. FLT4 is most closely homologous with the prototype receptor of the FLT family, FLT1, which was cloned as a v-ros-related DNA from a human genomic DNA library [Shibuya et al., Oncogene, 5, 519–524 (1990)] and with the mouse FLK1 receptor, which was cloned from hematopoietic stem cell-enriched fractions of mouse liver [Matthews et al., Cell, 65, 1143–1152 (1991); Matthews et al., Proc. Natl. Acad. Sci. USA, 88, 9026–9030 (1991)]. The extracellular domain of FLT4 shows 33% and 37% amino acid sequence identity with human FLT1 and mouse FLK1, respectively. FLT1 and FLK1, like FLT4 are widely expressed in various normal tissues, such as lung, heart, kidney and brain. In addition, a recently identified human endothelial cell receptor tyrosine kinase KDR [Terman et al., Oncogene, 6, 1677–1683 (1991)] shows considerable homology with FLT4 and the other FLT family members. From the available sequence data one may calculate that KDR is 81% identical with FLT4 in the tyrosine kinase domain. In addition, the extracellular domain of KDR also has a seven Ig-loop structure (personal communication from Dr. Bruce Terman) and its TK1 and TK2 domains are 95% and 97% identical with the corresponding domains of mouse FLK1 receptor. This suggests that KDR is the human homologue of mouse FLK1.

While the FLT4 TK domain is about 80% identical with the TK domains of FLT1 and FLK1/KDR, it is only about 60% identical with the TK domains of other receptors of the RTK class III. As these other receptors also have only five Ig-like domains in the extracellular region, one can classify FLT4, FLT1 and FLK1/KDR in a separate FLT subfamily within class III RTKs.

The tyrosine residue located in the sequence D/E-D/E-Y-M/V-P/D/E-M [Cantley, et al., Cell, 64, 281–302 (1991)]

(SEQ. ID NO. 6) in kinase inserts of PDGFRs, c-fms and c-kit is an autophosphorylation site, which, when phosphorylated, binds the SH2 domain of phosphatidylinositol 3'-kinase (PI-3K) [Reedijk et al., *EMBO J.*, 11, 1365–1372 (1992)]. Interestingly, unlike these class III RTKs, members of the FLT subfamily or the FLT3/FLK2 receptor do not contain such consensus motifs.

The eight human class III RTK genes are clustered in three different chromosomes. Chromosome 4 contains the c-kit, PDGFR-a and KDR genes [Yarden et al., *EMBO J.*, 6, 3341–3351 (1987); Stenman et al., *Genes, Chromosomes, Cancer*, 1, 155–158 (1989); Terman et al., *Oncogene*, 6, 1677–1683 (1991)]. The FLT1 and FLT3 genes are located in chromosome 13q12 [Satoh et al., *Jpn. J. Cancer Res.*, 78, 772–775 (1987); Rosnet et al., *Genomics*, 9, 380–385 (1991) ], while FLT4 is localized in chromosome 5 band q35 [Aprelikova et al., *Cancer Res.*, 52, 746–748 (1992)]; close to the fms and PDGFR-β genes [Warrington et al., *Genomics*, 11, 701–708 (1991). The long arm of chromosome 5 is involved in translocations found in leukemia cells. Deletions of part of the long arm of chromosome 5 were found in the bone marrow cells of patients with refractory anemia and macrocytosis [Van Den Berghe et al., *Nature*, 251, 437–439 (1974)]. An abnormal 5q chromosome is found in a few other myeloproliferative diseases, such as refractory anemia with excess blasts [Swolin et al., *Blood*, 58, 986–993 (1981)], agnogenic myeloid metaplasia [Whang-Peng et al., *Leuk. Res.*, 2, 41–48 (1978)], chronic myelogenous leukemia [Tomiyasu et al., *Cancer Genet. Cytogenet.*, 2, 309–315 (1980)], polycythemia vera [Van Den Berghe et al., *Cancer Genet. Cytogenet.*, 1, 157–162 (1979)] and essential thrombocythemia [Nowell et al., *Cancer*, 42, 2254–2260 (1978)].

The findings on FLT4 mRNA expression suggest that its protein product is characteristic for the bipotential hematopoietic cell lineage retaining erythroid and megakaryoblastic differentiation capacities. Several differentiation antigens shared between megakaryoblastic and endothelial cells have been shown to exist, one example being the platelet glycoprotein IIIa [Ylänne et al., *Blood*, 72, 1478–1486 (1988); Kieffer et al., *Blood*, 72, 1209–1215 (1988); Berridge et al., *Blood*, 66, 76–85 (1985)]. In addition, FLT4 is expressed by epithelial cells of the lung bronchi and kidney during the fetal period.

EXAMPLE 1

Isolation and characterization of cDNA clones encoding FLT4

MATERIALS AND METHODS

An oligo-dT primed human HEL cell cDNA library in bacteriophage lambda gt11 [A kind gift from Dr. Mortimer Poncz, Childrens Hospital of Philadelphia, Pa.; Poncz et al., *Blood*, 69, 219–223 (1987)] was screened with the cDNA fragment PCR-amplified from the same library [Aprelikova et al., *Cancer Res.*, 52, 746–748 (1992)]. Positive plaques were identified and purified as described [Sambrook et al., *Molecular Cloning—A Laboratory Manual*, Cold Spring Harbor Laboratory Press, (1989)]. cDNA inserts of bacteriophage lambda were isolated as EcoRI-fragments and subcloned into a GEM3Zf(+) plasmid (Promega). The entire FLT4 protein coding region was isolated. Three overlapping clones isolated from the HEL-library (as illustrated in FIG. 1A) were sequenced using the dideoxy chain termination method with oligonucleotide primers designed according to the sequences obtained. All portions of the cDNAs were sequenced on both strands. Sequence analyses were performed using the GCG package programs [Devereux et al., *Nucleic Acids Res.*, 12, 387–395 (1984) and the Prosite program for Apple MacIntosh].

Figure 1B:
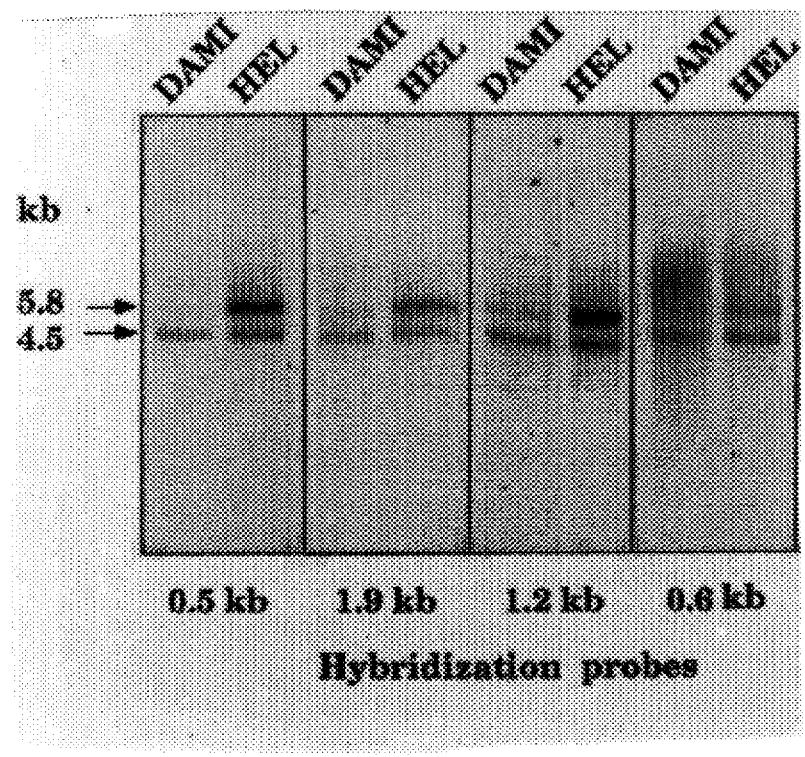
FIG. 1B is a photographic reproduction of a Northern hybridization gel.

FIG. 1A illustrates a schematic structure of the FLT4 cDNA clones analyzed. Arrows delineate subcloned restriction fragments (whose sizes are shown in kb) used for probing Northern blots in B. E=EcoRI site, S=SphI site. FIG. 1B illustrates Northern hybridization analysis of DAMI and HEL leukemia cell RNAs with the probes shown in A. Note that the 1.0 kb probe detects predominantly the 5.8 kb mRNA form.

RESULTS

A 200 bp long FLT4 cDNA fragment isolated by a PCR cloning method from a HEL cell cDNA library was used as a molecular probe to screen an oligo dT-primed human erythroleukemia cell cDNA library.

Nucleotide sequence analysis of clones revealed an open reading frame of 1298 amino acid (aa) residues (FIGS. 2A–2F). The translational initiator methionine marked in the figure is surrounded by a typical consensus sequence [Kozak, *Nucleic Acids Res.*, 12, 857–872 (1984)] and followed by a hydrophobic amino acid sequence characteristic of signal sequences for translocation into the endoplasmic reticulum.

The extracellular domain of FLT4 can be aligned into seven immunoglobulin-like loops (FIG. 2A–2F). The figure shows also the comparison of the FLT4 with FLT1 which also contains very similar structures. The amino acid sequence of FLT1 is set forth as SEQ. ID NO. 5.

Amino acid residues 775–798 form a hydrophobic stretch of sequence, which is likely to function as the transmembrane domain of the receptor, followed by several basic residues on the putative cytoplasmic side of the polypeptide. The juxtamembrane domain is 44 residues long before the beginning of a tyrosine kinase sequence homology at aa 842. With the interruption of homology in the kinase insert sequence of 65 aa, this homology is first lost at 1175 aa at carboxyl terminal tail of the receptor. A search for related tyrosine kinase domains in the amino acid sequence database (Swissprot and NBRF) identifies the FLT1 and PDG-FRB tyrosine kinases with homology of about 80 and 60% in the catalytic tyrosine kinase regions respectively.

EXAMPLE 2

Preparation of antisera

Figure 12:
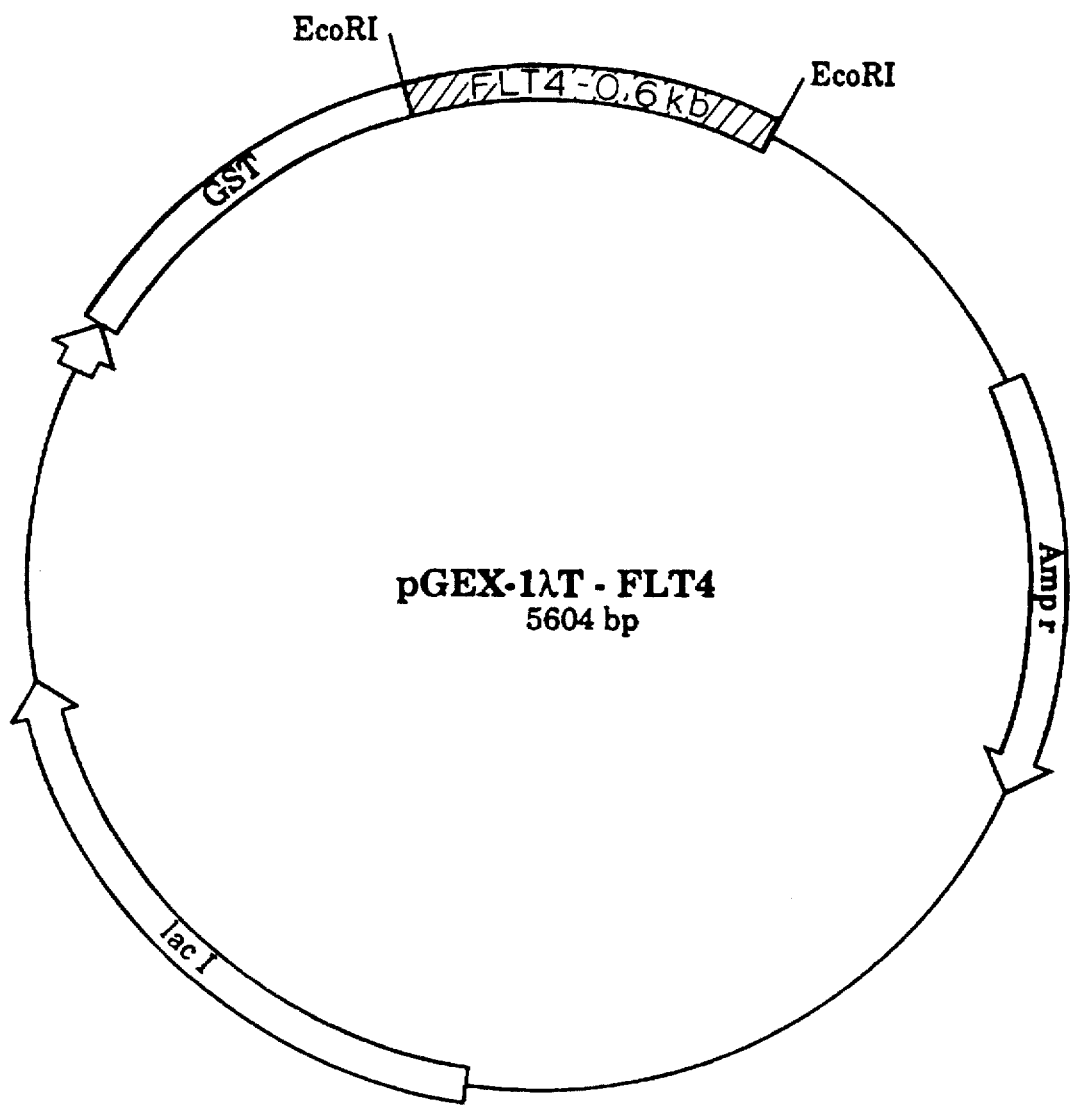
FIG. 12 is a schematic depiction of the bacterial expression vector pGEX-1λ T-FLT4.

A 657 bp EcoRI-fragment encoding the predicted C-terminus of FLT4 short form was cloned in frame with glutathione-S-transferase coding region in the pGEX-1λT bacterial expression vector (Pharmacia) as illustrated in FIG. 12 to produce a GST-FLT4 fusion protein in *E. coli*. The resulting fusion protein was produced in bacteria and partially purified by glutathione affinity chromatography according to the manufacturer's instructions. This protein was used in immunization of rabbits in order to produce polyclonal antibodies against FLT4. Antisera were used after the third booster immunization.

EXAMPLE 3

Expression of FLT4 in COS cells

MATERIALS AND METHODS

The full-length FLT4 protein coding sequence (combined from three clones, FIG. 1A) was inserted into the HindIII- BamHI site of SVpoly mammalian expression vector [Stacey et al., *Nucleic Acids Res.*, 18, 1829 (1990)]; construct SV14-2. The expression vectors (SV-FLT4 short and SV-FLT4 long, containing the respective forms of FLT4 cDNA) were introduced into COS cells by DEAE-dextran transfection method [McCutchan et al., *J. Natl. Cancer Inst.*, 41, 351–357 (1968)]. Two days after transfection the cells were washed with PBS and scraped into immunoprecipitation buffer (10 mM Tris pH 7.5, 50 mM NaCl, 0.5% sodium deoxycholate, 0.5% Nonidet P40, 0.1% SDS, 0.1 TIU/ml Aprotinin). The lysates were sonicated, centrifuged for 15' at 10,000 g and incubated overnight on ice with 3 ml of the antisera. Protein A sepharose (Pharmacia) was added and the incubation was continued for 30' with rotation. The precipitates were washed four times with the immunoprecipitation buffer, once with PBS and once with aqua before analysis in SDS-PAGE.

RESULTS

The structural predictions of the FLT4 cDNA sequence were tested by cloning the full-length FLT4 short and long protein coding regions into the HindIII-BamHI sites of the pSVpoly expression vector and transfecting these expression vectors into COS cells. The proteins produced by these two constructs differ in their C-terminus: the longer form contains 65 amino acids more than shorter form. Two days after transfection the cells were lysed and immunoprecipitated using antibodies generated against the GST-FLT4 fusion protein containing 40 carboxyl terminal amino acid residues of the short form of the predicted FLT4 protein.

Figure 13:
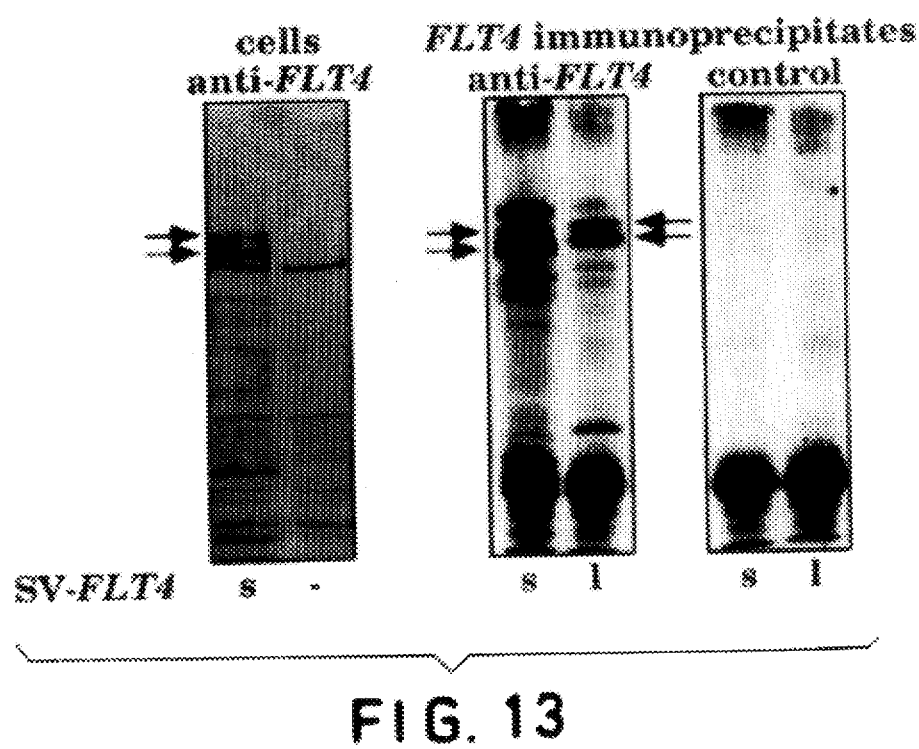
FIG. 13 is a photographic reproduction of a SDS-PAGE analysis of expression of FLT4 in COS cells.

FIG. 13 illustrates expression of FLT4 in COS cells. COS cells were transfected with SV40-based expression vectors for FLT4 (short and long forms) and immunoprecipitated with FLT4 antibodies raised against the C-terminal portion common to both forms (see FIGS. 10A–10C). Shown is a SDS-PAGE analysis of the precipitated proteins.

FIG. 13 shows analysis of the immunoprecipitated polypeptides by SDS-polyacrylamide gel electrophoresis. As can be seen from the figure, the preimmune serum does not reveal any specific bands while the FLT4-specific antibodies recognize two bands of about 170 and 190 KD. These two bands may represent differentially glycosylated forms of FLT4 protein.

EXAMPLE 4

Expression of FLT4 in NIH3T3 cells

MATERIALS AND METHODS

The full-length FLT4 cDNA (short form) was subcloned into the LTRpoly vector (Makela, et al., *Gene*, 118:293–294 (1992)) disclosing plasmid vector 77109, (GeneBank accession number x60280) containing the Moloney murine leukemia virus long terminal repeat promoter. This expression vector was used to co-transfect NIH3T3 cells with pSV2 neo marker plasmid and G418 resistant clones were analyzed for FLT4 expression.

For Western immunoblotting analyses cells on one confluent large plate were lysed in 2.5% SDS, 125 mM Tris, pH 6.5. Cell lysates were electrophoresed on SDS-page and electroblotted onto a nitrocellulose membrane. The membrane was incubated with the anti-peptide antiserum against the FLT4 carboxy terminus and bound antibodies were visualized using horseradish peroxidase conjugated swine anti-rabbit antiserum (Dako) and ECL reagents (Amersham). For metabolic labeling, the cultures were labeled with $^{35}$S-methionine as detailed below, chased for various periods in medium containing nonradioactive methionine, immunoprecipitated and analyzed by SDS-PAGE and autofluorography.

Figure 15A:
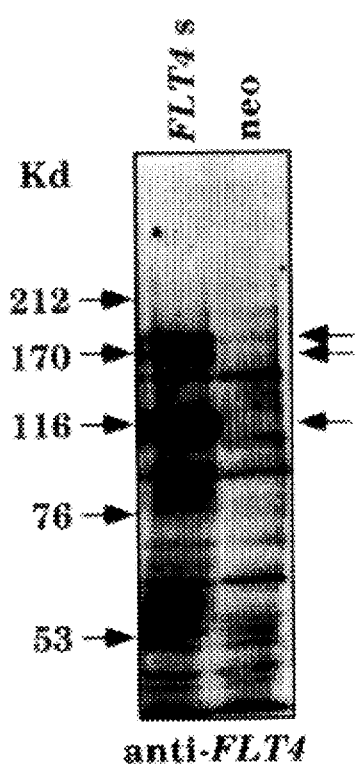
FIG. 15A is a photographic reproduction immunoblot analysis of NIH 3T3 cells expressing the FLT4 protein.
Figure 15B:
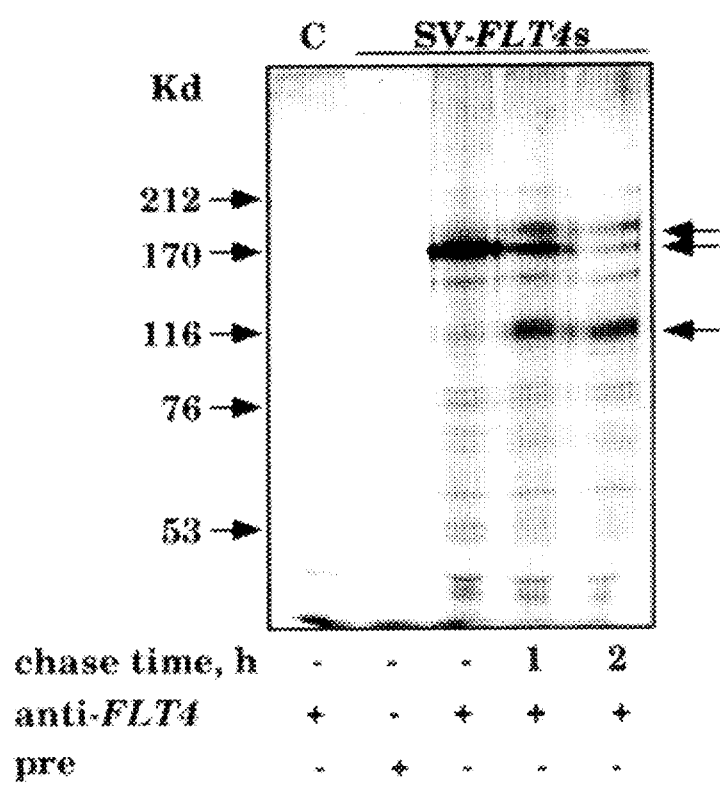
FIG. 15B is a photographic reproduction of a gel showing a pulse-chase analysis of metabolically-labeled FLT4 proteins.
Figure 16:
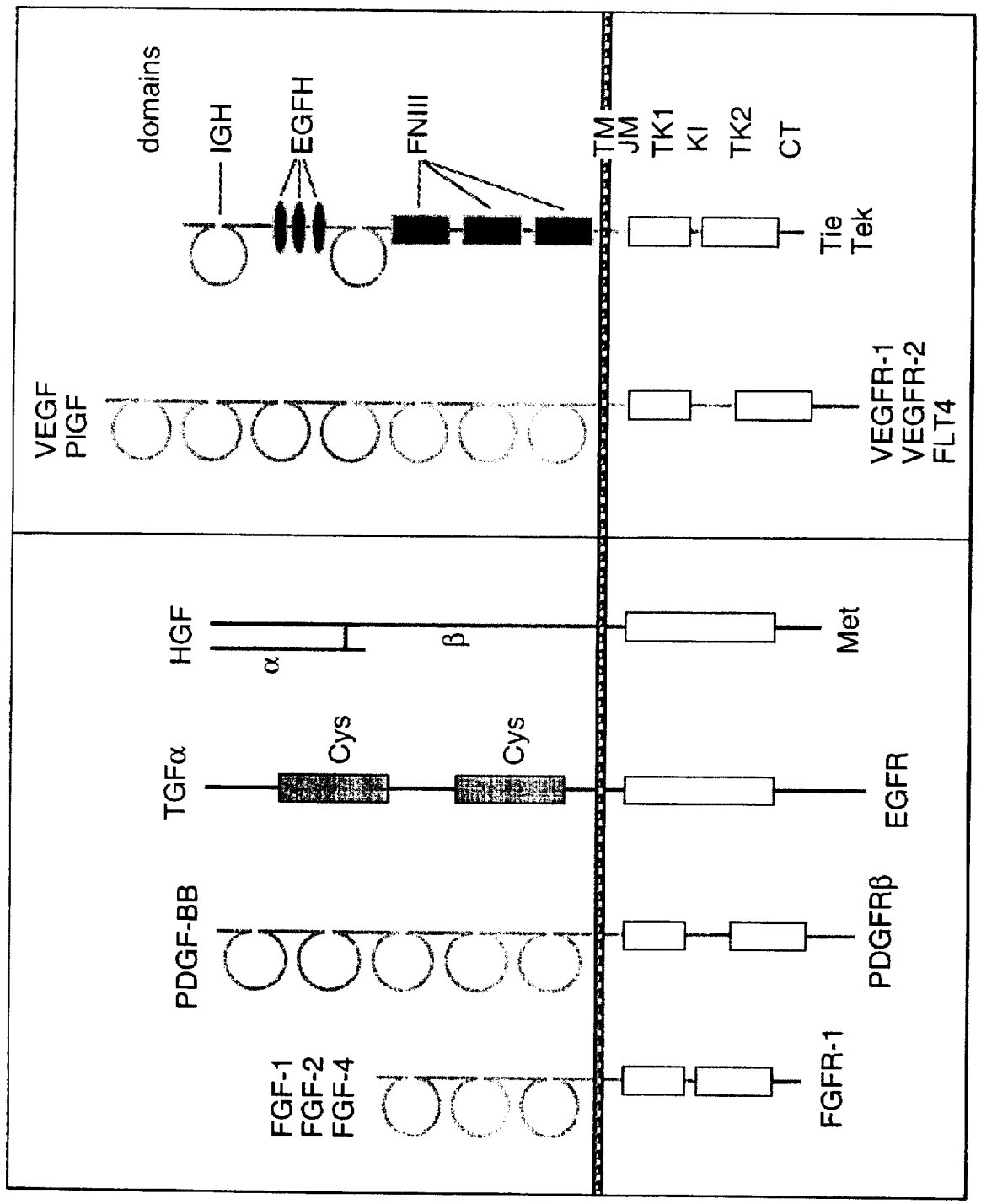
FIG. 16 is a schematic diagram of domains of several endothelial-cell specific receptors.

FIG. 15A illustrates immunoblotting analysis of NIH3T3 cells expressing the FLT4 protein. NIH3T3 cells were co-transfected with LTR-FLT4 expression vector and pSV2neo plasmid. Neomycin resistant clones were selected, and used for the experiment. The cells were lysed and the lysates were analyzed by Western blotting with the anti-FLT4 antibodies. Neomycin-resistant NIH3T3 cells (neo) were used as controls. FIG. 15B shows pulse-chase analysis of the metabolically-labelled FLT4 protein. FLT4-expressing NIH3T3 cells were labelled with 100 µCi/ml $^{35}$S-methionine for 1 h. After labelling, cells were washed twice and incubated in their growth medium for 1 or 2 h, lysed and immunoprecipitated with FLT4 antibodies. Shown is an autoradiogram of SDS-PAGE analysis of the immunoprecipitates. The mobilities of molecular weight markers have been indicated. The FLT4-specific polypeptides are indicated by arrows. Lane C shows FLT4 immunoprecipitation from untransfected COS cells. Pre-immunoprecipitation was accomplished with preimmune serum.

RESULTS

The 170 and 190 KD polypeptides could be detected in the FLT4 short form transfected into NIH3T3 cells, but not in cells transfected with pSV2neo only. In addition to these two bands there was a major band of about 120 Kd in the clones producing FLT4 (FIG. 15A). Metabolic labeling and pulse-chase experiments showed that this protein is generated as a result of posttranslational processing of the short form FLT4 polypeptides (FIG. 15B).

EXAMPLE 5

Chromosomal mapping of the FLT4 locus

MATERIALS AND METHODS

Because some clustering of class III receptor genes has been found to take place, it is of great interest to determine the chromosomal localization of FLT4. Thus, rodent-human cell hybrids were analyzed, indicating linkage of FLT4 to human chromosome 5.

Figure 3:
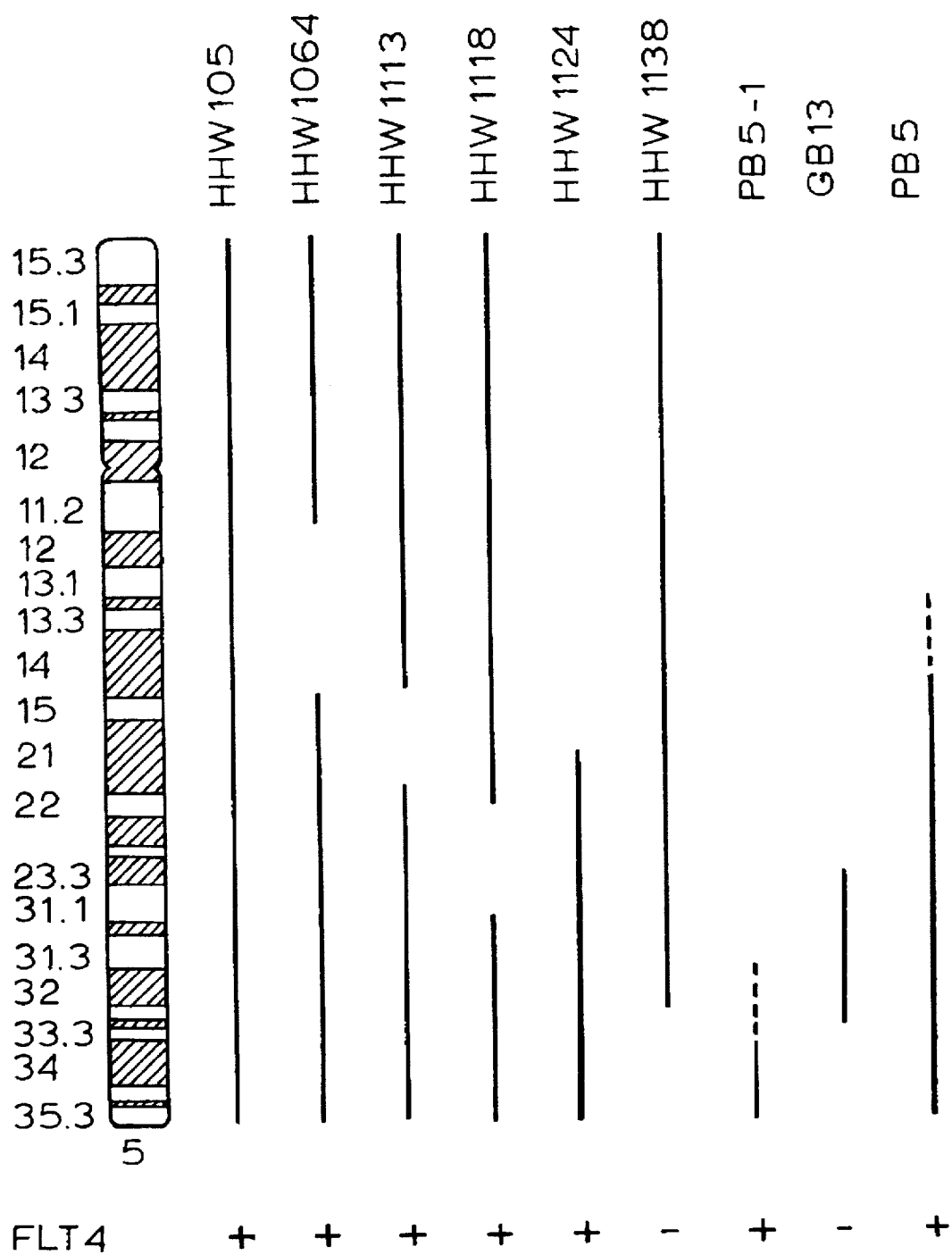
FIG. 3 is a schematic depiction of the localization of the FLT4 gene.

FIG. 3 shows localization of the FLT4 gene in the region 5q33→5qter. Rodent-human cell hybrids were analyzed, indicating linkage of FLT4 to human chromosome 5 (data not shown). Regional assignment on chromosome 5 was determined using hybrids carrying partial chromosome 5s. The portions of chromosome 5 retained in the different hybrid cell lines indicated on top of the figure are sketched to the right of the chromosome 5 ideogram. These hybrids were tested for presence of the FLT4 locus by filter hybridization and the results are shown below the sketches. The region of chromosome 5 common to FLT4 positive hybrids and absent from the FLT4 negative hybrids is 5q33.1-qter. The presence of human chromosome 5q33-qter in the hybrids is thus correlated with the presence of FLT4 sequences. The regional mapping results indicated that the FLT4 locus is telomeric to the CSF1R/platelet-derived growth factor receptor-β (PDGFRB) locus as well as to the β-adrenergic receptor (ADRBR) locus since these loci are all present in the hybrid GB13, which was negative for FLT4.

The portions of chromosome 5 retained in the different hybrid cell lines indicated on top of FIG. 3 are sketched to the right of the chromosome 5 ideogram. These hybrids were tested for presence of the FLT4 locus by filter hybridization and the results are shown below the sketches. The region of chromosome 5 common to FLT4 positive hybrids and absent from the FLT4 negative hybrids is 5q33.1-qter.

EXAMPLE 6

Expression of the FLT4 mRNA in tumor cell lines and endothelial cells

MATERIALS AND METHODS

The leukemia cell lines (K562) used in this study have been reported in several previous publications; [Lozzio et al., *Blood*, 45, 321–334 (1975)], HL-60 [Collins et al., *Nature*, 270, 347–349 (1977)], HEL [Martin et al., *Science*, 216:1233–1235 (1982)], DAMI [Greenberg et al., *Blood*, 72, 1968–1977 (1988)], MOLT-4 [Minowada et al., *J. Natl. Cancer Inst.*, 49, 891–895 (1972)], Jurkat [Schwenk et al., *Blut*, 31, 299–306 (1975)], U937 [Sundström et al., *Int. J. Cancer*, 17, 565–577 (1976)], KG-1 [Koeffler et al., *Science*, 200, 1153–1154 (1978)], JOK-1 [Andersson et al., 1982, In R. F. Revoltella (ed.), *Expression of Differentiated Functions in Cancer cells*. 239–245, Raven Press, New York] and ML-2 [Gahmberg et al., 1985, In L. C. Andersson, et al. (ed.), *Gene Expression During Normal and Malignant Differentiation*, 107–123, Academic Press, London]. The following tumor cell lines, obtained from the American Type Culture Collection were also analyzed: JEG-3, a choriocarcinoma; A205, a rhabdomyosarcoma; SK-NEP-1, a nephroblastoma; BT-474, a breast carcinoma; Y79, a retinoblastoma. The leukemia cells were grown in RPMI containing 10% FCS and antibiotics. Dami cells were cultivated in Iscove's modified DMEM with 10% horse serum. A permanent hybrid cell line (EAhy926) obtained by fusing first-passage human umbilical vein endothelial cells with the A549 lung carcinoma cells [Edgell et al., *Proc. Natl. Acad. Sci. USA*, 50, 3734–3737 (1983)] was cultured in DMEM-HAT medium containing 10% FCS and antibiotics.

Poly(A)+ RNA was extracted from the cell lines as described [Sambrook et al., see above]. 5 µg of the Poly(A)+ RNA samples were electrophoresed in agarose gels containing formaldehyde and blotted using standard conditions [Sambrook et al., see above]. The inserts of the FLT4 cDNA clones were labelled by the random priming method and hybridized to the blots. Hybridization was carried out in 50% formamide, 5×Denhardt's solution (100×Denhardt's solution is 2% each of Ficoll, polyvinylpyrrolidone and bovine serum albumin), 5×SSPE (3M NaCl, 200 mM NaH$_2$PO$_4$ H$_2$O, 20 mM EDTA, pH 7.0), 0.1% SDS (sodium dodecyl sulphate), and 0.1 mg/ml of sonicated salmon sperm DNA at 42° C. for 18–24 h. The filters were washed at 65° C. in 1×SSC (150 mM NaCl, 15 mM sodium citrate, pH 7.0), 0.1% SDS and exposed to Kodak XAR-5 film.

Figure 8:
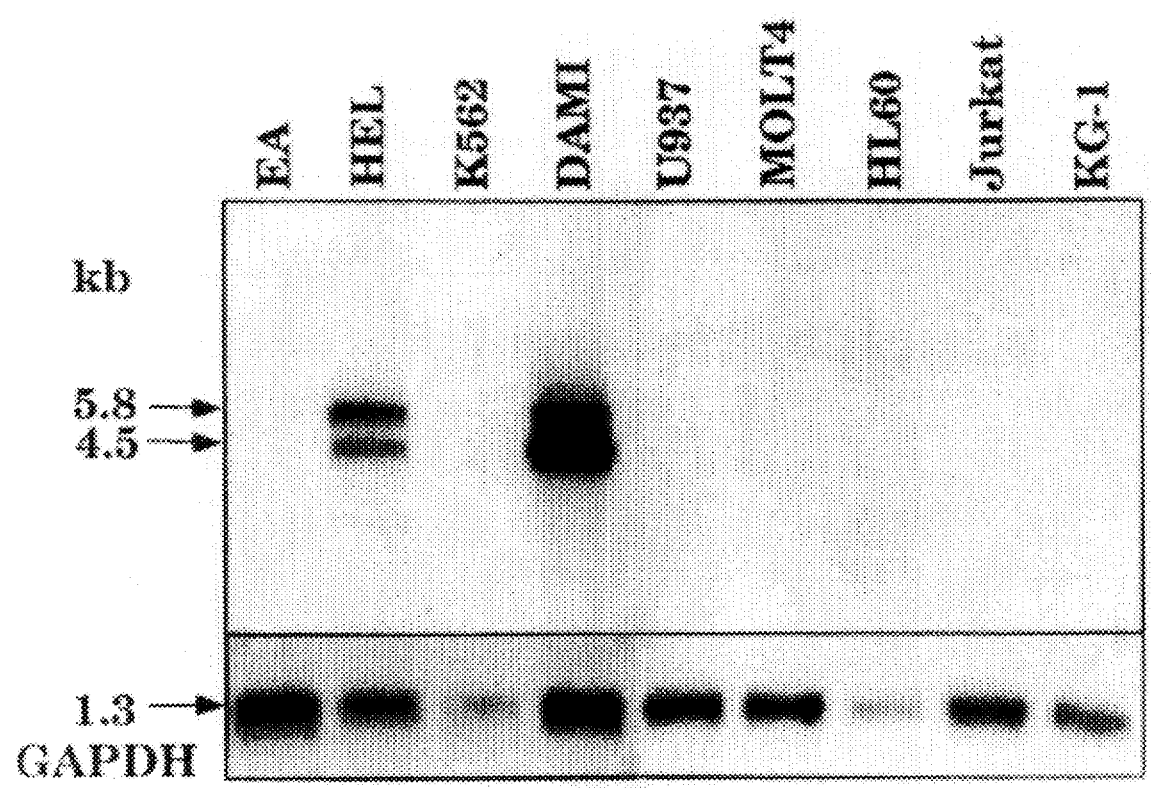
FIG. 8 is a photographic reproduction of Northern hybridization gel.

FIG. 8 shows analysis of FLT4 mRNA in endothelial and leukemia cell lines. Poly (A)$^+$ RNA from the indicated cell lines was analyzed by Northern blotting and hybridization with the FLT4 cDNA probe. Hybridization with the GAPDH probe was used as an internal control for the loading of even amounts of RNA to the analysis. Note that the endothelial hybrid cell line (EA) does not express FLT4. Of eight human leukemia cell lines tested, only the HEL and DAMI cells expressed the 5.8 kb and 4.5 kb FLT4 mRNAs.

Figure 7A:
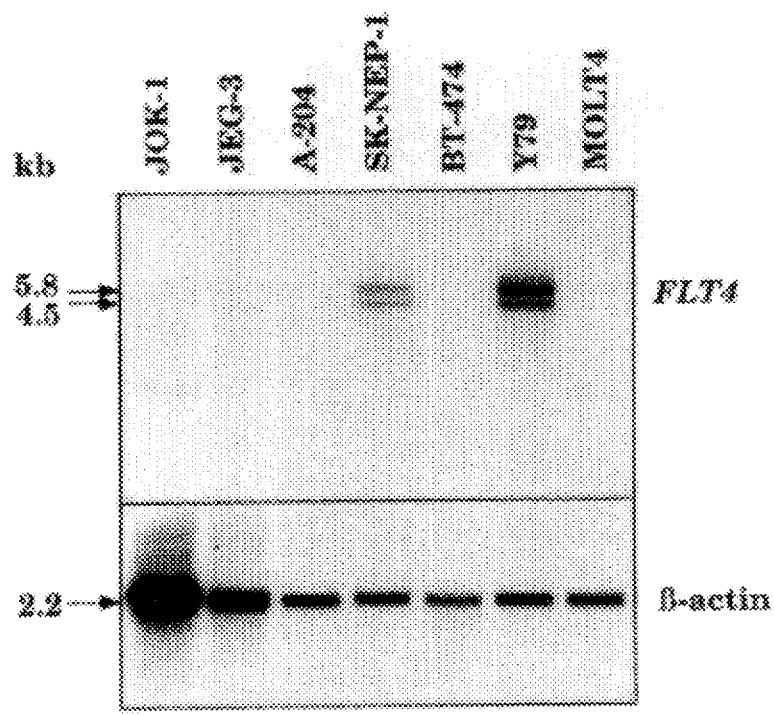
FIG. 7A is a photographic reproduction of a gel depicting FLT4 mRNA expression in tumor cell lines.
Figure 7B:
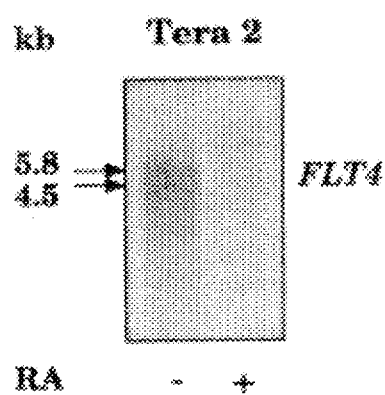
FIG. 7B is a photographic reproduction of a gel depicting differential hybridization analysis in Tera-2-teratocarcinoma cells.

FIG. 7A and FIG. 7B shows FLT4 mRNA expression in tumor cell lines. A. Poly (A)$^+$ RNA from the indicated cell lines was analyzed by Northern blotting and hybridization with the S2.5 FLT4 cDNA probe (see FIGS. 1A–1B).

Hybridization with the β-actin probe was used as an internal control for the loading of even amounts of RNA to the analysis. B. Tera-2 teratocarcinoma cells were analyzed after a 10 d treatment with vehicle (−) or retinoic acid (+) to induce neuronal differentiation [Thompson et al., *J. Cell Sci.*, 72, 37–64 (1984).

Figure 9:
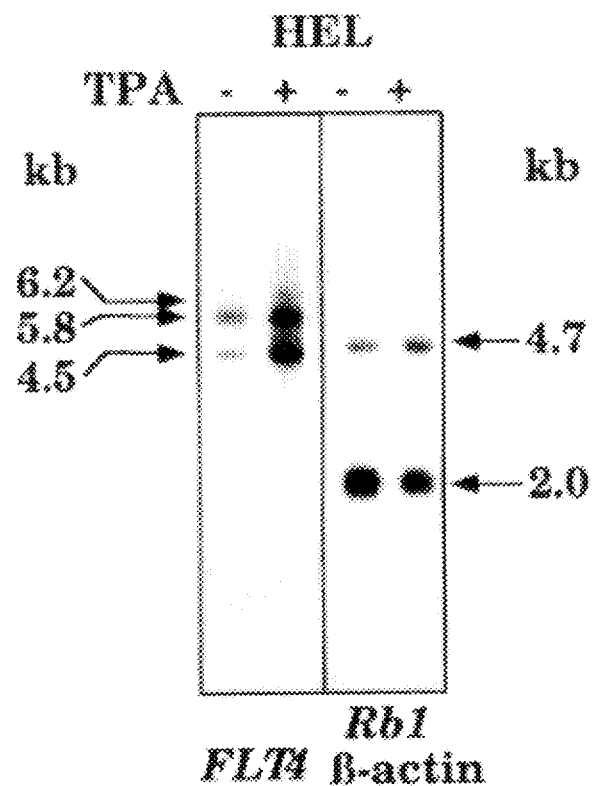
FIG. 9 is a photographic reproduction of a gel depicting an autoradiograph of hybridization results for undifferentiated and differentiated HEL cells.

FIG. 9 illustrates analysis of FLT4 mRNAs in undifferentiated and TPA-differentiated HEL cells. Both the HEL and DAMI cell lines possess a dual erythroid/megakaryoblastic phenotype and can be induced to further expression of megakaryoblastic markers by treatment with the tumor promotor 12-O-tetradecanoylphorbol-13-acetate (TPA). We analyzed whether FLT4 expression is stimulated in these cells during their differentiation. HEL cells were analyzed 2 days after treatment with TPA or with DMSO used to dissolve it. After stripping off the FLT4 signal the filter was probed with Rb-1 and β-actin cDNAs to confirm an even loading of the lanes. On the basis of densitometric scanning analysis of the autoradiograph and normalization against the constitutive expression of the GAPDH gene the mRNA level was increased about 3.4 fold in TPA-induced HEL cells.

RESULTS

FIG. 8 shows the results of analysis of FLT4 mRNA expression in ten leukemia cell lines. Only the HEL erythroleukemia cells, and DAMI megakaryoblastic leukemia cells expressed FLT4 mRNA. The K562 erythroleukemia, Jurkat and MOLT-4 T-cell leukemias, as well as HL-60 promyelocytic leukemia, U937 monocytic leukemia, and KG-1 myeloid leukemia cells were negative for the FLT4 mRNA. Of the solid tumor cell lines, only the SK-NEP-1 nefroblastoma and Y79 retinoblastoma cells contained FLT4 transcripts (FIG. 7). The FLT4 mRNA was also induced after TPA treatment of the HEL cells, when the cells undergo megakaryoblastoid differentiation (FIG. 9).

EXAMPLE 7

Expression of FLT4 in fetal lung

MATERIALS AND METHODS

In situ hybridization: Lung tissue from a 15 week-old human fetus was obtained with the permission of joint ethical committee of the University Central Hospital and the University of Turku, Finland. The sample was fixed in 100 formalin for 18 h at 4° C., dehydrated, embedded in wax and cut into 6 µm sections. The RNA probes of 206 and 157 bases (antisense and sense) were generated from linearized plasmid DNA using SP6 and T7 polymerases and [$^{35}$S]-UTP. In situ hybridization of sections was performed according to Wilkinson et al., *Development*, 99:493–500 (1987); Wilkinson, *Cell*, 50:79–88 (1987), with the following modifications: 1) instead of toluene, xylene was used before embedding in paraffin wax, 2) 6 mm sections were cut, placed on a layer of diethyl pyrocarbonate-treated water on the surface of glass slides pretreated with 2% 3-aminopropyl-triethoxysilane (Sigma), 3) alkaline hydrolysis of the probes was omitted 4) the hybridization mixture contained 60% deionised formamide, 5) the high stringency wash was for 80 min. at 65° C. in a solution containing 50 mM DTT and 1×SSC, 6) the sections were covered with NTB-2 emulsion (Kodak) and stored at 4° C. After an exposure time of 14 days the slides were developed for 2.5 min. in a Kodak D-19 developer and fixed for 5 min. with Unifix (Kodak). The sections were stained with hematoxylin in water.

For immunoperoxidase staining a 1:100 dilution of the FLT4 antibody, peroxidase-conjugated swine anti-rabbit antibodies and methods standard in the art were used. Control stainings with preimmune serum or immunogen-blocked serum did not give a signal.

Figures 6A, 6B, 6C:
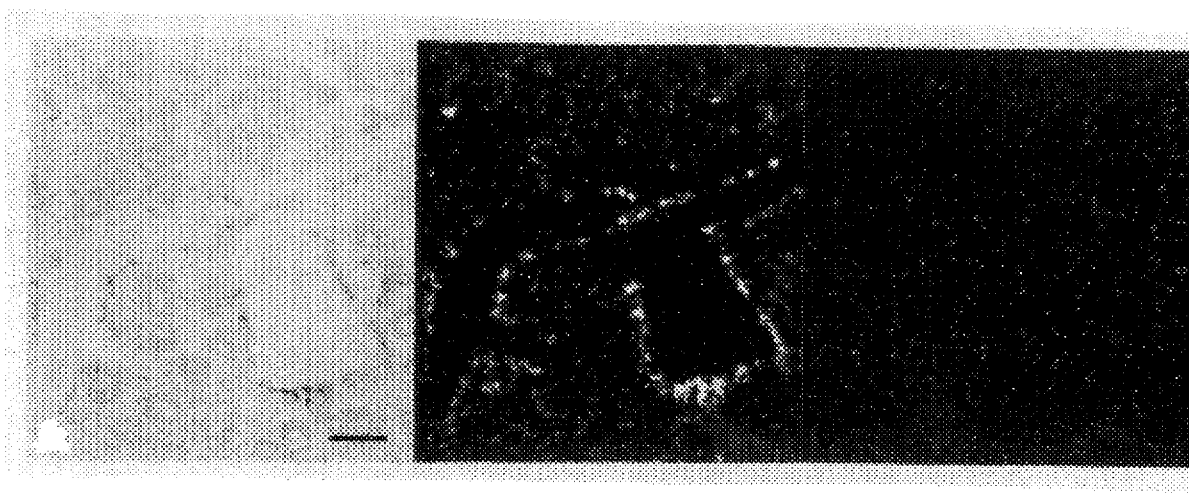
FIG. 6A is a photographic depiction of localization of hybridization of FLT4 mRNA in lightfield photography.
FIG. 6B is a photographic reproduction of a darkfield photograph of the section of FIG. 6A.
FIG. 6C is a photographic reproduction of a section depicting a darkfield photograph of a section after hybridization with sense RNA.

FIG. 6A–C illustrates localization of FLT4 mRNA in epithelial cells of developing small bronchi of a 15-week-old human fetus. To determine which cells in lung tissue possess FLT4 transcripts, in situ hybridization of human fetal lung was carried out. From the results we conclude that epithelial cells of small bronchi are mainly responsible for FLT4 expression in the lung. Hybridization with the antisense RNA is shown in light- (FIG. 6A) and darkfield photography (FIG. 6B). Hybridization with sense RNA gives a faint unspecific background (FIG. 6C) (Scale bar, 0.1 mm).

Figure 14:
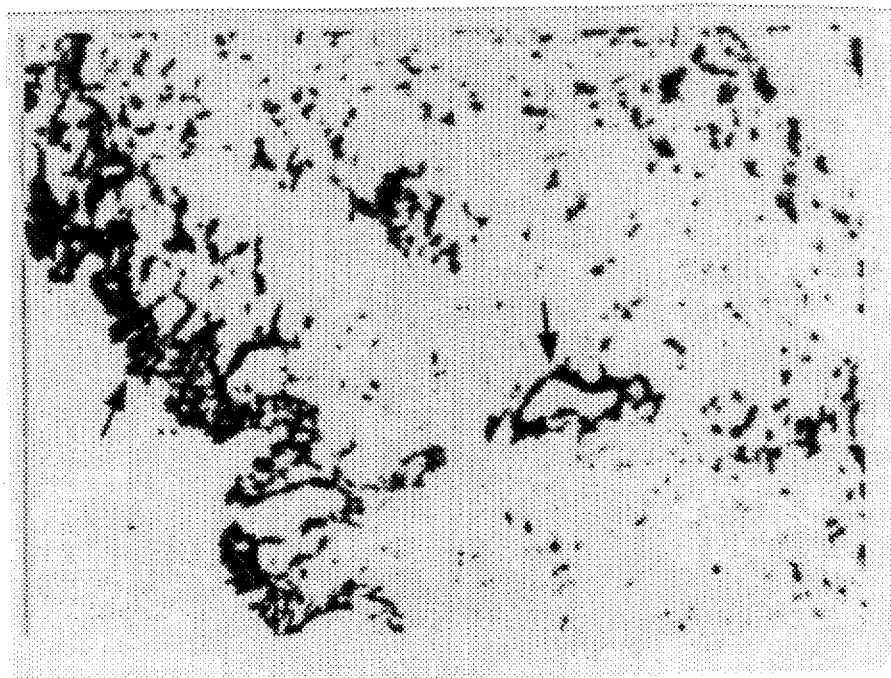
FIG. 14 is a photographic reproduction of a section showing immunoperoxidase staining of FLT4 protein in the lung of a 17 week human embryo.

FIG. 14 illustrates immunoperoxidase staining of FLT4 protein in the lung of a 17-week human embryo. The area shown contains a small bronchus in the middle and a section of a larger bronchus on the left. The epithelium of both structures is stained positive with the rabbit anti-FLT4 antiserum (arrows).

RESULTS

FLT4 mRNA expression in tissues was studied by mRNA in situ hybridization of 15 week old human fetal tissues. FLT4 mRNA was seen to be located in the epithelial cells of small bronchioli (FIG. 6A–C). Control hybridizations with sense strand and RNAse A-treated sections did not give a signal above background. Results consistent with these were obtained by anti-FLT4 immunoperoxidase staining of lung tissue of 17-week embryos (FIG. 14).

EXAMPLE 8

Figure 4:
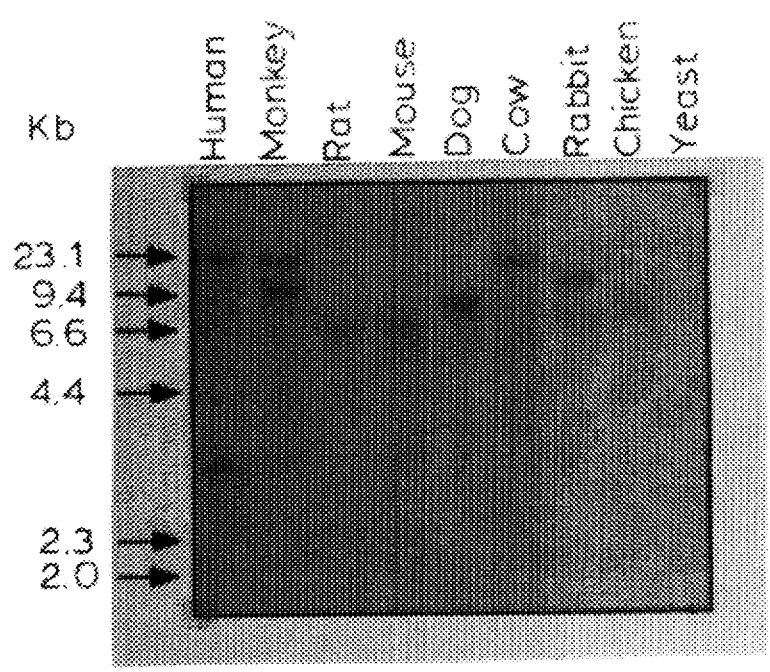
FIG. 4 is a photographic reproduction of a gel illustrating a hybridization analysis of FLT4 sequences in DNA samples from different species.

In FIG. 4 the results of an experiment examining the presence of FLT4 sequences in DNA from different species is shown. In order to reveal how well the FLT4 gene has been conserved in evolution the 2.5 kb cDNA fragment (see FIG. 1A) was hybridized to genomic DNAs purified from different animals and from yeast and digested with EcoR1. Specific bands were found in all animal species tested, but the yeast DNA did not give a signal.

EXAMPLE 9

Figure 5:
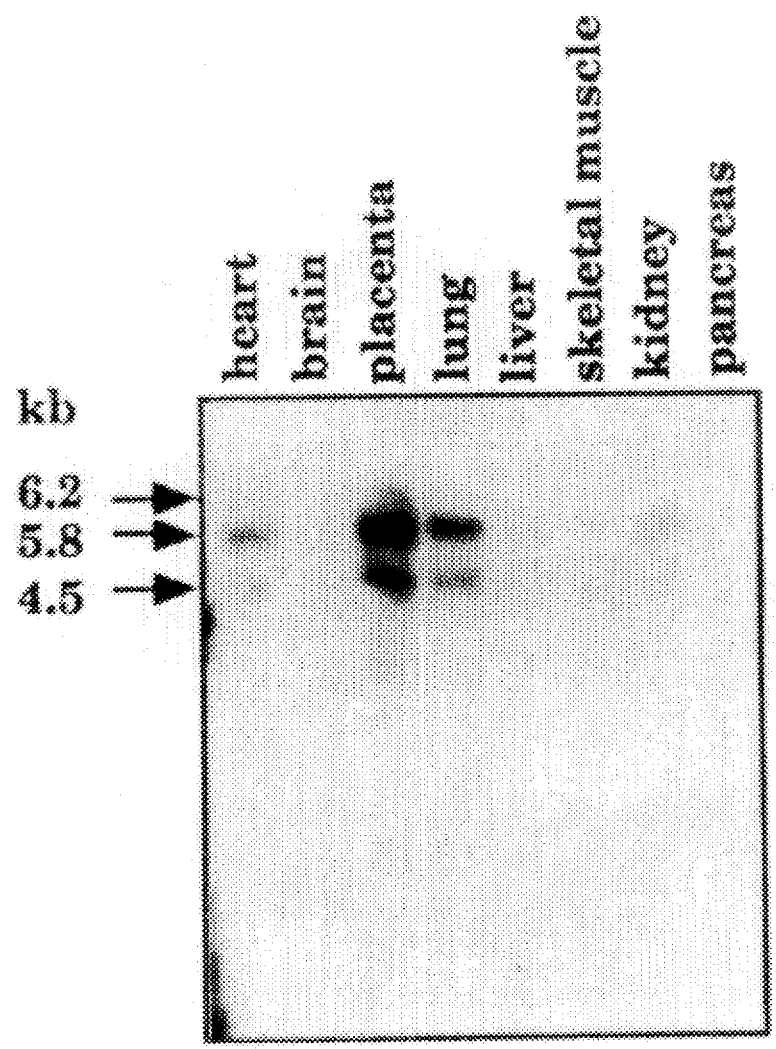
FIG. 5 is a photographic reproduction of a gel illustrating FLT4 mRNA expression in adult human tissues.

In FIG. 5, FLT4 mRNA expression in adult human tissues is illustrated. 2 mg of poly (A)$^+$ RNA from the indicated tissues (Multiple Tissue Northern Blot, Clontech Inc.) was analyzed by hybridization with the FLT4 cDNA probe. The estimated sizes of the transcripts are shown on the left. Control hybridizations with probes for constitutively expressed genes showed an even loading of the lanes (data not shown).

Hybridization of polyA$^+$ RNA from various human tissues with the FLT4 cDNA fragment showed mRNA bands of 5.8 and 4.5 kb mobility and a weakly labeled band of 6.2 kb in placenta, lung, heart and kidney. Faint mRNA bands were seen in the liver and skeletal muscle, whereas the pancreas and brain appeared to contain very little if any FLT4 RNA.

EXAMPLE 10

In an examination of FLT4 mRNA expression in human fetal tissues. A Northern blot containing total RNA from the listed tissues of 16–19 week human fetuses was hybridized with the 1.9 kb FLT4 cDNA fragment and the resulting autoradiograph was scanned with a densitometer. The results were normalized for the amount of RNA estimated from a UV picture of the corresponding EtBr stained gel. The following symbols denote mRNA levels in an increasing order: –,+,++,+++.

TABLE 1

| Fetal tissue | mRNA |
| --- | --- |
| Brain | |
| Meninges | + |
| Cortical plate | ++ |
| Intermediate zone | +++ |
| Ependymal zone | + |
| Cerebellum | ++ |
| Choroid plexus | + |
| Liver | + |
| Pancreas | + |
| Small intestine | – |
| Heart | + |
| Lung | +++ |
| Kidney | ++ |
| Adrenal | ++ |
| Skin | ++ |
| Spleen | +++ |
| Thymus | – |

Analysis of human fetal tissues showed that all except the thymus and small intestine contain FLT4 transcripts. The highest expression levels were found in lung and spleen.

EXAMPLE 11

Figure 11:
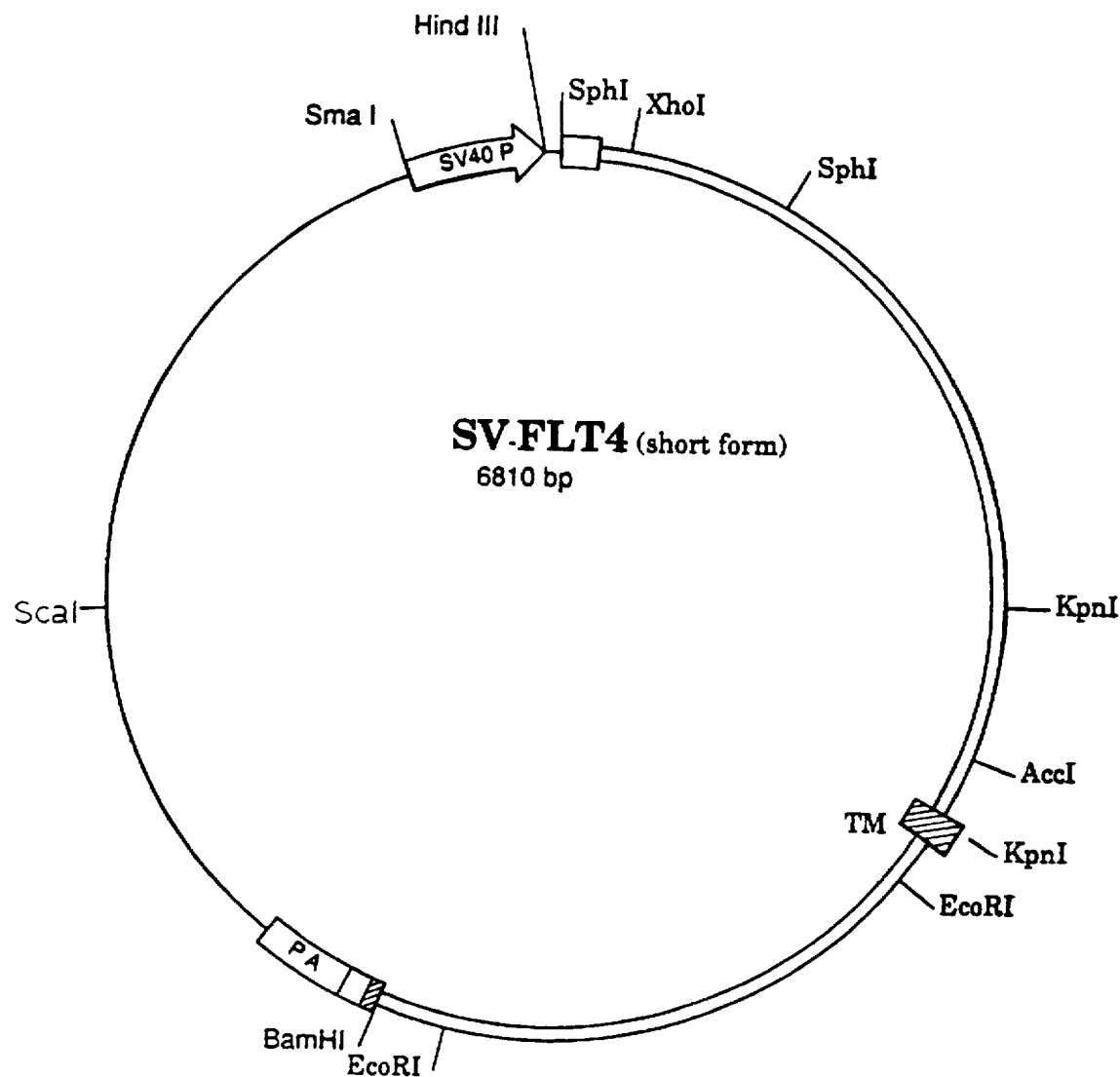
FIG. 11 is a schematic depiction of the expression vector SV-FLT4.

In FIG. 11, the structure of the SV-FLT4 expression vector is illustrated. Full-length FLT4 cDNA (short form) was produced by a) ligation of a Sph I-cleaved FLT4 PCR fragment [amplified from the S2.5 kb clone (see FIG. 1 in Pajusola et al.) using the primer oligonucleotides 5'-ACATGCATGC CACCATGCAG CGGGGCGCCG CGCTGTGCCT GCGACTGTGG CTCTGCCTGG GACTCCTGGA-3' (SEQ. ID NO. 7) (forward) and 5'-ACATGCATGC CCCGCCGGT CATCC-3' (reverse)] (SEQ. ID NO. 8) to the 5' end of the S2.5 kb fragment, subcloned into the pSP73 vector (Promega), using two SphI sites; b) ligation of PCR fragment containing last 138 bps amplified from the 0.6 kb EcoRI fragment (see FIG. 1 in Pajusola et al.) with the oligonucleotide primers 5'-CGGAATTCCC CATGACCCCA AC-3' (SEQ. ID NO. 9) (forward) and 5'-CCATCGATGG ATCCTACCTG AAGC-CGCTTT CTT-3' (SEQ. ID NO. 10) (reverse) to the 3' end of construct a) using the Eco4RI and BamHI sites; c) ligation of 1.2 kb EcoRI fragment in the EcoRI site of construct b); d) ligation of the resulting full length 3906 bp HindIII-BamHI fragment into the HindIII-BamHI cleaved SV-poly expression vector [Stacey et al., Nucl. Acids Res., 18, 2829 (1990)].

Although the present invention has been described in terms of preferred embodiments, it is not intended that the scope of the invention be limited thereby.

EXAMPLE 12

Conditioned media from the PC-3 prostatic adenocarcinoma cell line (ATCC CRL 1435) cultured for 7 days in F12 medium in the absence of fetal bovine serum (FBS) was cleared by centrifugation at 16 000×g for 20 minutes and screened for the ability to induce tyrosine phosphorylation of FLT4.

NIH3T3-cells expressing FLT4 were reseeded on 5 cm diameter cell culture dishes and grown to confluency in Dulbecco's modified minimal essential medium (DMEM) containing 10% fetal bovine serum and antibiotics. The confluent cells were washed twice in phosphate-buffered saline (PBS) and starved in DMEM/0.2% bovine serum albumin overnight. For stimulation, the starvation medium was replaced by 1 ml of the conditioned medium and the cells were incubated at 37° 0C. for 5 minutes. After stimulation the culture plates containing the cells were put on ice and washed twice with Tris-HCl, pH 7.4, 150 mM NaCl containing 100 mM NaVO$_4$. The washing solution was removed from the dishes and the cells were lysed in RIPA buffer [10 mM Tris-HCl pH 7.5, 50 mM NaCl, 0.5% sodium deoxycholate, 0.5% Nonidet P40, 0.1% sodium dodecyl sulphate (SDS)] containing aprotinin, 1 mM PMSF and 1 mM NaVO4, and the lysates were sonicated for 10 seconds twice. The lysates were then centrifuged at 16,000×g for 30 minutes and the supernatants were transferred to new tubes and used for immunoprecipitation.

The polyclonal antibodies against the FLT4 C-terminus have been described in Pajusola et al., of record. For immunoprecipitation, the supernatants were incubated for 2 hours on ice with 2 to 4 ml of rabbit polyclonal anti-FLT4 antiserum. About 30 ml of a 50% (vol/vol) solution of protein A-Sepharose (Pharmacia) in PBS was added and incubation was continued for 45 minutes with rotation at +4° C. The immunoprecipitates were washed three times with the RIPA buffer and once with PBS. The immunoprecipitates were then subjected to SDS-polyacrylamide gel electrophoresis (SDS-PAGE) in a 7.5% gel and blotted on nitrocellulose. These Western blots were incubated with monoclonal anti-P-Tyr antibodies (1:2000 dilution of PT-66 Sigma, cat. P-3300) followed by detection with peroxidase-conjugated rabbit anti-mouse antibodies (1:1000 dilution, Dako, cat. P 161) using the chemiluminescence detection system (Amersham). In some cases the blots were stripped to clear previous signals for 30 minutes at 50° C. in 100 mM 2-mercaptoethanol, 2% SDS, 62.5 mM Tris-HCl pH 6.7 with occasional agitation and restained with anti-FLT4 antibodies (1:1000 dilution) followed by staining with peroxidase-conjugated swine anti-rabbit antibodies (1:1000 dilution, Dako, P217). As a positive control for the tyrosine phosphorylation of FLT4, anti-FLT4 immunoprecipitates from the FLT4 expressing NIH3T3 cells treated with 100 mM of the tyrosyl phosphatase inhibitor sodium pervanadate (PerVO4) for 20 minutes were used. Treatment of cells with Sodium pervanadate was done by addition of 100 mM (final concentration) of sodium orthovanadate and 2 mM (final concentration) of Hydrogen peroxide to the cell medium and incubation of the cells for 20 minutes at 37° C. 5% CO$_2$. That procedure resulted in the generation of the peroxidized form of vanadate (vanadyl hydroperoxide), which is a very potent inhibitor of the protein tyrosine phosphatases in living cells.

Figure 17:
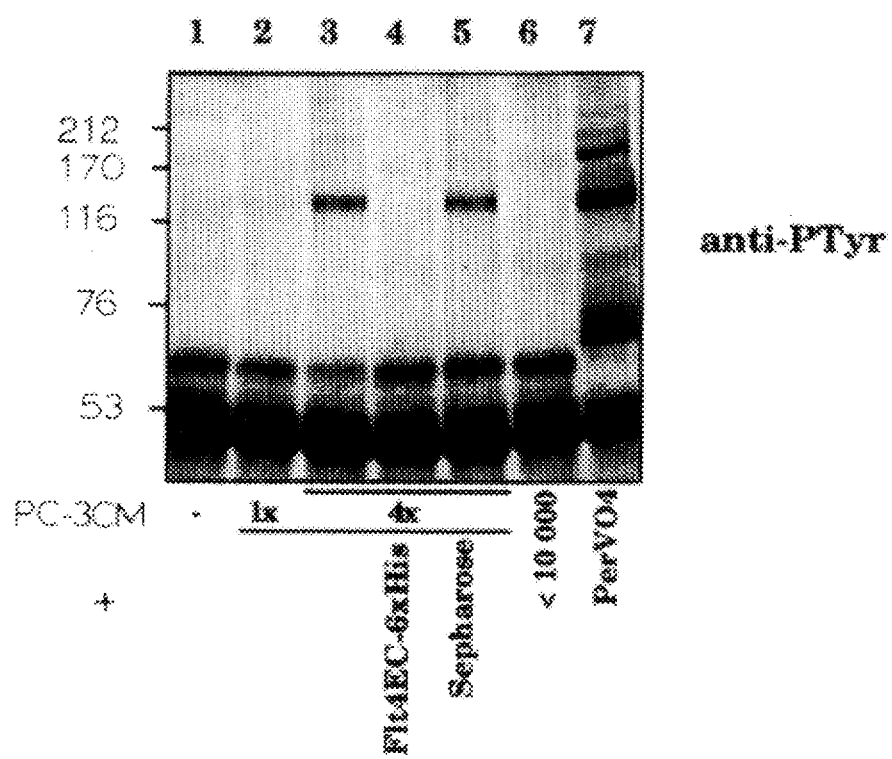
FIG. 17 is a luminogram of a Western blot showing stimulation of FLT-4 by conditioned medium from PC-3 cell cultures.
Figure 18A:
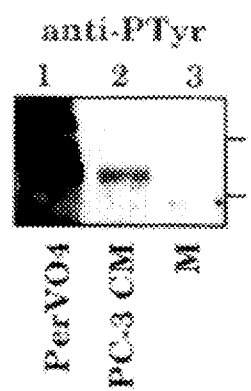
FIG. 18A–C shows gels which confirm that the tyrosine phosphorylated peptide from FLT-4 cells stimulated with PC-3 conditioned medium is the 120 kD FLT4 polypeptide.
Figure 18B:
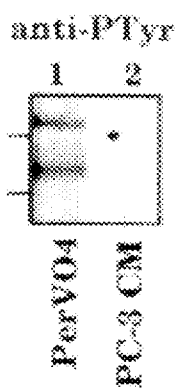
Figure 18C:
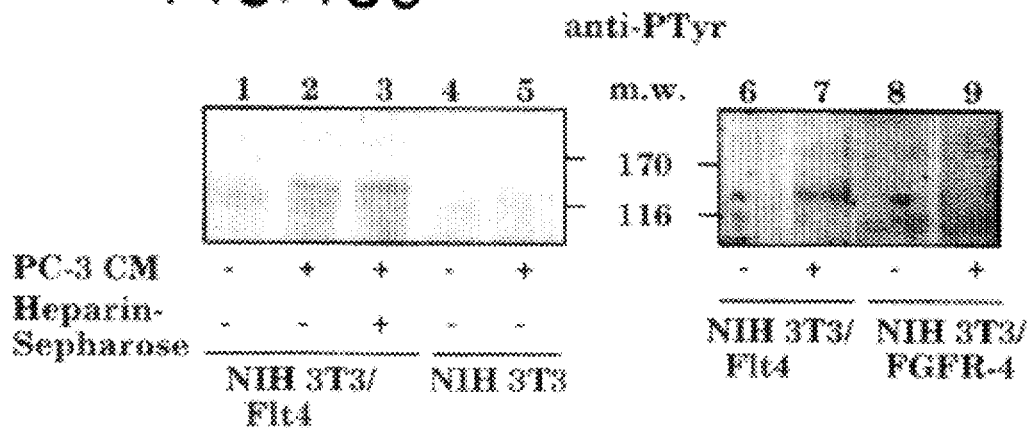

The PC-3 cell conditioned medium stimulated tyrosine phosphorylation of a 120 kD polypeptide which co-migrated with tyrosine phosphorylated, processed mature form of FLT4 (FIG. 17). In FIG. 17, the lanes, from left to right, represent: 1) unconditioned medium; 2) PC-3 conditioned medium; 3) 4×concentrated PC-3 conditioned medium; 4) 4×concentrated conditioned medium preabsorbed with 50 ml of FLT4 EC domain coupled to Sepharose; 5) 4×concentrated conditioned medium preabsorbed with Sepharose; 6) flow-through fraction from a centricon filter used to concentrate CM-3 conditioned medium; and 7) sodium pervanadate (20 minutes). Co-migration was confirmed after restaining of the blot with anti-FLT4 antibodies (FIGS. 18A–18C).

To prove that 120 kD polypeptide is not a non-specific component of the conditioned medium, 15 ml of conditioned medium were separated by SDS-PAGE, blotted on nitrocellulose, and the blot was stained with anti-P-Tyr antibodies. Several polypeptides were detected, but none of them comigrated with FLT4, indicating that the 120 kD band is indeed tyrosine-phosphorylated protein immunoprecipitated from the stimulated cells (FIGS. 18A–18C). In FIG. 18A, the upper left gel shows immunoprecipitates (anti-FLT4 antiserum) stained with anti-phosphotyrosine antibodies (lanes 1–3) or with anti-FLT4 antiserum (lanes 4–6); the gel in FIG. 18B shows tyrosyl phosphopeptides of the pervanadate-treated Sample (lane 1), electrophoresed in parallel with 15 ml of PC-3 conditioned medium (lane 2) to exclude the possibility that the 120 kd polypeptide band observed was a non-specific component of the conditioned medium. Finally, gels in FIG. 18C compare PC-3 conditioned medium stimulation (+) of untransfected cells (lanes 4 and 5), FGFR-4 transfected cells (lanes 8 and 9), and FLT-4 transfected NIH3T3 cells (lanes 1–3, 6, and 7). Analysis of stimulation by PC-3 conditioned medium pretreated with heparin Sepharose CL-6B (Pharmacia) for 2 hours at room temperature (lane 3) shows that the FLT4 ligand does not bind to heparin.

Unconditioned medium did not induce FLT4 autophosphorylation (FIG. 17, lane 1). Also, neither non-transfected NIH3T3 cells nor NIH3T3 cells transfected with the FGFR-4 showed tyrosine phosphorylation of the 120 kD polypeptide upon stimulation with the conditioned medium from PC-3 cells (FIGS. 18A–18C). Stimulating activity was considerably increased when the PC-3 conditioned medium was concentrated fourfold using a Centricon-10 concentrator (Amicon) (FIG. 17, lane 3). Also, the flow through obtained after the concentration, containing proteins of less than 10,000 molecular weight (<10,000) did not stimulate phosphorylation of FLT4 (FIG. 17, lane 6). Pretreatment of the concentrated conditioned medium of PC-3 cells with 50 ml of the FLT4 extracellular domain (FLT4EC-6xHis, see below) coupled to CNBr-activated Sepharose (1 mg/ml) according to manufacturer's instructions completely abolished the stimulation tyrosine phosphorylation of FLT4 (FIG. 17, lane 4). Analogous pretreatment of the conditioned medium with Sepharose CL-4B did not affect its stimulatory activity (FIG. 17, lane 5).

These data prove that PC-3 cells produce soluble ligand for FLT4. The above experiments prove that the ligand binds to the recombinant FLT4 EC domain. Thus, that ligand can be purified using the recombinant FLT4 EC domain in affinity chromatography. The purified protein can be electrophoresed in SDS-PAGE, blotted onto polyvinylidene difluoride (PVDF) membranes and its amino terminal sequence can be determined by methods standard in the art. Alternatively, if the amino terminus is blocked, the purified ligand can be digested to peptides for their amino terminal sequence determination. Peptide sequences obtained from the purified protein are used for the synthesis of a mixture of oligonucleotides encoding such sequences. Such oligonucleotides and their complementary DNA strand counterparts can be radioactively labelled by and used for the screening of cDNA libraries made from the PC-3 cells to obtain a cDNA encoding the ligand, all by methods standard in the art (Wen et al., 1992, Cell 69:559–572). Alternatively, such oligonucleotides and their counterparts can be used as primers in polymerase chain reaction (PCR) to amplify sequences encoding the ligand using cDNA made from PC-3 cell RNA as a template. Such method of cDNA synthesis and PCR (RT-PCR) is standard in the art (Innis et al., 1990, PCR protocols, Academic Press; McPherson, M. J. et al., 1991, PCR, a practical approach, IRL Press; Partanen et al., 1990, Proc. Natl. Acad. Sci., USA, 87:8913–8917). Yet another alternative is to clone the FLT4 ligand from the PC-3 cells by using cDNAs cloned into eukaryotic expression vector (e.g. using the Invitrogen Librarian cloning kit and vectors provided, such as pcDNA I or pcDNA III) and screening of such libraries transfected into e.g. COS cells with FLT4-alkaline phosphatase (Cheng and Flanagan Cell 79:157–168, 1994), FLT4-immunoglobulin (FLT4-Ig)(Lyman et al., 1993, Cell 75, 1157–1167) or similar affinity reagents, by methods standard in the art.

EXAMPLE 13

Cell lines and transfections. NIH3T3 cells and 293-EBNA cells (Invitrogen) were cultured in DMEM containing 10% FCS. For stable expression, NIH3T3 cells were transfected with the LTR-FLT4l vector, where the FLT4 cDNA is expressed under the control of the Moloney murine leukemia virus LTR promoter, by the lipofection method using the DOTAP transfection reagent (Boehringer-Mannheim). COS-1 cells were transfected by the DEAE dextran method (McClutchan and Pagano, 1968, J. Natl. Cancer Inst., 41:351–35).

EXAMPLE 14

Construction and expression of the fusion proteins pVTBac-FLT4EC-6xHis fusion construct. The ends of cDNA encoding FLT4 were modified as follows: The 5' end without FLT4 signal sequence encoding region was amplified by PCR using oligonucleotides 5'-CCCAA-GCTTGGATCCAAGTGGCTACTCCATGACC-3' (SEQ ID NO: 11) and 5'-GTTGCCTGTGATGTGCACCA-3' (SEQ ID NO: 12) and ligated as HindIII-Sph I fragment to FLT4 39. The 3' end of FLT4 cDNA sequence encoding the extracellular domain (EC) was amplified using oligonucleotides 5'-CTGGAGTCGACTTGGCGGACT-3' (SEQ ID NO: 13) and 5' CGCGGATCCCTAGTGATGGTG ATGGTGATGTCTACCTTCGATCATGCTGCCCTTATC-TC-3' (SEQ ID NO: 14) encoding 6 histidine residues for binding to a Ni-NTA column (Qiagen) followed by a stop codon and ligated as SalI-BamHI fragment into the LTR-FLT4l vector, replacing sequences encoding the transmembrane and cytoplasmic domains. The resulting FLT4EC-6xHis insert was then ligated as a BamHI fragment into the BamHI site in the pVTBac plasmid (Tessier et al., 1991, Gene 98, 177–183). The construct was transfected together with the baculovirus genomic DNA into SF-9 cells by lipofection, recombinant virus was generated and used for infection of High-Five cells (Invitrogen).

The FLT4-AP fusion construct. The 3' end of the sequence encoding the FLT4 EC domain was amplified using oligonucleotides 5'-CTGGAGTCGACTTGGCGGACT-3' (SEQ ID NO: 15) and 5'-CGGGATCCCTCCATGCTGCCCTTATCCT-3' (SEQ ID NO: 16) and ligated as SalI-BamHI fragment into the LTR-FLT4l vector, replacing sequences encoding the transmembrane and cytoplasmic domains. The resulting insert was then ligated as HindIII-BamHI fragment into HindIII-BglII sites of plasmid APtag-1 in frame with the alkaline phosphatase coding region (Flanagan and Leder, 1990, Cell 63, 185–194). NIH3T3 cells were co-transfected with this FLT4-AP construct and pSV2neo (Southern and Berg, 1982, J. Mol. Appl. Genet. 1, 327–341) by lipofection using the DOTAP transfection reagent (Boehringer) and the transfected cells were selected in the presence of 500 mg/ml neomycin. The recombinant protein produced into the medium was detected by a colorimetric reaction for staining for alkaline phosphatase activity (Cheng and Flanagan, 1994 Cell 79:157–168).

The ends of the cDNA encoding FLT4 were modified as follows: The 5' end including FLT4 nucleotides encoding the signal sequence was amplified by PCR using primers 5'-GGCAAGCTTGAATTCGCCACCATGCAGCGGGGC-GCC-3' (SEQ ID NO: 17) and 5'-GTTGCCTGTGATGTGCACCA-3' (SEQ ID NO: 18) and ligated as HindIII-SphI fragment into the LTR-FLT4l vector. The 3' end of FLT4 EC encoding sequence was amplified using oligonucleotides 5'-CTGGAGTCGACTTGGCGGACT-3' (SEQ ID NO: 19) and 5'-CGCGGATCCAAGCTTACTTACCTTCC-qjATGCTGCCCTTATCCTCG-3' (SEQ ID NO: 20) and ligated as SalI-BamHI fragment into the LTR-FLT4l vector replacing the sequences encoding the transmembrane and cytoplasmic domains. This FLT4EC insert containing a splice donor site was ligated first into pHgCE2 containing exons encoding the human immunoglobulin heavy chain hinge and constant region exons (Karjalainen, K., 1991, TIBTECH 9, 109–113). The EcoRI-BamHI insert containing the FLT4-Ig chimera was then blunted and ligated to the blunted HindIII site in pREP7 (Invitrogen). The construct was transfected into 293-EBNA cells by the calcium-phosphate precipitation method and the conditioned medium was used for the isolation of the FLT4-Ig protein by protein A-Sepharose affinity chromatography.

EXAMPLE 15

Purification and sequencing the FLT4 ligand. Cell culture supernatants produced by PC-3 cells under serum-depleted conditions are concentrated 30–50 fold using Centriprep filter cartridges and loaded onto a column of immobilized FLT4 extracellular domain. Two affinity matrices are prepared using the alternative constructs and methods. In the first case the Flt4EC-6xHis fusion protein is crosslinked to CNBr-activated Sepharose 4B (Pharmacia) and in the second case the FLT4-Ig fusion protein is coupled to protein A Sepharose using dimethylpimelidate (Schneider et al., 1982, J. Biol. Chem. 257: 10766–10769). The material eluted from the affinity column is subjected to further purification using ion exchange and reverse-phase high pressure chromatography and SDS-polyacrylamide gel electrophoresis. Chromatography are tested for the ability to stimulate tyrosine phosphorylation of FLT4. The purified biologically active ligand protein is microsequenced and the degenerate oligonucleotides are made based on the amino acid sequence obtained.

EXAMPLE 16

Construction of the cDNA library in an eukaryotic expression vector. Poly-A RNA was isolated from five 15 cm diameter confluent dishes of PC-3 cells by a single step method using oligo(dT) cellulose affinity chromatography. The yield was 70 mg. Approximately 6 mg of the poly-A RNA was used to prepare an oligo(dT)-primed cDNA library in the mammalian expression vector pcDNA I and the Librarian kit of Invitrogen. The library contained 106 independent recombinants with an average insert size of approximately 1800 bp.

EXAMPLE 17

Screening of the library

A. Using an oligonucleotide probe

Oligonucleotides encoding the peptide sequences obtained from the purified FLT4 ligand are used as radioactively labelled probes to screen the cDNA library prepared from the PC-3 cells. Also, PCR is performed with such oligonucleotides and their complementary sequences to amplify ligand-specific segments from cDNA. This PCR product is sequenced and then used as a probe to screen the library obtained from PC-3 cells. According to our Northern hybridization experiments, the PC-3 cells contain VEGF mRNA, but not PlGF mRNA. Thus, the PlGF cDNA probe can also be used to screen the library in low stringency hybridization conditions. Among the hybridizing clones, VEGF cDNAs will be present, but the FLT4 ligand may cross-hybridize with the PlGF probe, because it is expected to show homology to the ligands of the related FLT-1 and KDR/Flk-1 receptors.

B. Using FLT4 extracellular domain/alkaline

Clones of the library are replica plated, pooled and DNA of each pool is transiently transfected into a 10 cm diameter dish of COS cells. The expression of the FLT4 ligand is tested using FLT4-AP fusion protein according to (Flanagan and Leder, 1990, Cell 63, 185–194; Cheng and Flanagan, 1994, Cell 79:157–168). Briefly, 48 hours after transfection the cells are washed, permeabilized, incubated in the conditioned medium from NIH3T3 cells secreting the FLT4-AP protein from the transfected construct, fixed with 4% paraformaldehyde for 20 minutes, treated at 65° C. for 100 minutes to inactivate endogenous alkaline phosphatase and stained for the presence of alkaline phosphatase activity. Positive pools are identified, subdivided into secondary pools, amplified and the screening is done with successively smaller areas of the replica filters. At the each step of the screening one replica is used to isolate pooled DNA for transfection of COS cells and another is kept for the next step of the screening of area of the filter which contained the positive clone. Alternatively, COS cells are grown on PVDF membranes, fixed with 20% methanol and cells staining for the FLT4-AP activity are punched off the filter, plasmid DNA is extracted in a miniscale and used to transform bacteria. After amplification in bacteria the plasmids obtained are tested again using the same procedure. Isolated clones of plasmids are sequenced to obtain the cDNA sequence of the FLT4 ligand.

C. Using FLT4-Ig fusion protein

The method of M. J. Metzelaar et al. (J. Biol. Chem.: 1991, 266, 3239–3245) with some modifications is used. COS cells, transfected with the cDNA library the are grown on sterile PVDF membranes (0.45 mM, Millipore) in 10 cm Petri dishes for 48 hours. The membranes are washed twice with PBS, fixed with 20% methanol for 5 minutes at room temperature, washed three times with PBS, and blocked in PBS/5% bovine serum albumin (BSA, Sigma) for 4 hours at +4° C. Next, the filters are incubated for 2 hours at room temperature with FLT4-Ig fusion protein. The bound FLT-Ig was detected as described by (Lyman et al., 1993, Cell 75, 1157–1167). Briefly, radioactive iodinated antibodies specific for the Fc portion of human IgG or radioactive iodinated protein A are used. Iodination of protein A or antibodies is done by a modified chloramine-T method (Hunter & Greenwood, 1962: Nature, 194, 495–496) using Na125I (Amersham). The membranes are washed three times with ice cold PBS/0.05% between 20 and subjected to autoradiography to detect positive clones. Further screening of pools is done as described above, but using the same FLT4-Ig method.

---

What is claimed is:

1. An isolated polynucleotide comprising a nucleotide sequence encoding an human FLT4 receptor tyrosine kinase protein or FLT4 receptor tyrosine kinase precursor protein having an amino acid sequence selected from the group consisting of the amino acid sequence of SEQ ID NO: 2 from amino acid 1 to amino acid 1298, the amino acid sequence of SEQ ID NO: 4 from amino acid 1 to amino acid 1363, the amino acid sequence of SEQ ID NO: 2 from about amino acid 21 to about amino acid number 1298, and the amino acid sequence of SEQ ID NO: 4 from about amino acid 21 to about amino acid 1363.

2. The isolated polynucleotide according to claim 1 comprising the nucleotide sequence depicted in SEQ ID NO: 1 from about nucleotide number 20 to about nucleotide number 3913.

3. The isolated polynucleotide according to claim 1 comprising the nucleotide sequence depicted in SEQ ID NO: 3 from about nucleotide number 20 to about nucleotide number 4108.

4. The isolated polynucleotide according to claim 1 comprising the nucleotide sequence depicted in SEQ ID NO: 1 from about nucleotide number 80 to about nucleotide number 3913.

5. The isolated polynucleotide according to claim 1 comprising the nucleotide sequence depicted in SEQ ID NO: 3 from about nucleotide number 80 to about nucleotide number 4108.

6. An isolated polynucleotide according to claim 1 encoding an human FLT4 receptor tyrosine kinase protein or FLT4 receptor tyrosine kinase precursor protein having the amino acid sequence of SEQ ID NO: 2 from amino acid 1 to amino acid 1298.

7. An isolated polynucleotide according to claim 1 encoding an human FLT4 receptor tyrosine kinase protein or FLT4 receptor tyrosine kinase precursor protein having the amino acid sequence of SEQ ID NO: 4 from amino acid 1 to amino acid 1363.

8. An isolated polynucleotide according to claim 1 encoding an human FLT4 receptor tyrosine kinase protein or FLT4 receptor tyrosine kinase precursor protein having the amino acid sequence of SEQ ID NO: 2 from about amino acid 21 to about amino acid number 1298.

9. An isolated polynucleotide according to claim 1 encoding an human FLT4 receptor tyrosine kinase protein or FLT4 receptor tyrosine kinase precursor protein having the amino acid sequence of SEQ ID NO: 4 from about amino acid 21 to about amino acid 1363.

10. An isolated polynucleotide or oligonucleotide which hybridizes to a human gene encoding a FLT4 receptor tyrosine kinase, under hybridization conditions wherein said polynucleotide or oligonucleotide fails to hybridize to a human gene encoding FLT1, said hybridization conditions comprising:

(a) a hybridization solution comprising 50% formamide, 5×Denhardt's solution, 5×SSPE, 0.1% SDS, and 0.1 mg/ml sonicated salmon sperm DNA;

(b) hybridization at a temperature of 42° C. for a duration of 18 to 24 hours; and (c) washing following the hybridization at a wash temperature of 65° C. with a wash solution comprising 1×SSC and 0.1% SDS;

and wherein said polynucleotide or oligonucleotide consists of a continuous nucleotide sequence of at least 200 nucleotides from a nucleotide sequence selected from the group consisting of:

SEQ ID NO: 1, a nucleotide sequence complementary to SEQ ID NO: 1,

SEQ ID NO: 3, and a nucleotide sequence complementary to SEQ ID NO: 3.

11. The isolated polynucleotide or oligonucleotide of claim 10 wherein said human gene encoding a FLT4 receptor tyrosine kinase has a FLT4 coding sequence selected from the group consisting of:

(a) nucleotides 20 to 3913 depicted in SEQ ID NO: 1; and (b) nucleotides 20 to 4108 depicted in SEQ ID NO: 3.

12. A polynucleotide or oligonucleotide according to claim 10 consisting of a continuous nucleotide sequence of at least 200 nucleotides from SEQ ID NO: 1.

13. A polynucleotide or oligonucleotide according to claim 10 consisting of a continuous nucleotide sequence of at least 200 nucleotides from a nucleotide sequence complementary to SEQ ID NO: 1.

14. A polynucleotide or oligonucleotide according to claim 10 consisting of a continuous nucleotide sequence of at least 200 nucleotides from SEQ ID NO: 3.

15. A polynucleotide or oligonucleotide according to claim 10 consisting of a continuous nucleotide sequence of at least 200 nucleotides from a nucleotide sequence complementary to SEQ ID NO: 3.

16. An isolated polynucleotide or oligonucleotide which hybridizes with human messenger RNA encoding a FLT4 receptor tyrosine kinase under hybridization conditions wherein said polynucleotide or oligonucleotide fails to hybridize to human messenger RNA encoding FLT1, said hybridization conditions comprising:

(a) a hybridization solution comprising 50% formamide, 5×Denhardt's solution, 5×SSPE, 0.1% SDS, and 0.1 mg/ml sonicated salmon sperm DNA;

(b) hybridization at a temperature of 42° C. for a duration of 18 to 24 hours; and (c) washing following the hybridization at a wash temperature of 65° C., with a wash solution comprising 1×SSC and 0.1% SDS;

and wherein said polynucleotide or oligonucleotide consists of a continuous nucleotide sequence of at least 200 nucleotides from a nucleotide sequence selected from the group consisting of:

a nucleotide sequence complementary to SEQ ID NO: 1 and a nucleotide sequence complementary to SEQ ID NO: 3.

17. A polynucleotide or oligonucleotide according to claim 16 consisting of a continuous nucleotide sequence of at least 200 nucleotides from a nucleotide sequence complementary to SEQ ID NO: 1.

18. A polynucleotide or oligonucleotide according to claim 16 consisting of a continuous nucleotide sequence of at least 200 nucleotides from a nucleotide sequence complementary to SEQ ID NO: 3.

19. An expression vector comprising a polynucleotide according to claim 1, 6, 7, 8, or 9.

20. The expression vector according to claim 19, wherein said polynucleotide is operably linked to an expression control sequence.

21. A vector comprising a nucleic acid according to claim 10.

22. A vector comprising a nucleic acid according to claim 16.

23. A host cell transformed or transfected with the expression vector of claim 20.

24. The host cell according to claim 23, wherein said cell is a eukaryotic cell.

25. The host cell according to claim 24, wherein said cell is a mammalian cell.

26. A host cell transformed or transfected with the vector of claim 21.

27. A host cell transformed or transfected with the vector of claim 22.

28. A process for producing a recombinant FLT4 protein, which process comprises the steps of:

1) isolating a polynucleotide comprising a nucleotide sequence encoding a human FLT4 protein, 2) constructing an expression vector comprising the isolated polynucleotide, 3) transforming a host cell with said expression vector, 4) culturing said transformed host cell in a culture medium under conditions suitable for expression of FLT4 protein in said transformed host cell, and 5) isolating the FLT4 protein from said transformed host cell or said culture medium, wherein said FLT4 protein has an amino acid sequence selected from the group consisting of the amino acid sequence of SEQ ID NO: 2 from amino acid 1 to amino acid 1298, the amino acid sequence of SEQ ID NO: 4 from amino acid 1 to amino acid 1363, the amino acid sequence of SEQ ID NO: 2 from about amino acid 21 to about amino acid number 1298, and the amino acid sequence of SEQ ID NO: 4 from about amino acid 21 to about amino acid 1363.

29. The process according to claim 28, wherein the nucleotide sequence encoding a human FLT4 protein comprises the nucleotide sequence depicted in SEQ ID NO: 1 from about nucleotide number 20 to about nucleotide number 3913.

30. The process according to claim 28, wherein the nucleotide sequence encoding a human FLT4 protein comprises the nucleotide sequence depicted in SEQ ID NO: 3 from about nucleotide number 20 to about nucleotide number 4108.

31. The process according to claim 28, wherein the nucleotide sequence encoding a human FLT4 protein comprises the nucleotide sequence depicted in SEQ ID NO: 1 from about nucleotide number 80 to about nucleotide number 3913.

32. The process according to claim 28, wherein the nucleotide sequence encoding a human FLT4 protein comprises the nucleotide sequence depicted in SEQ ID NO. 3 from about nucleotide number 80 to about nucleotide number 4108.

33. The process for producing a recombinant FLT4 protein according to claim 28, wherein said host cell is a mammalian cell.

34. A process for producing human FLT4 receptor tyrosine kinase protein or human Flt4 receptor tyrosine kinase precursor protein, comprising the steps of:

(1) culturing in a culture medium a host cell transformed or transfected with a polynucleotide according to claim 6, under conditions suitable for expression of human FLT4 receptor tyrosine kinase protein or human Flt4 receptor tyrosine kinase precursor protein in said host cell, and (2) isolating human FLT4 receptor tyrosine kinase protein or human Flt4 receptor tyrosine kinase precursor protein from said host cell or said culture medium.

35. A process for producing human FLT4 receptor tyrosine kinase protein or human Flt4 receptor tyrosine kinase precursor protein, comprising the steps of:

(1) culturing in a culture medium a host cell transformed or transfected with a polynucleotide according to claim 7, under conditions suitable for expression of human FLT4 receptor tyrosine kinase protein or human Flt4 receptor tyrosine kinase precursor protein in said host cell, and (2) isolating human FLT4 receptor tyrosine kinase protein or human Flt4 receptor tyrosine kinase precursor protein from said host cell or said culture medium.

36. A process for producing human FLT4 receptor tyrosine kinase protein or human Flt4 receptor tyrosine kinase precursor protein, comprising the steps of:

(1) culturing in a culture medium a host cell transformed or transfected with a polynucleotide according to claim 8, under conditions suitable for expression of human FLT4 receptor tyrosine kinase protein or human Flt4 receptor tyrosine kinase precursor protein in said host cell, and (2) isolating human FLT4 receptor tyrosine kinase protein or human Flt4 receptor tyrosine kinase precursor protein from said host cell or said culture medium.

37. A process for producing human FLT4 receptor tyrosine kinase protein or human Flt4 receptor tyrosine kinase precursor protein, comprising the steps of:

(1) culturing in a culture medium a host cell transformed or transfected with a polynucleotide according to claim 9, under conditions suitable for expression of human FLT4 receptor tyrosine kinase protein or human Flt4 receptor tyrosine kinase precursor protein in said host cell, and (2) isolating human FLT4 receptor tyrosine kinase protein or human Flt4 receptor tyrosine kinase precursor protein from said host cell or said culture medium.

38. A purified FLT4 receptor tyrosine kinase protein comprising the amino acid sequence depicted in SEQ ID NO: 2 from about amino acid residue number 1 to about amino acid residue number 1298.

39. A purified FLT4 receptor tyrosine kinase protein comprising the amino acid sequence depicted in SEQ ID NO. 4 from about amino acid residue number 1 to about amino acid residue number 1363.

40. A purified FLT4 receptor tyrosine kinase protein comprising the amino acid sequence depicted in SEQ ID NO: 2 from about amino acid residue number 21 to about amino acid residue number 1298.

41. A purified FLT4 receptor tyrosine kinase protein comprising the amino acid sequence depicted in SEQ ID NO: 4 from about amino acid residue number 21 to about amino acid residue number 1363.

42. A polypeptide capable of generating an immune response specific to a human FLT4 receptor tyrosine kinase protein, said polypeptide comprising the extracellular domain of a human FLT4 receptor tyrosine kinase protein.

43. A polypeptide according to claim 42 consisting of amino acids 21 to 775 of SEQ ID NO: 2.

44. A polypeptide according to claim 42 consisting of amino acids 1 to 775 of SEQ ID NO: 2.

45. A polypeptide capable of generating an immune response specific to a human FLT4 receptor tyrosine kinase, said polypeptide comprising amino acids 1259–1298 of SEQ ID NO: 2.

* * * * *

UNITED STATES PATENT AND TRADEMARK OFFICE
CERTIFICATE OF CORRECTION

PATENT NO.      : 5,776,755
DATED           : July 7, 1998
INVENTOR(S)     : Alitalo et al.

It is certified that error appears in the above-identified patent and that said Letters Patent is hereby corrected as shown below:

<u>Title page,</u>
Item [56], References Cited, FOREIGN PATENT DOCUMENTS, delete "7/1984" and insert -- 7/1989 --; and delete "2/1992" and insert -- 8/1992 --.

OTHER PUBLICATIONS,
Under Swolin et al., delete "Cytogenic" and insert -- Cytogenetic --.
Under Tomiyasu et al., delete "Chromosome-Postive" and
insert -- Chromosome-Positive --.
Under van der Putte, delete "S.CJ.," and insert -- S.C.J., --.
Under Van Hinsberg et al., delete "Inhibitoes" and insert -- Inhibitors --.
Under Van Hinsberg et al., delete "Endothlial" and insert -- Endothelial --.
Under Wilkinson et al., delete ")1987)" and insert -- (1987) --.
Under Wilkinson et al., delete "Development" and insert -- Developing --.
Under Yarden et al., delete "Recetor" and insert -- Receptor --.
Under Oelrichs et al., delete "Kinease" and insert -- Kinase --.
Under Oelrichs et al., delete "Neuropithelium" and insert -- Neuroepithelium --.
Under Reedijik, delete "Reedijik" and insert -- Reedijk --.
Under Rosnet et al., delete "(1990)" and insert -- (1991) --.
Under Rosnet et al., delete "PDFR/CS1R" and insert -- PDFR/CSF1R --.
Under Schneider et al., delete "Immnuomatrix" and insert -- Immunomatrix --.
Under Shi et al., delete "(Fibroblasts)" and insert -- (Fibroblast) --.
Under Shi et al., delete "40-Kilodation" and insert -- 40-Kilodalton --.
Under Berridge et al., immediately before "IIb-IIIa" delete "Linkage are Associated with the Platelet".
Under Catoretti et al., delete "168-357-363" and insert -- 168:357-363 --.
Under Galland et al., delete "Kimase" and insert -- Kinase --.
Under Mollinedo et al., delete "Alkyl-Lyosophospholipid" and insert
-- Alkyl-Lysophospholipid --.
Under Moroni et al., delete "Tranforming" and insert -- Transforming --.
Under Moroni et al., delete "267(5):2714-2744" and insert -- 267(5):2714-2722 --.

UNITED STATES PATENT AND TRADEMARK OFFICE
CERTIFICATE OF CORRECTION

PATENT NO.    : 5,776,755
DATED         : July 7, 1998
INVENTOR(S)   : Alitalo et al.

It is certified that error appears in the above-identified patent and that said Letters Patent is hereby corrected as shown below:

Column 2,
Line 36, delete "TGFa" and insert -- TGFα --.

Signed and Sealed this

Second Day of July, 2002

*Attest:*

*Attesting Officer*

JAMES E. ROGAN
*Director of the United States Patent and Trademark Office*